(12) United States Patent
Rendle et al.

(10) Patent No.: US 9,359,392 B2
(45) Date of Patent: Jun. 7, 2016

(54) DENDRIMER SCAFFOLDS FOR PHARMACEUTICAL USE

(71) Applicant: Victoria Link Limited, Wellington (NZ)

(72) Inventors: Phillip Martin Rendle, Lower Hutt (NZ); Steven Toms, Wellington (NZ)

(73) Assignee: Victoria Link Limited, Wellington (NZ)

( * ) Notice: Subject to any disclaimer, the term of this patent is extended or adjusted under 35 U.S.C. 154(b) by 0 days.

(21) Appl. No.: 14/425,602

(22) PCT Filed: Sep. 5, 2013

(86) PCT No.: PCT/NZ2013/000161
§ 371 (c)(1),
(2) Date: Mar. 3, 2015

(87) PCT Pub. No.: WO2014/038963
PCT Pub. Date: Mar. 13, 2014

(65) Prior Publication Data
US 2015/0225439 A1    Aug. 13, 2015

(30) Foreign Application Priority Data

Sep. 5, 2012 (NZ) ....................................... 602259

(51) Int. Cl.
| | |
|---|---|
| *C07H 15/04* | (2006.01) |
| *A61K 47/32* | (2006.01) |
| *C07C 229/10* | (2006.01) |
| *C07C 233/18* | (2006.01) |
| *C07C 237/08* | (2006.01) |
| *A61K 47/48* | (2006.01) |
| *A61K 49/00* | (2006.01) |
| *A61K 49/12* | (2006.01) |
| *C07C 229/06* | (2006.01) |
| *C07C 229/38* | (2006.01) |

(52) U.S. Cl.
CPC ............... *C07H 15/04* (2013.01); *A61K 47/32* (2013.01); *A61K 47/48192* (2013.01); *A61K 49/0021* (2013.01); *A61K 49/0054* (2013.01); *A61K 49/124* (2013.01); *C07C 229/06* (2013.01); *C07C 229/10* (2013.01); *C07C 229/38* (2013.01); *C07C 233/18* (2013.01); *C07C 237/08* (2013.01)

(58) Field of Classification Search
CPC . A61K 47/32; A61K 49/0054; A61K 49/124; C07C 229/06; C07C 229/10; C07C 229/38; C07C 233/18; C07C 237/08
See application file for complete search history.

(56) References Cited

U.S. PATENT DOCUMENTS

2009/0036353 A1    2/2009    Behrens et al.

OTHER PUBLICATIONS

Teo et al. "Preventing acute gut wall damage in infectious diarrhoeas with glycosylated dendrimers" EMBO Mol Med (2012) 4, 866-881.*
Dendritech (https://web.archive.org/web/20120112043247/http://www.dendritech.com/pamam.html) available online Jan. 12, 2012, p. 1-2.*
Balieu et al. , Encapsulation of contrast imaging agents by polypropyleneimine-based dendrimers, J. Biomed. Mater. Res. Part A (2012), 101(3): 613-621.
Bhadra et al., Glycodendrimeric nanoparticulate carriers of primaquine phosphate for liver targeting, Int. J. Pharm. (2005), 295(1-2):221-233.
Boisselier et al., Interactions and Encapsulation of Vitamins C, B 3, and B 6 with Dendrimers in Water, Chemistry (2010), 16(20):6056-6068.
Geotti-Bianchini et al., pH-tuned metal coordination and peroxidase activity of a peptide dendrimer enzyme model with a Fe(II)bipyridine at its core, Org. Biomol. Chem. (2013), 11(2):344-352.
Greenwald et al., A New Aliphatic Amino Prodrug System for the Delivery of Small Molecules and Proteins Utilizing Novel PEG Derivatives, J. Med. Chem. (2004), 47(3):726-734.
Hafiz et al., Influence of structure on the cationic polytriethanol-ammonium bromide derivatives. III. Biological activity, Egypt. J. Chem. (2005), 48(2):245-250.
Huang et al., Novel Poly(EThyleneAmidoAmine) (PETAA) dendrimers produced througha unique and highly efficient synthesis, Polymer (2011), 52(26):5975-5984.
Irache et al., Mannose-targeted systems for the delivery of therapeutics, Expert Opin. Drug Deliv. (2008), 5(6):703-724.
Jain et al., Dendrimer toxicity: Let's meet the challenge, Int. J. Pharm. (2010), 394(1-2):122-142.
Kojima et al., Synthesis of polyamidoamine dendrimers having poly(ethylene glycol) grafts and their ability to encapsulate anticancer drugs, Bioconjug. Chem. (2000), 11(6):910-917.
Lee et al., Synthesis of Novel Biodegradable Cationic Dendrimers, Macromolecular Rapid Communications (2006), 27(18):1608-1614.
Lim et al., Gadolinium MRI contrast agents based on triazine dendrimers: relaxivity and in vivo pharmacokinetics, Bioconjug. Chem. (2012), 23(11):2291-2299.
McCarthy et al., Dendrimers as drugs: discovery and preclinical and clinical development of dendrimer-based microbicides for HIV and STI prevention, Mol. Pharm. (2005), 2(4):312-318.
Medina et al., Dendrimers as carriers for delivery of chemotherapeutic agents, Chem. Rev. (2009), 109(7):3141-3157.

(Continued)

*Primary Examiner* — Timothy Thomas
*Assistant Examiner* — Andrew S Rosenthal
(74) *Attorney, Agent, or Firm* — Glenn J. Foulds; Carol L. Francis; Bozicevic, Field & Francis LLP

(57) ABSTRACT

This invention relates to certain dendrimer compounds. In particular, this invention relates to novel dendrimer compounds that can be elaborated to give increasingly large and complex compounds. These elaborated compounds can be attached to, or can encapsulate within, active agent(s) so as to beneficially modify the characteristics of that active agent. Alternatively, the elaborated compounds can themselves be beneficially modified into therapeutic agents by the attachment of inactive agents.

20 Claims, No Drawings

(56) References Cited

OTHER PUBLICATIONS

Menjoge et al., Dendrimer-based drug and imaging conjugates: design considerations for nanomedical applications, Drug Discov. Today (2010), 15(5-6):171-185.

Morgan et al., Dendrimer-encapsulated camptothecins: increased solubility, cellular uptake, and cellular retention affords enhanced anticancer activity in vitro, Cancer Res. (2006), 66(24):11913-11921.

Mucalo et al., Melt-extruded polyethylene oxide (PEO) rods as drug delivery vehicles: Formulation, performance as controlled release devices and the influence of co-extruded excipients on drug release profiles, Chemistry in New Zealand (2012), 76(3):85-95.

Mullen et al., Best practices for purification and characterization of PAMAM dendrimer, Macromolecules (2012), 45(12):5316-5320.

Negm et al., Influence of structure of the cationic poly-triethanolammonium bromide derivatives. II. corrosion inhibition, Egypt. J. Chem. (2005), 48(2):201-210.

Negm et al., Influence of structure on the cationic polytriethanolammonium bromide derivatives. I. Synthesis, surface and thermodynamic properties, Egypt. J. Chem. (2004), 47(4):369-381.

Reymond et al., Peptide and glycopeptide dendrimer apple trees as enzyme models and for biomedical applications, Org. Biomol. Chem. (2012), 10(8):1483-1492.

Risch, Encapsulation: Overview of Uses and Techniques, Encapsulation and Controlled Release of Food Ingredients (1995), Chapter 1; p. 2-7; ACS Symposium Series; American Chemical Society: Washington, DC.

Röglin et al., A synthetic "tour de force": well-defined multivalent and multimodal dendritic structures for biomedical applications, Angew. Chem. Int. Ed. Engl. (2011), 50(1):102-112.

Rupp et al., VivaGel™ (SPL7013 Gel): A candidate dendrimer—microbicide for the prevention of HIV and HSV infection, Int. J. Nanomedicine (2007), 2(4): 561-566.

Teo et al., Preventing acute gut wall damage in infectious diarrhoeas with glycosylated dendrimers, EMBO Mol. Med. (2012), 4(9):866-881.

Tomalia et al., Discovery of dendrimers and dendritic polymers: a brief historical perspective, J. Polym. Sci. Part A: Polym. Chem. (2002), 40(16):2719-2728.

Zanini et al., Novel Dendritic alpha-Sialosides: Synthesis of Glycodendrimers Based on a 3,3'-Iminobis(propylamine) Core, J. Org. Chem. (1996), 61(21):7348-7354.

\* cited by examiner

DENDRIMER SCAFFOLDS FOR PHARMACEUTICAL USE

FIELD OF INVENTION

This invention relates to certain dendrimer compounds. In particular, this invention relates to novel dendrimer compounds that can be elaborated to give increasingly large and complex compounds. These elaborated compounds can be attached to, or can encapsulate within, active agent(s) so as to beneficially modify the characteristics of that active agent. Alternatively, the elaborated compounds can themselves be beneficially modified into therapeutic agents by the attachment of inactive agents.

BACKGROUND

Dendrimers are large, branched molecules which are members of a versatile, fourth class of polymer architecture (i.e. dendritic polymers after traditional linear, cross-linked and branched types) (Tomalia 2002). Typically, dendrimers have well-defined scaffolding and are conjugated to, complexed with or used to encapsulate therapeutic drugs or imaging moieties (Menjoge 2010, Röglin 2011).

Dendrimers have properties that are of interest to the pharmaceutical industry, particularly their size and multi-valency. For example, US2009/0036353 A1 relates to insulin conjugated with structurally well-defined dendrimers which have glycerol units at the branching points. Zanini and Roy (Zanini 1996) describe the design and synthesis of symmetrical glycodendrimers with even valencies from 2 to 16, which are built on glycine as the branching point and which end with equidistant thiosialoside residues. The synthetic strategy employed allowed for the incorporation of different carbohydrate haptens into the prebuilt dendritic structures. The branched molecules described by Negm and Hafiz (Negm 2004, 2005; Hafiz 2005) have charged quaternary tetra-alkylated nitrogens within the structure and can be used as antimicrobial agents and for nucleic acid delivery into cells.

The above examples focus on the use of dendrimers as drug delivery vehicles or diagnostic tools. However, dendrimers may also be used as drugs in their own right. For example, the dendrimer SPL7013 is a vaginal microbicide (McCarthy 2005) which has been developed to prevent the transmission of sexually transmitted infections and to treat bacterial vaginosis.

The encapsulation of imaging agents and therapeutic agents into dendrimer compounds has also been the subject of increasing research. Morgan (2006) showed that the anticancer drug camptothecin could be encapsulated in a biocompatible polyester dendrimer and Boisselier (2010) shows that vitamins could be encapsulated in both di-aminobutane (DAB) and PAMAM dendrimers. Polypropyleneimines (PPI dendrimers) functionalised by glycerol-based entities have also been examined for the encapsulation of MRI contrast reagents to improve relaxivitiy times (Balieu 2012).

A recent review on dendrimer based products (Menjoge 2010) demonstrates the applicability of dendrimers in a commercial setting. Dendrimers have been successfully used in the commercial market for diagnostics, for example the SuperFect transfection reagent marketed by Qiagen that utilises a PAMAM dendrimer.

In the pharmaceutical and imaging arena, however, only a few products have entered into clinical trials, most notably Starpharma's VivaGel™ and Schering-Plough's Gadomer-17 MRI contrast agent that both contain poly-lysine dendrimeric cores. For dendrimers to be of use as therapeutic drugs, they must have low toxicity with a suitable, known safe dosing window; high stability with measurable degradation, producing degradants of low toxicity; low cost of goods and to be able to be made by an efficient, scalable synthesis; high, HPLC measurable purity; suitable solubility in biologically relevant media; and must have amine or carboxylic acid termini available for further modification by subsequent capping reactions. This is a challenging set of criteria that most existing dendrimer constructs fail.

It is therefore the object of this invention to provide novel dendrimer compounds that adequately address the above criteria and in particular, elaborated dendrimer compounds to which active and/or inactive agent(s) can be attached to, and/or encapsulated within.

STATEMENTS OF INVENTION

In a first aspect, the invention provides compounds of formula (I):

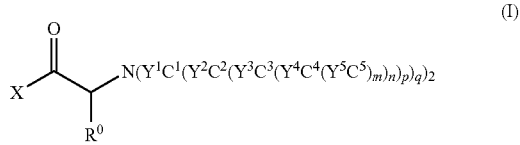

or salts thereof, wherein:
$Y^1, Y^2, Y^3, Y^4$ or $Y^5$ are

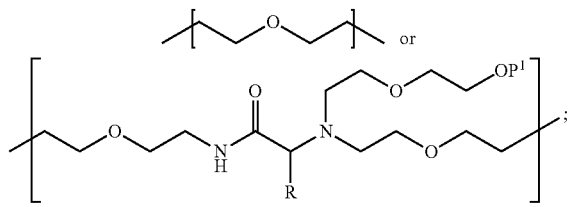

$m=n=p=q=2$; or $m=0$ and $n=p=q=2$; or $m=n=0$ and $p=q=2$; or $m=n=p=0$ and $q=2$; or $m=n=p=q=0$, wherein:
when $q=2$, $C^1$ is

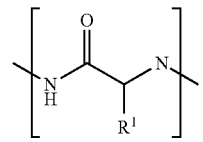

when $q=0$, $C^1$ is $NHP^2$ or $N(CH_2CO_2P^4)_2$ or $NHCOCH_3$ or

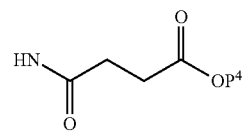

when p=2, $C^2$ is

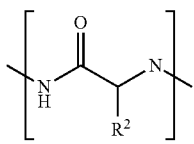

when p=0, $C^2$ is $NHP^2$ or $N(CH_2CO_2P^4)_2$ or $NHCOCH_3$ or

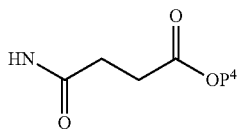

when n=2, $C^3$ is

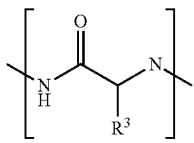

when n=0, $C^3$ is $NHP^2$ or $N(CH_2CO_2P^4)_2$ or $NHCOCH_3$ or

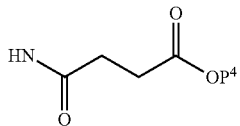

when m=2, $C^5$ is $NHP^2$ or $N(CH_2CO_2P^4)_2$ or $NHCOCH_3$ or

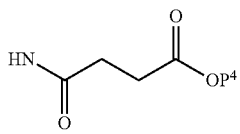

and $C^4$ is

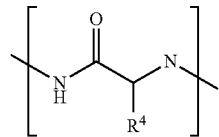

when m=0, $C^4$ is $NHP^2$ or $N(CH_2CO_2P^4)_2$ or $NHCOCH_3$ or

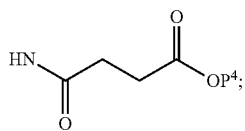

R, $R^0$, $R^1$, $R^2$, $R^3$ and $R^4$ are H or the side chain of a natural amino acid (except proline);
$P^1$ is H or a hydroxy protecting group;
$P^2$ is H or an amino protecting group;
$P^4$ is H or a carboxylic acid protecting group;
X is a leaving group or $OP^3$ or

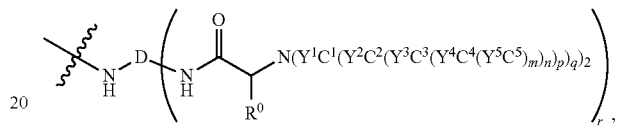

wherein $P^3$ is H or a carboxylic acid protecting group;
wherein:
  each of $Y^1$, $Y^2$, $Y^3$, $Y^4$, $Y^5$, $C^1$, $C^2$, $C^3$, $C^4$, $C^5$ are as previously defined and can be the same or different;
  m, n, p and q are as previously defined and can be the same or different;
  R, $R^0$, $R^1$, $R^2$, $R^3$ and $R^4$ are as previously defined and can be the same or different;
  r is 1, 2, or 3; and
  D is an aryl; or a straight-, branched- or cyclo-alkyl moiety, or

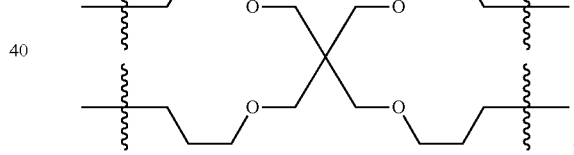

Preferably $P^1$ is selected from H, acetate, substituted acetate, benzoate, trialkylsilyl or allyl or benzyl.
Preferably $P^1$ is H.
Preferably $P^2$ is Boc, Fmoc or Cbz.
Preferably $P^2$ is

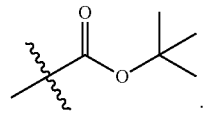 [SMILES: *C(=O)OC(C)(C)C]

Preferably $P^4$ is tert-butyl or benzyl.
Preferably $P^4$ is H.
Preferably R, $R^0$, $R^1$, $R^2$, $R^3$ and $R^4$ are H, —$(CH_2)_4NH_2$ or —$(CH_2)_3NHC$=$NHNH_2$ or —$CH(CH_3)CH_2CH_3$ or —$CH_2Ph$ or —$CH_2CH(CH_3)_2$ or —$CH_3$, or —$(CH_2)_2SCH_3$, or $CH_2CO_2H$ or —$(CH_2)_2CO_2H$ or —$CH(OH)CH_3$ or $(CH_2)_2CONH_2$ or $CH_2OH$ or $CH_2SH$ or $CH_2CONH_2$ or —$CH(CH_3)_2$ or

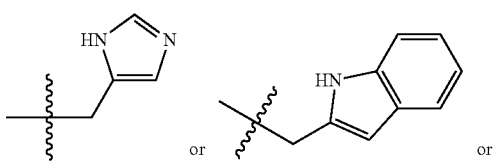 or 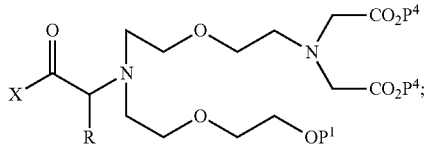 or

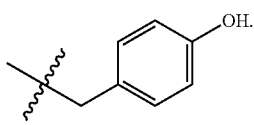

Preferably R, $R^0$, $R^1$, $R^2$, $R^3$ and $R^4$ are H.

Preferably, the compounds of formula (I) are neutral salts or salts of chloride, bromide, trifluoroacetate, p-toluenesulfonate, acetate, sulfate, hydrogen sulfate, carbonate, hydrogen carbonate, phosphate, hydrogen phosphate, triethylammonium, ammonium, or pyridinium.

Preferably X is a leaving group or $OP^3$, wherein $P^3$ is as defined above.

Preferably $P^3$ is alkyl or aralkyl.

Preferably $P^3$ is benzyl.

Preferably X is OH.

Preferably, the compounds of formula (I) are made by coupling together any one or more the following building blocks:

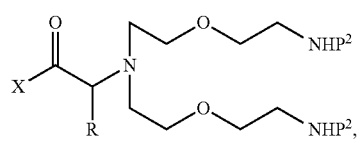 A

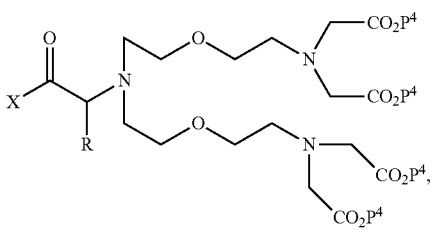 B

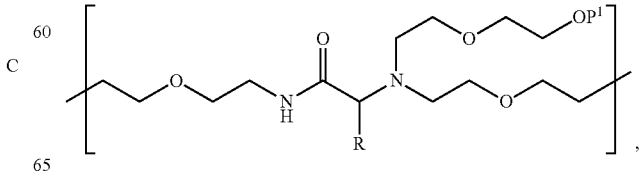 , and

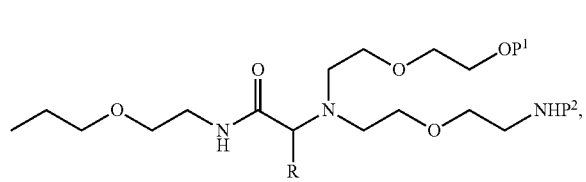 D wherein:
$P^1$ is as defined above;
$P^2$ is as defined above;
X is a leaving group or $OP^3$, wherein $P^3$ is as defined above;
$P^4$ is as defined above; and
R is as defined above.

Preferably, any one of more of building blocks A to D are linked by the following building block:

$(NHP^2)_s$-D-$(NH_2)_r$E;

wherein:
D is as defined above; and
r is as defined above; and
s is 1, 2 or 3 such that s+r equals 2, 3 or 4.

Preferably, D is a straight chain alkyl.

Preferably, $C^1$, $C^2$, $C^3$, $C^4$ or $C^5$ is a terminal group and is $N(CH_2CO_2P^4)_2$, wherein $P^4$ is as previously defined.

Preferably, $Y^1C^1$, $Y^2C^2$, $Y^3C^3$, $Y^4C^4$ or $Y^5C^5$ is a terminal group and is wherein $P^1$ and $P^4$ are as previously defined.

Preferably, $Y^1C^1$, $Y^2C^2$, $Y^3C^3$, $Y^4C^4$ or $Y^5C^5$ is a terminal group and is wherein $P^1$ and $P^2$ are as previously defined.

Preferably, building blocks B, C or D form an outer generation of the compound of formula (I).

Preferably, $Y^1$, $Y^2$, $Y^3$, $Y^4$ or $Y^5$ are wherein $P^1$ is as previously defined.

Preferably, the compound of formula (I) is:
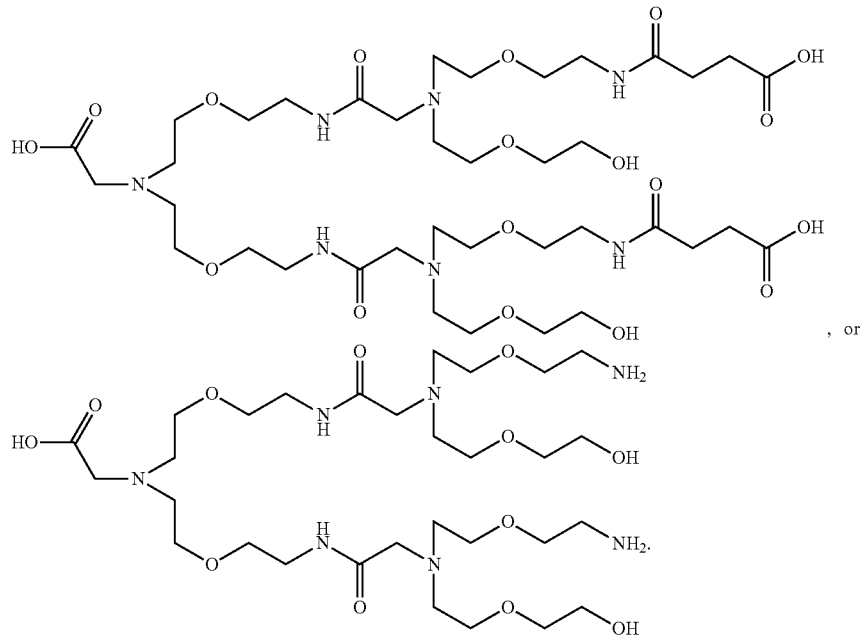
, or
Alternatively, the compound of formula (I) is made by coupling together two or more units of building block A.
Preferably, the compounds of formula (I) comprising building block A are selected from the following:
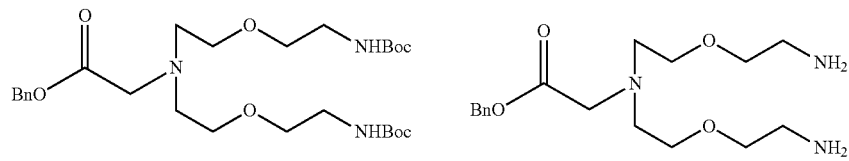
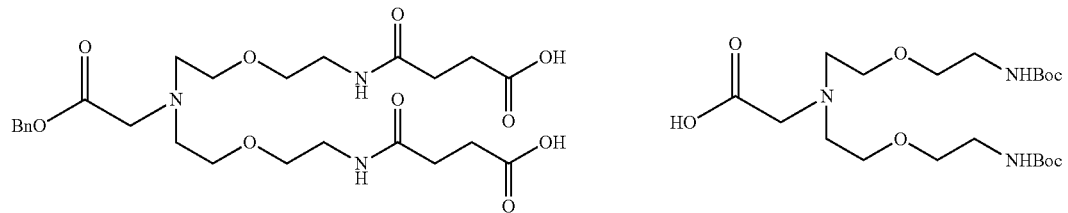
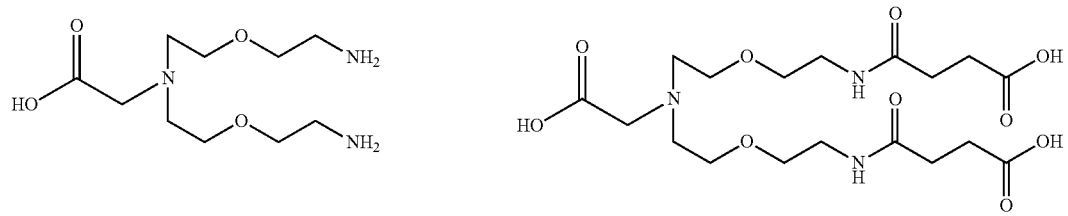

-continued
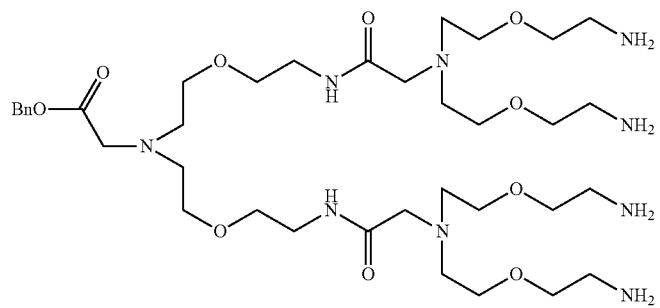
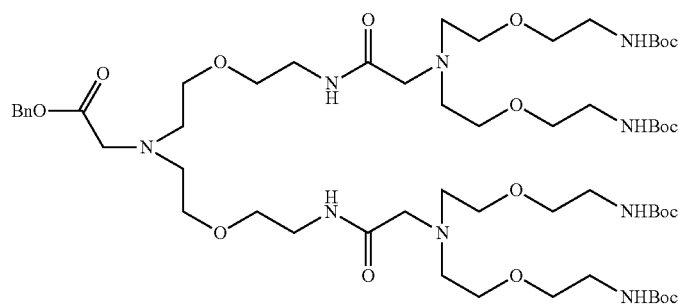
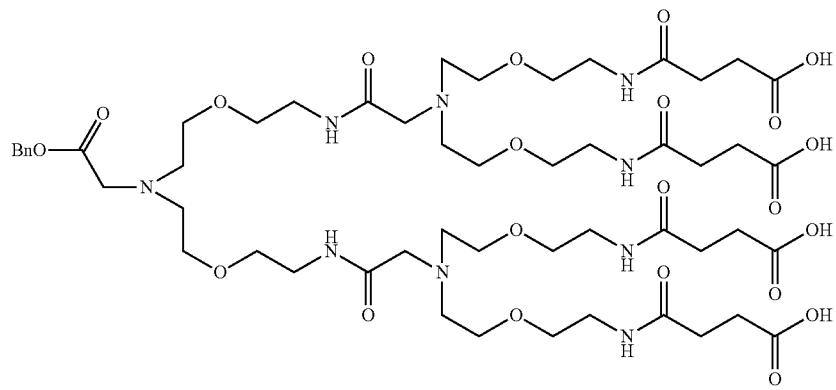
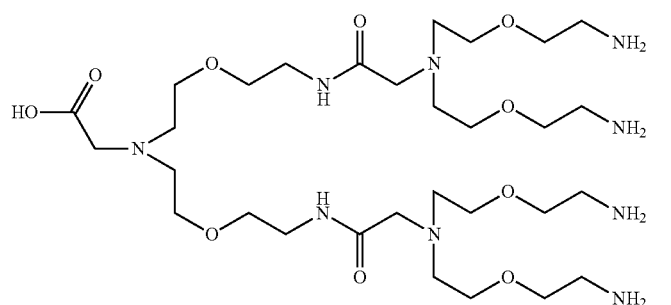
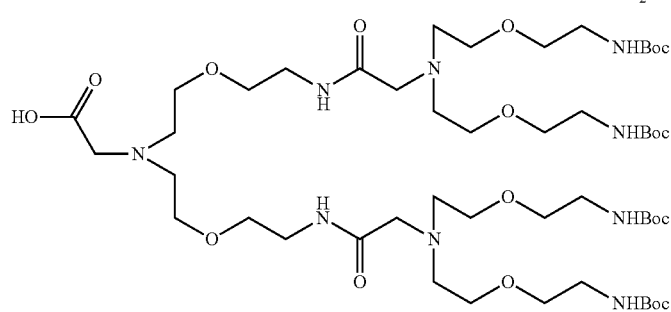

-continued
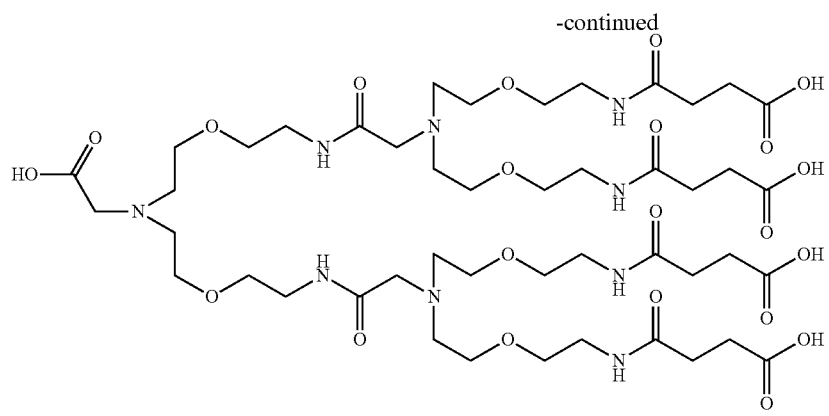
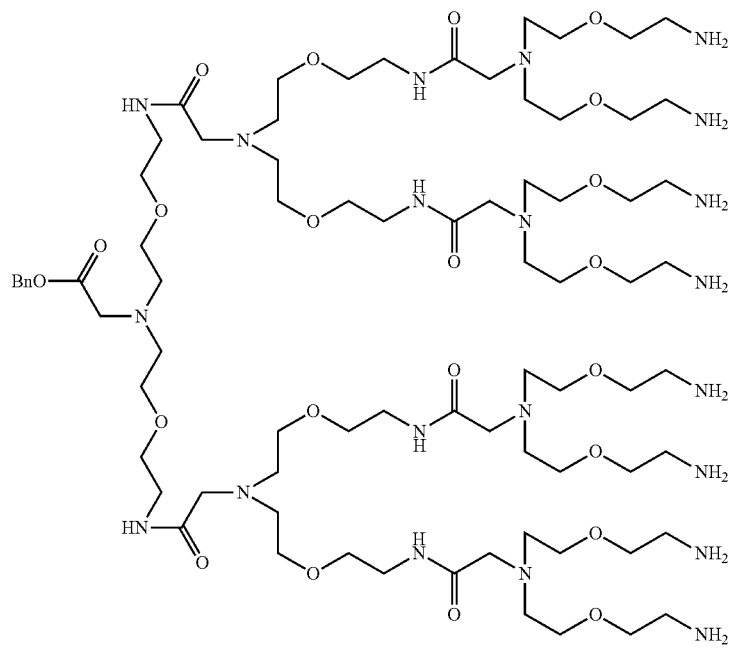
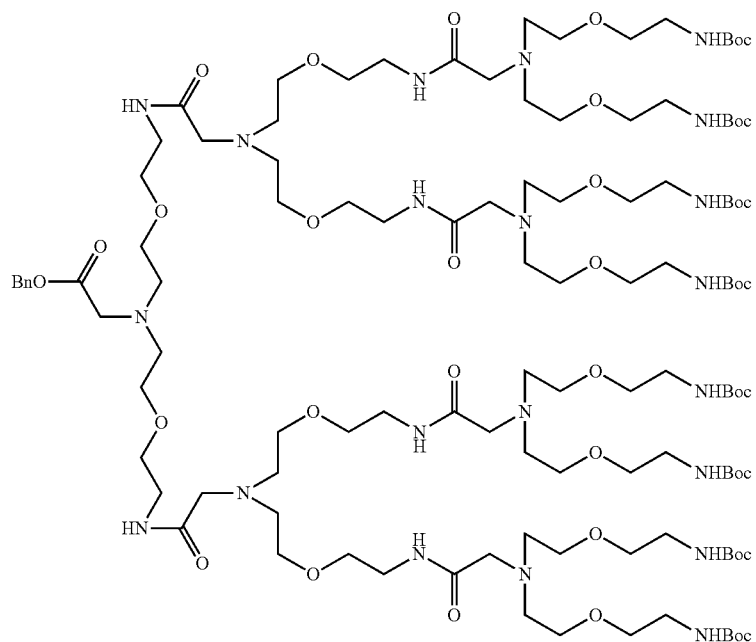

-continued
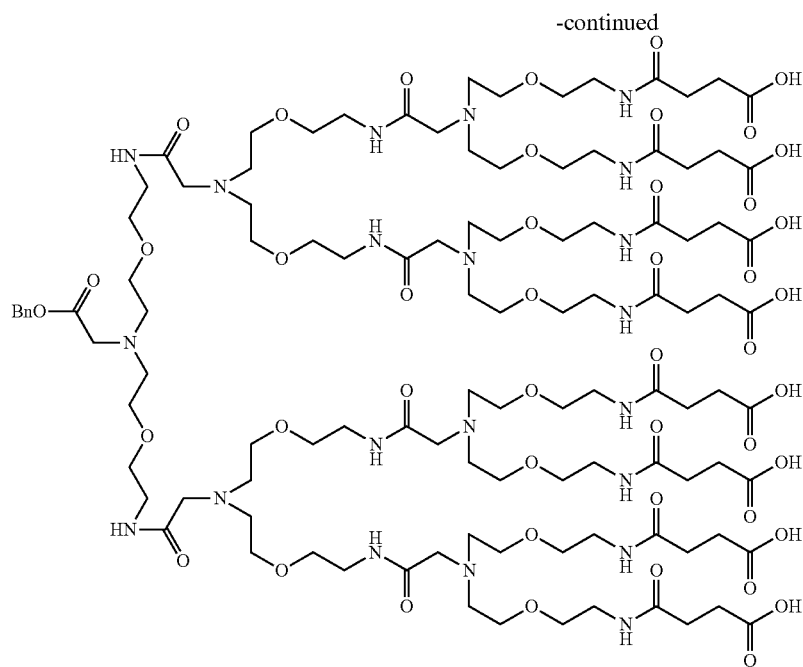
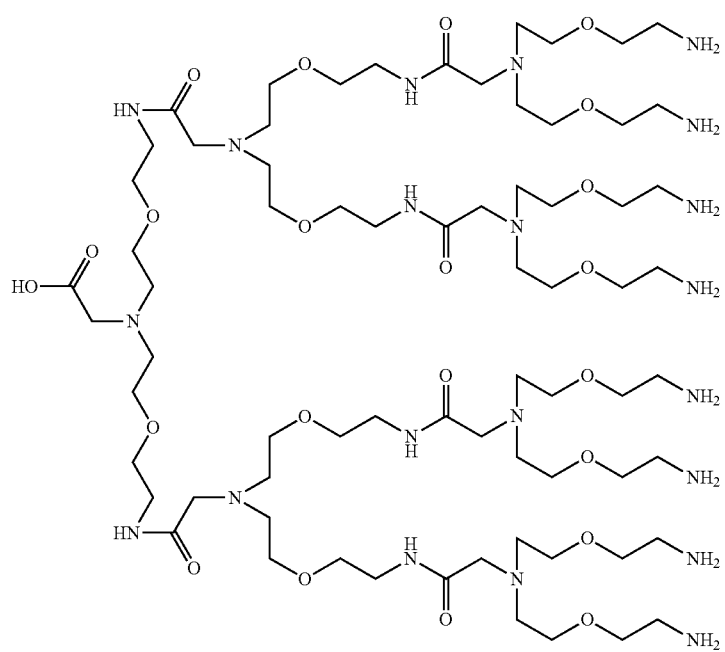

-continued
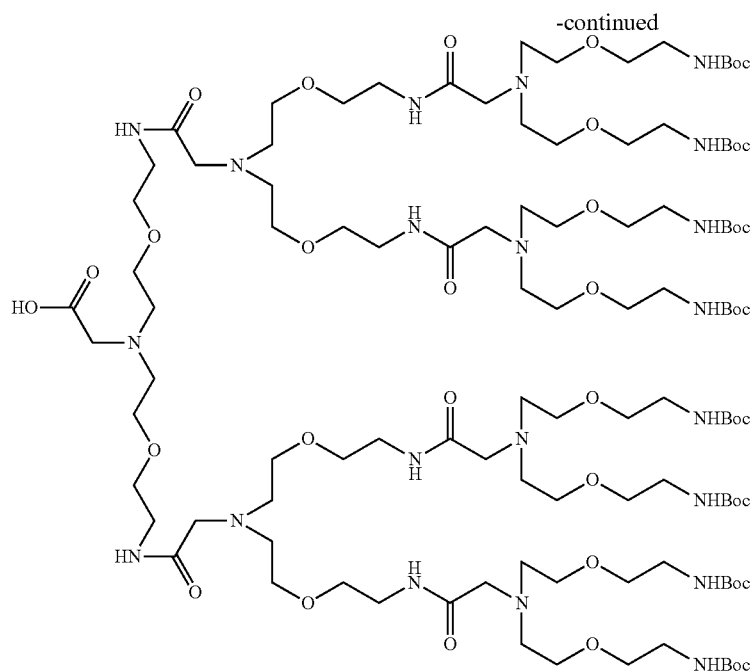
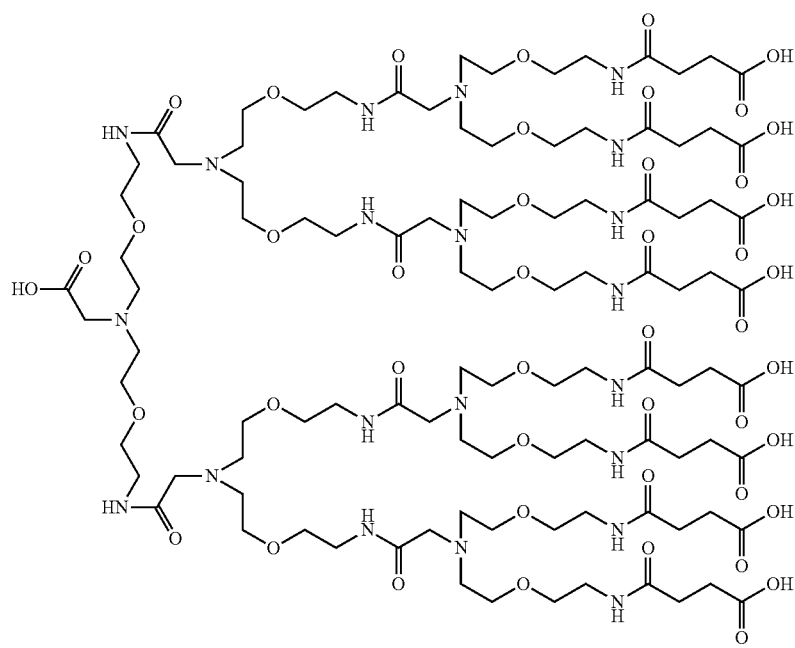

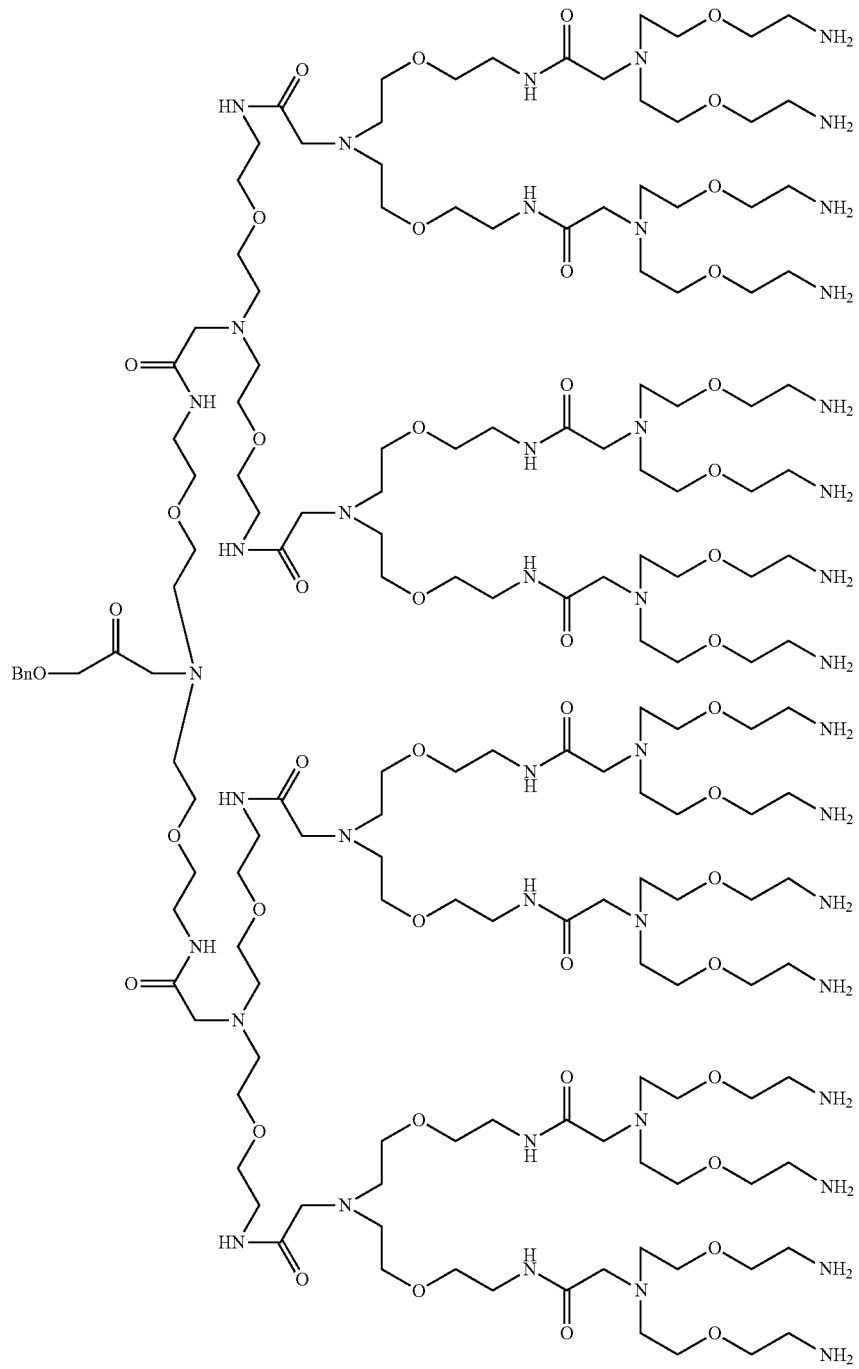 [SMILES: NCCOCCN(CCOCCN)CC(=O)NCCOCCN(CCOCCNC(=O)CN(CCOCCN)CCOCCN)CC(=O)NCCOCCN(CCOCCNC(=O)CN(CCOCCNC(=O)CN(CCOCCN)CCOCCN)CCOCCNC(=O)CN(CCOCCN)CCOCCN)CC(=O)NCCOCCN(CCOCCNC(=O)CN(CCOCCNC(=O)CN(CCOCCNC(=O)CN(CCOCCN)CCOCCN)CCOCCNC(=O)CN(CCOCCN)CCOCCN)CCOCCNC(=O)CN(CCOCCNC(=O)CN(CCOCCN)CCOCCN)CCOCCNC(=O)CN(CCOCCN)CCOCCN)CC(=O)COCc1ccccc1]

-continued
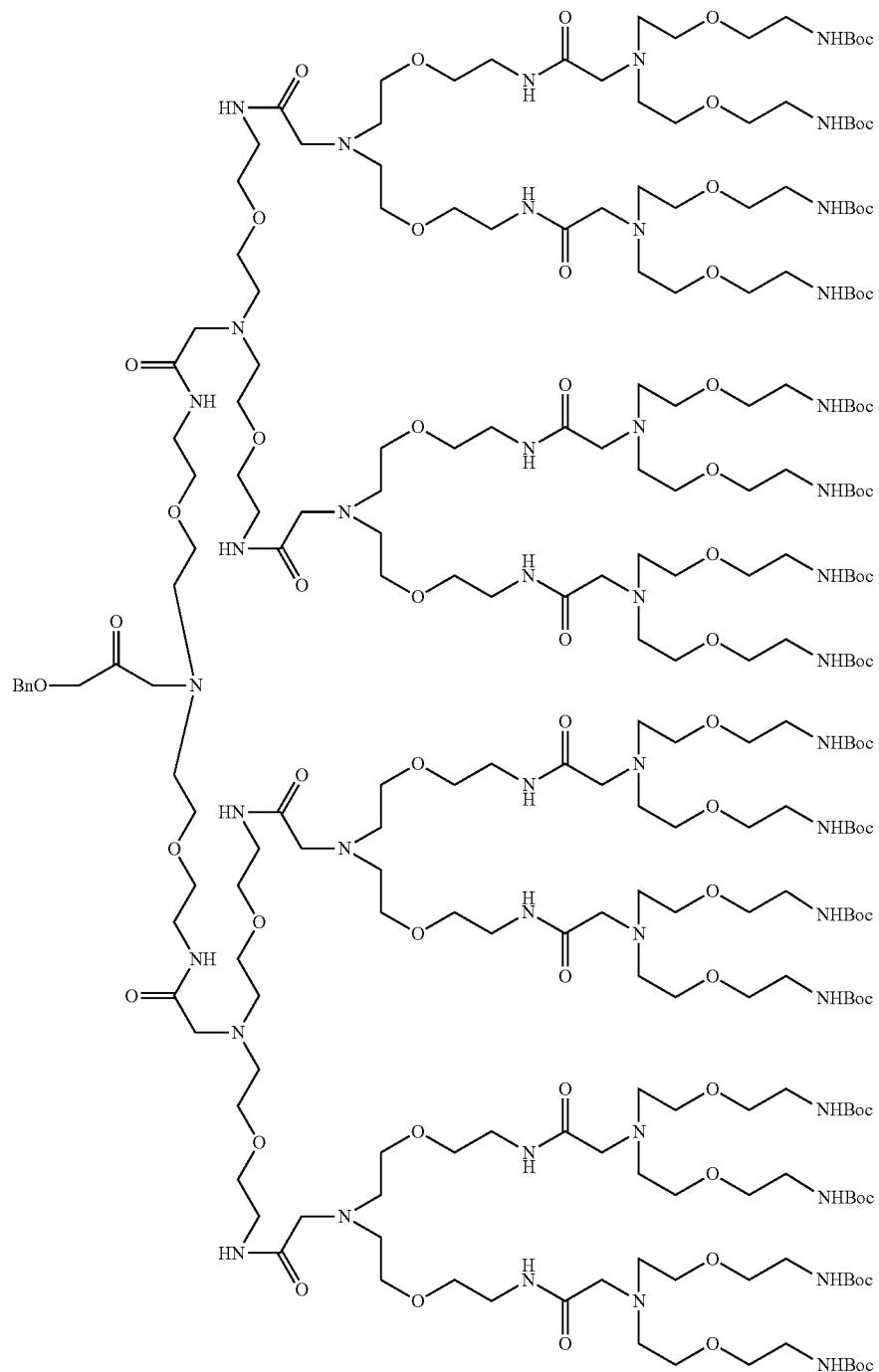

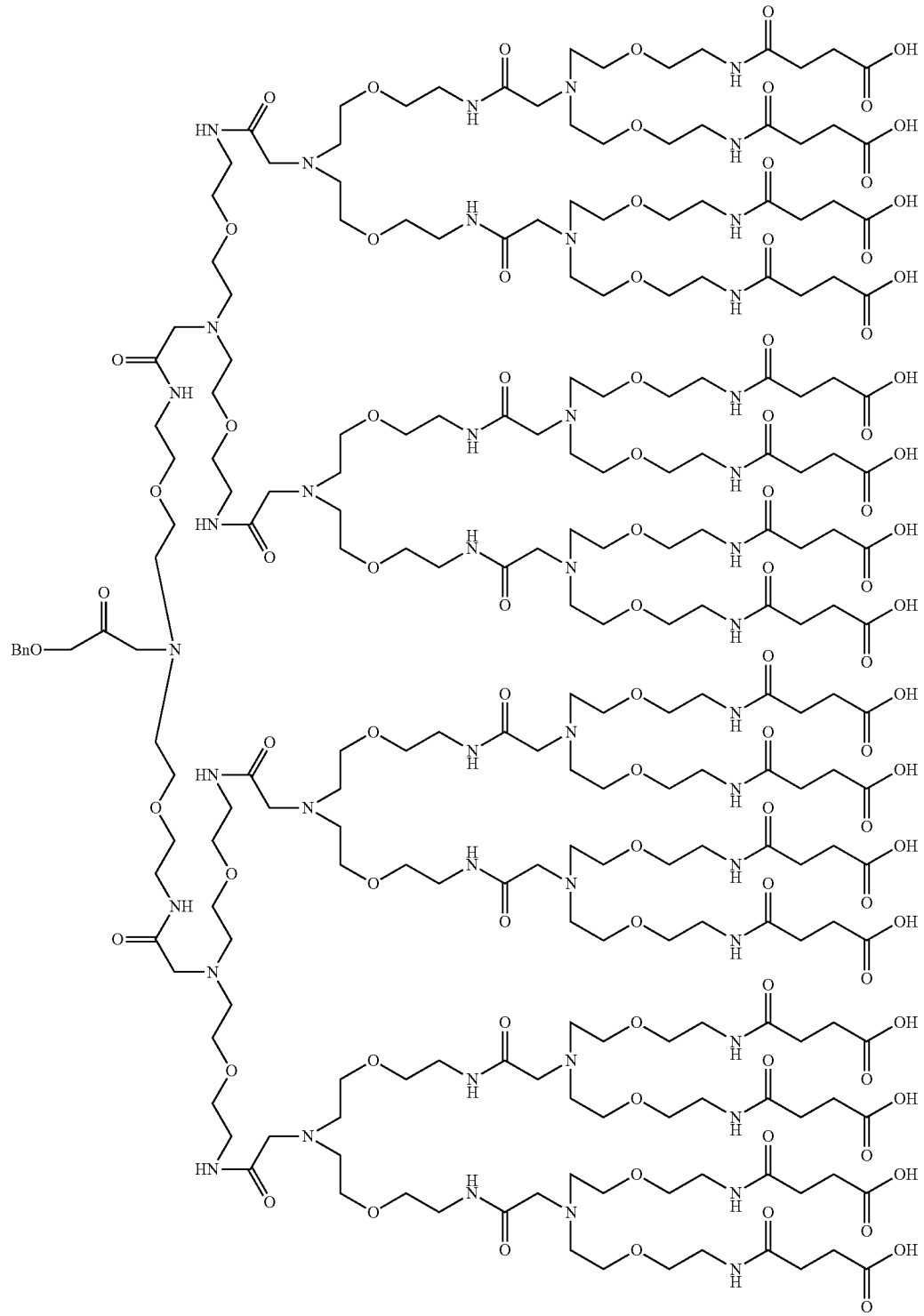

-continued
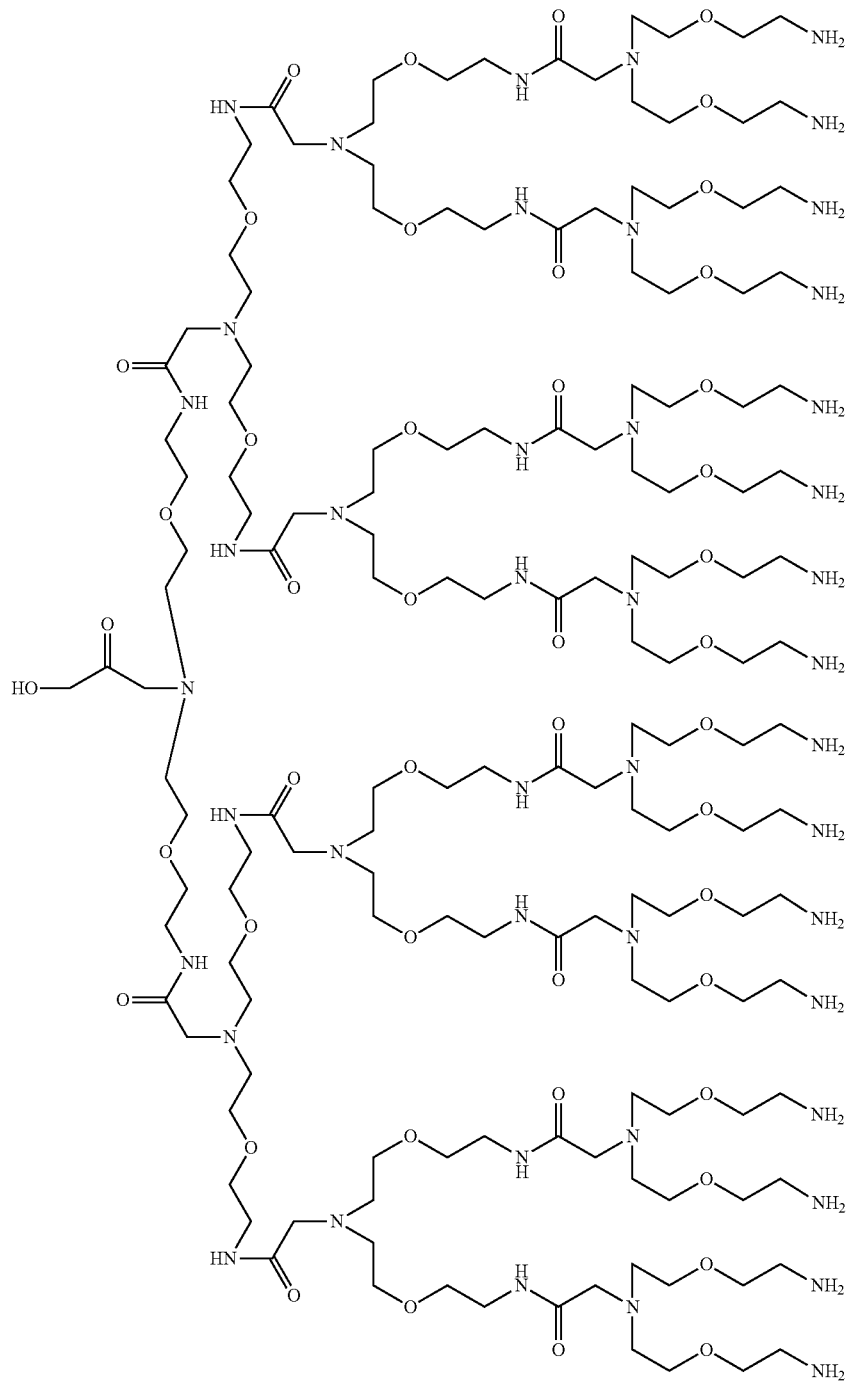 [SMILES: NCCOCCN(CCOCCN)CC(=O)NCCOCCN(CCOCCNC(=O)CN(CCOCCN)CCOCCN)CC(=O)NCCOCCN(CCOCCNC(=O)CN(CCOCCNC(=O)CN(CCOCCN)CCOCCN)CCOCCNC(=O)CN(CCOCCN)CCOCCN)CC(=O)NCCOCCN(CCOCCNC(=O)CN(CCOCCNC(=O)CN(CCOCCNC(=O)CN(CCOCCN)CCOCCN)CCOCCNC(=O)CN(CCOCCN)CCOCCN)CCOCCNC(=O)CN(CCOCCNC(=O)CN(CCOCCN)CCOCCN)CCOCCNC(=O)CN(CCOCCN)CCOCCN)CC(=O)CO]

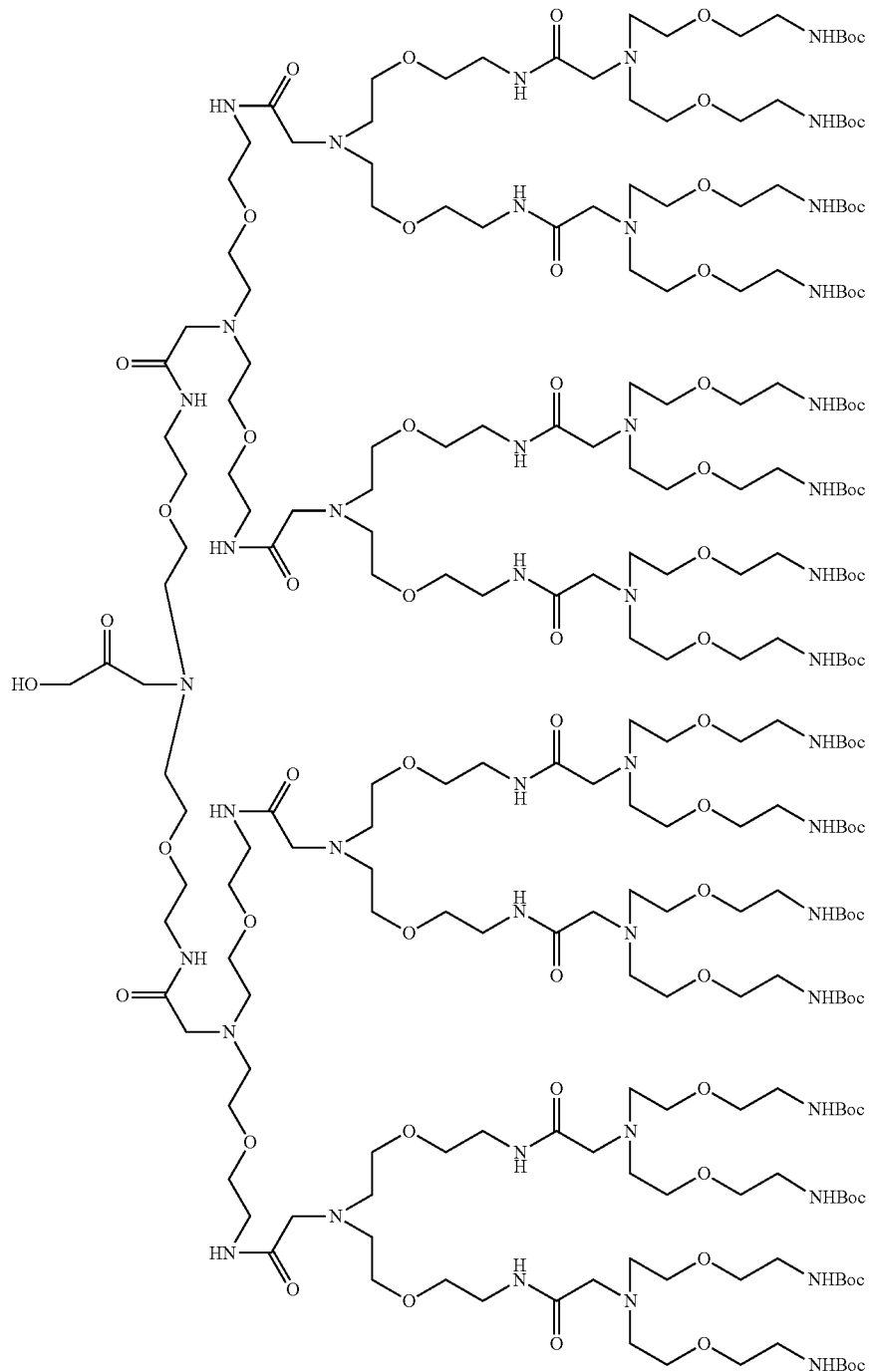

-continued
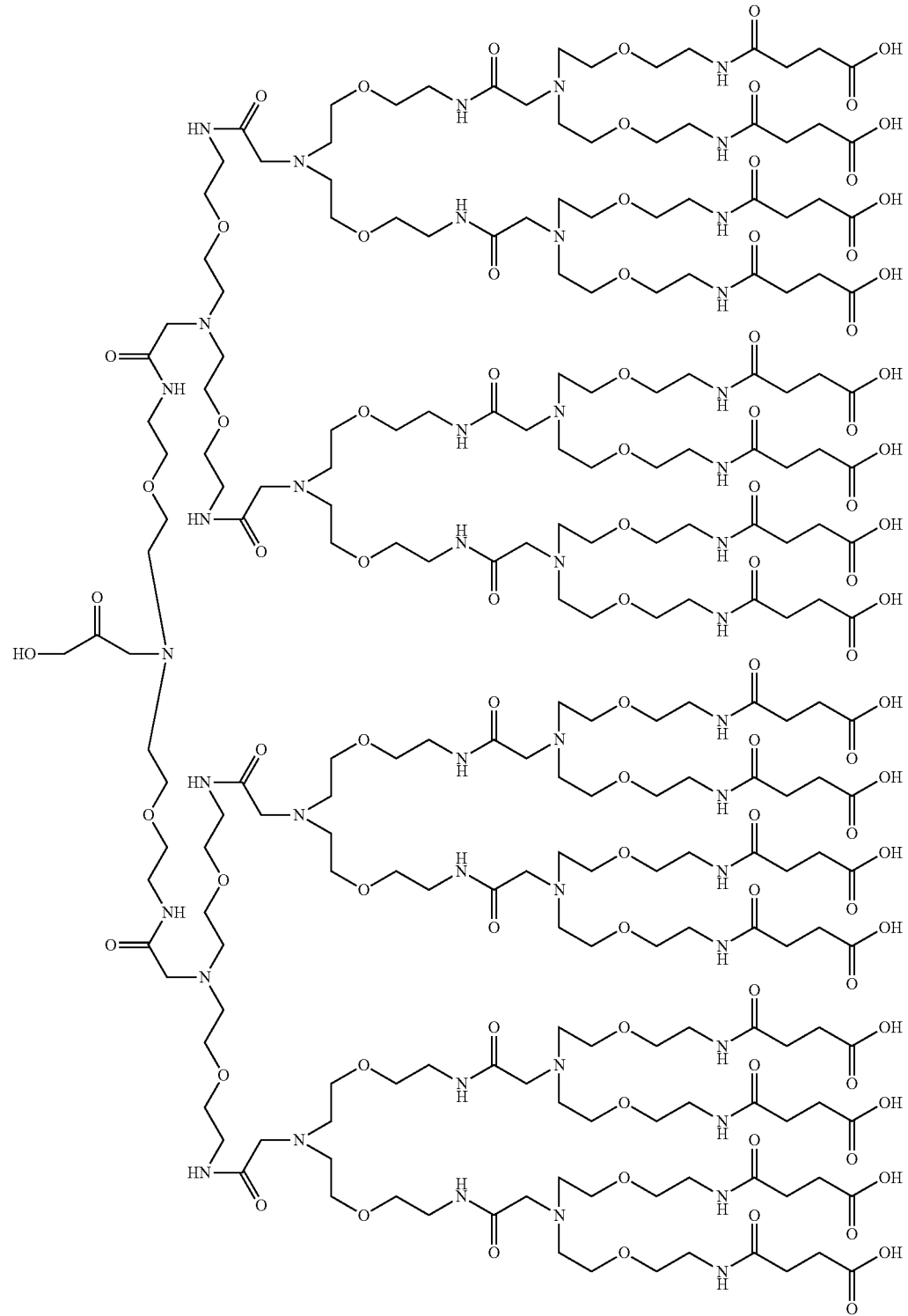

-continued
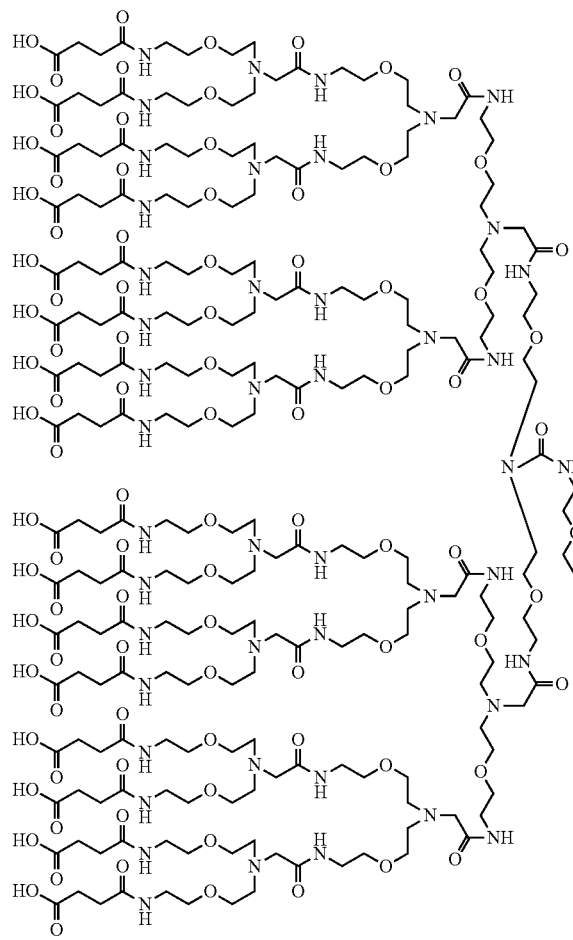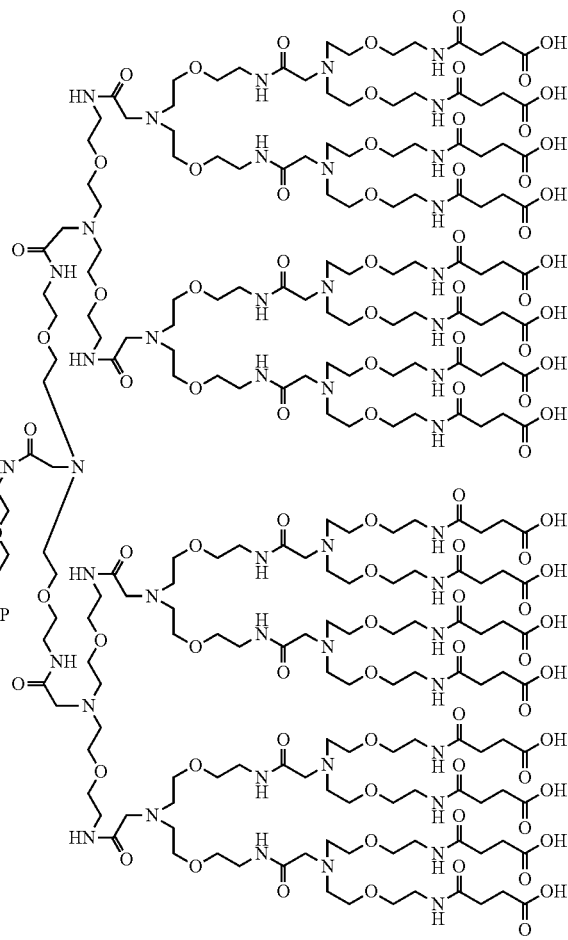
P = H or Bn

-continued
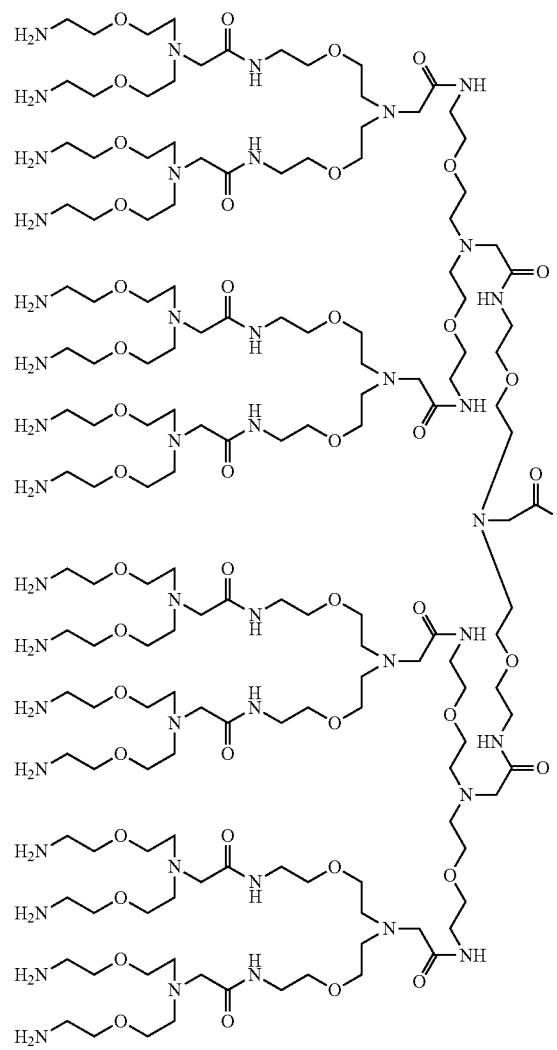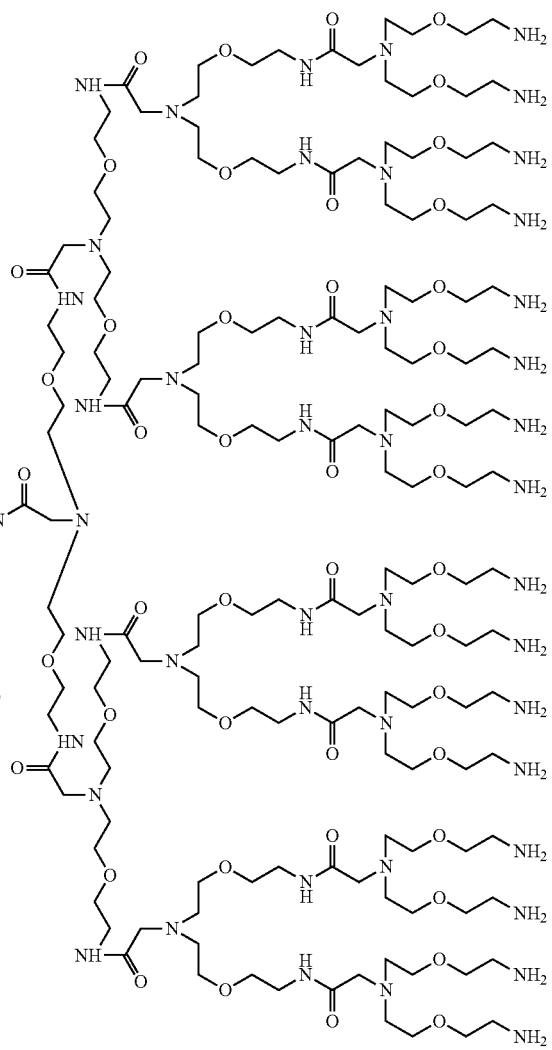
P = H or Bn

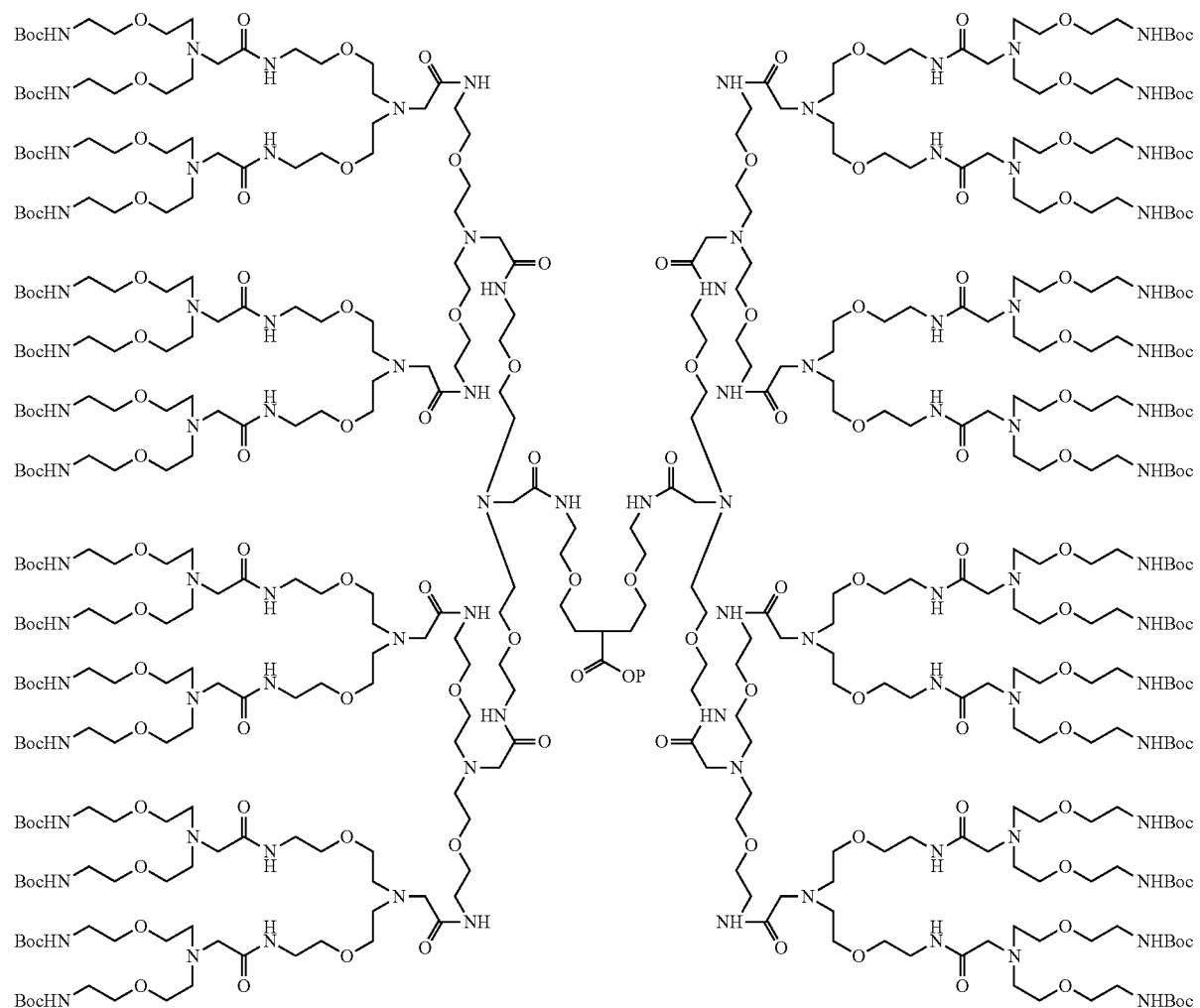
P = H or Bn wherein:
any one or more of the NH$_2$ groups may be replaced with NHP$^2$ (as defined previously); and
any one or more of the hydrogen atoms of the terminal carboxylic acid groups may be replaced with P$^3$ (as defined previously).
Alternatively, Y is

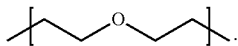

Preferably, the compound of formula (I) is:

Preferably, the active agents are covalently attached directly or by a linker to amide or ester linkages to compounds of formula (I) or are encapsulated by non-covalent interactions.

Preferably, the active agents include therapeutic agents or imaging agents.

Preferably, the therapeutic agents include anti-cancer agents, analgesic agents, anti-inflammatory agents, targeting agents, anti-malarial drugs, antibiotics including penicillins, sulfonamides, macrolides, tetracyclines, quinolones, cephalosporins, aminoglycosides and glycopeptides, and anti-viral agents.

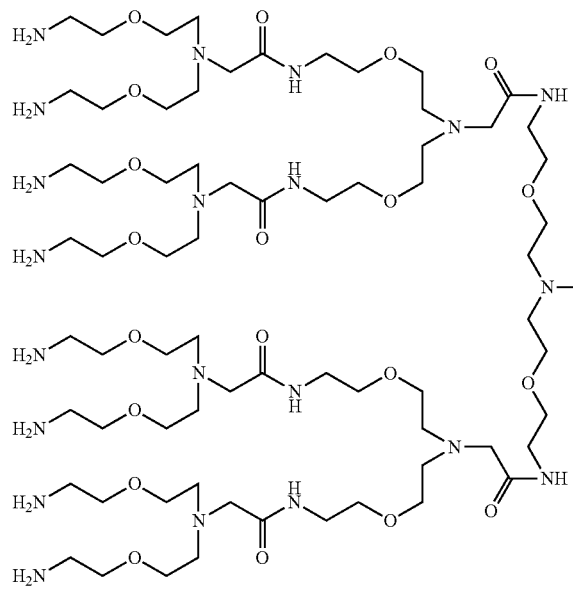 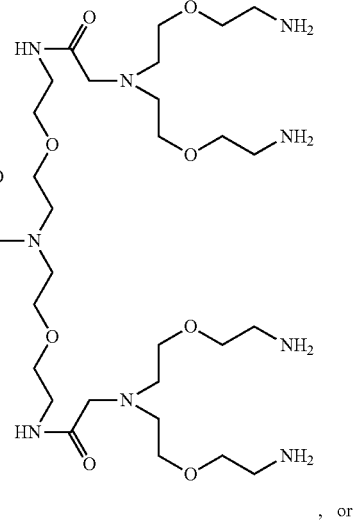

, or

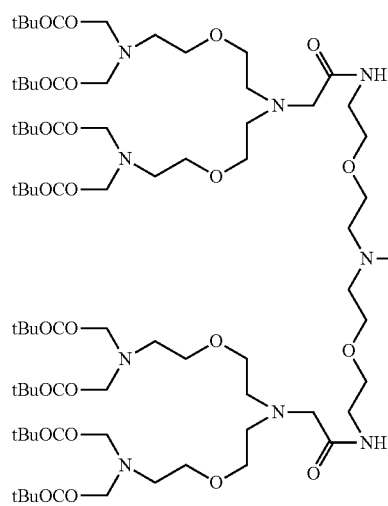 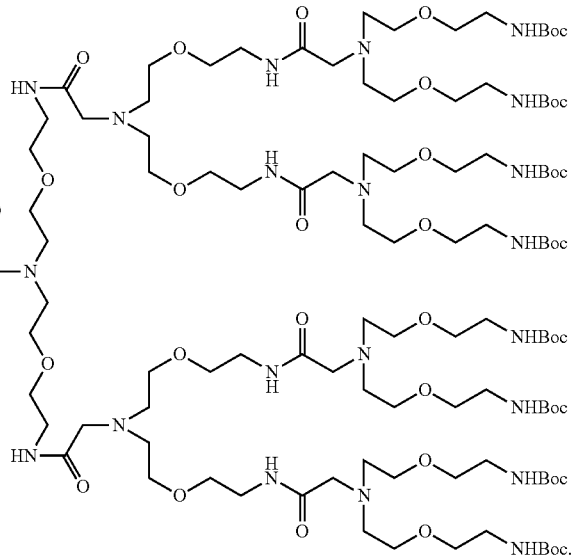

Preferably, compounds of formula (I) are suitable for use as carriers of active agents.

Preferably, the active agents are attached to, or encapsulated within the compounds of formula (I) of the present invention.

Preferably, the imaging agents include gadolinium complexes and fluorophores.

Alternatively, compounds of formula (I) may be modified into therapeutic agents by the attachment of inactive agents.

Preferably, the inactive agents include targeting agents and agents suitable for multivalent presentation.

In a second aspect, the present invention provides a method for the manufacture of a therapeutic composition, the method including the steps of adding an active agent to a dendrimer of formula (I).

Preferably, the active agent is a therapeutic agent or an imaging agent.

Preferably, the therapeutic agent is selected from anti-cancer agents, analgesic agents, anti-inflammatory agents, targeting agents, anti-malarial drugs, antibiotics including penicillins, sulfonamides, macrolides, tetracyclines, quinolones, cephalosporins, aminoglycosides and glycopeptides, and anti-viral agents.

Preferably, the imaging agent is selected from gadolinium complexes and fluorophores.

In a third aspect, the present invention includes a compound of formula (I) together with an active agent attached to, or encapsulated within, the compound of formula (I).

Preferably, the active agent is as defined above.

In a fourth aspect, the present invention includes a pharmaceutical composition comprising a compound of formula (I) together with an active agent attached to, or encapsulated within, the compound of formula (I) together with suitable carriers and/or excipients.

Preferably, the active agent is as defined above.

DETAILED DESCRIPTION

Definitions

The term "dendrimer" means a symmetrical or unsymmetrical hyperbranched molecule or macromolecule.

The term "alkyl" means any saturated hydrocarbon radical having up to 30 carbon atoms and includes any $C_1$-$C_{25}$, $C_1$-$C_{20}$, $C_1$-$C_{15}$, $C_1$-$C_{10}$, or $C_1$-$C_6$ alkyl group, and is intended to include both straight- and branched-chain- and cyclo-alkyl groups. Examples of alkyl groups include: methyl group, ethyl group, n-propyl group, iso-propyl group, n-butyl group, iso-butyl group, sec-butyl group, t-butyl group, n-pentyl group, 1,1-dimethylpropyl group, 1,2-dimethylpropyl group, 2,2-dimethylpropyl group, 1-ethylpropyl group, 2-ethylpropyl group, n-hexyl group, 1-methyl-2-ethylpropyl group, cyclopentyl group and cyclohexyl group.

The term "aryl" means an aromatic radical having 4 to 18 carbon atoms and includes heteroaromatic radicals. Examples include monocyclic groups, as well as fused groups such as bicyclic groups and tricyclic groups. Examples include phenyl group, indenyl group, 1-naphthyl group, 2-naphthyl group, azulenyl group, heptalenyl group, biphenyl group, indacenyl group, acenaphthyl group, fluorenyl group, phenalenyl group, phenanthrenyl group, anthracenyl group, cyclopentacyclooctenyl group, and benzocyclooctenyl group, pyridyl group, pyrrolyl group, pyridazinyl group, pyrimidinyl group, pyrazinyl group, triazolyl group (including a 1-H-1,2,3-triazol-1-yl and a 1-H-1,2,3-triazol-4-ylgroup), tetrazolyl group, benzotriazolyl group, pyrazolyl group, imidazolyl group, benzimidazolyl group, indolyl group, isoindolyl group, indolizinyl group, purinyl group, indazolyl group, furyl group, pyranyl group, benzofuryl group, isobenzofuryl group, thienyl group, thiazolyl group, isothiazolyl group, benzothiazolyl group, oxazolyl group, and isoxazolyl group.

The term "aralkyl" means an aryl group which is attached to an alkyl moiety, where aryl is as defined above. Examples include benzyl group.

Any aryl or aralkyl group may optionally be substituted with one or more substituents selected from the group consisting of alkyl, halogen, cyano, dialkylamino, amide (both N-linked and C-linked: —NHC(O)R and —C(O)NHR), nitro, alkoxy, acyloxy and thioalkyl.

It is to be understood that where the context requires, an alkyl or aryl group may have two, three of four groups attached.

The term "amino protecting group" means a radical that is able to be attached to an amino group for the purposes of protecting that amino group from unwanted reaction. Examples include Boc, Fmoc, Cbz and others as described (Greene 1999).

The term "hydroxy protecting group" means a radical that is able to replace the hydrogen atom of an hydroxy group for the purposes of protecting that hydroxy group from unwanted reaction. Examples include acetate, benzoate, trialkylsilyl, allyl, benzyl and others as described in Greene (1998).

The term "carboxylic acid protecting group" means a radical that is able to replace the hydrogen atom of a carboxylic acid moiety for the purposes of protecting that group from unwanted reaction. Examples include benzyl, methyl, ethyl, tert-butyl and others as described in Greene (1999).

The term "leaving group" means an atom, or group of atoms, that is displaced as a stable species. Examples include halides, mesylate, triflate, p-toluenesulfonate, p-nitrophenol, N-hydroxysuccinimide and others known to those skilled in the art.

ABBREVIATIONS

TLC Thin layer chromatography;
NMR Nuclear magnetic resonance;
TMS Tetramethylsilane;
MeCN Acetonitrile
Bn Benzyl;
Boc N-tert-Butoxycarbonyl;
Fmoc Fluorenylmethoxycarbonyl;
Cbz Benzyloxycarbonyl;
DMF N,N-Dimethylformamide;
DCM Dichloromethane;
DMSO Dimethylsulfoxide;
EA Ethyl acetate
NHS N-Hydroxysuccinimide;
HBTU N,N,N',N'-Tetramethyl-O-(1H-benzotriazol-1-yl) uroniumhexafluorophosphate;
DIPEA N,N-Diisopropylethylamine;
tBu tert-butyl;
THF Tetrahydrofuran;
TsOH p-Toluenesulfonic acid
pyr Pyridine;
TsOH.Gly-OBn Benzyl glycinate p-toluenesulfonate;
TsOH.Ala-OBn Benzyl alanate p-toluenesulfonate;
L Any leaving group.

General

The present invention relates to certain dendrimer compounds which can be elaborated to provide increasingly large and complex dendrimer compounds. These elaborated compounds can be attached to, or used to encapsulate, active agent(s) so as to beneficially modify the characteristics of that active agent. The elaborated dendrimers of the present invention therefore provide a scaffold or tool which may act as a carrier for various active agents. Alternatively, the elaborated compounds can themselves be beneficially modified into active agents by the attachment, or encapsulation of inactive agents.

In a first aspect, the invention provides compounds of formula (I):

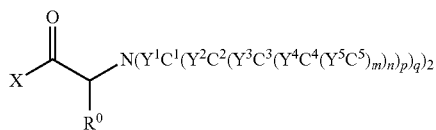  (I)

or salts thereof, wherein:
$Y^1, Y^2, Y^3, Y^4$ or $Y^5$ are

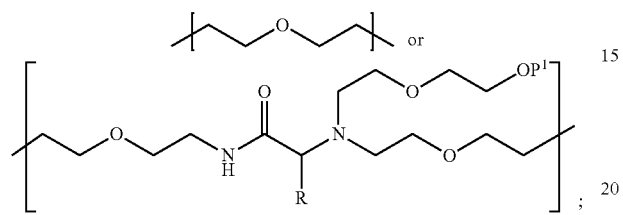

$m=n=p=q=2$; or $m=0$ and $n=p=q=2$; or $m=n=0$ and $p=q=2$; or $m=n=p=0$ and $q=2$; or $m=n=p=q=0$,
wherein:
when $q=2$, $C^1$ is

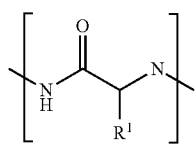

when $q=0$, $C^1$ is $NHP^2$ or $N(CH_2CO_2P^4)_2$ or $NHCOCH_3$ or

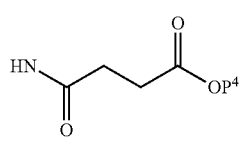

when $p=2$, $C^2$ is

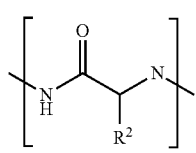

when $p=0$, $C^2$ is $NHP^2$ or $N(CH_2CO_2P^4)_2$ or $NHCOCH_3$ or

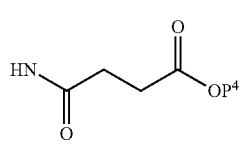

when $n=2$, $C^3$ is

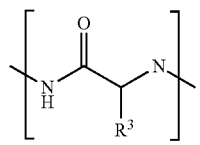

when $n=0$, $C^3$ is $NHP^2$ or $N(CH_2CO_2P^4)_2$ or $NHCOCH_3$ or

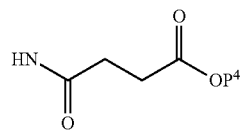

when $m=2$, $C^5$ is $NHP^2$ or $N(CH_2CO_2P^4)_2$ or $NHCOCH_3$ or

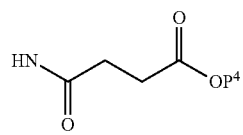

and $C^4$ is

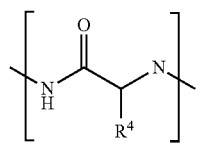

when $m=0$, $C^4$ is $NHP^2$ or $N(CH_2CO_2P^4)_2$ or $NHCOCH_3$ or

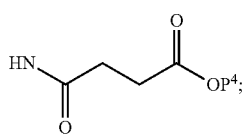

$R, R^0, R^1, R^2, R^3$ and $R^4$ are H or the side chain of a natural amino acid (except proline);
$P^1$ is H or a hydroxy protecting group;
$P^2$ is H or an amino protecting group;
$P^4$ is H or a carboxylic acid protecting group;
X is a leaving group or $OP^3$ or

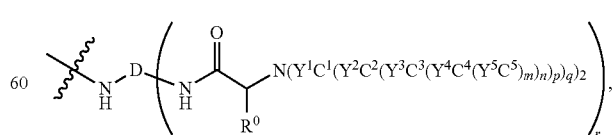

wherein $P^3$ is H or a carboxylic acid protecting group;
wherein:
each of $Y^1, Y^2, Y^3, Y^4, Y^5, C^1, C^2, C^3, C^4, C^5$ are as previously defined and can be the same or different;

m, n, p and q are as previously defined and can be the same or different;

R, R⁰, R¹, R², R³ and R⁴ are as previously defined and can be the same or different;

r is 1, 2, or 3; and

D is aryl; or straight-, branched- or cyclo-alkyl; or

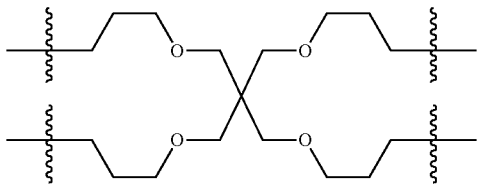 [SMILES: *CCCOCC(COCCC*)(COCCC*)COCCC*]

As indicated above, each of $P^1$, $P^2$, $P^3$ and $P^4$ are protecting groups. Suitable hydroxy protecting groups ($P^1$) include acetate, substituted acetate, benzoate, trialkylsilyl, allyl and benzyl. Suitable amino groups ($P^2$) include Boc, Fmoc or Cbz. Suitable carboxylic acid protecting groups ($P^3$ and $P^4$) include tert-butyl, benzyl and ethyl. Suitable hydroxy, amino and carboxylic acid protecting groups would be known to those skilled in the art and are described in Greene (1999) which is incorporated herein by reference. In the present invention, it is preferable for $P^1$ to be H, $P^2$ to be a Boc protecting group, $P^3$ to be benzyl and $P^4$ to be H.

Preferably, the substituents R, R⁰, R¹, R², R³ and R⁴ are H. The substituents R, R⁰, R¹, R², R³ and R⁴ may also be selected from any one or more of the following: —(CH₂)₄NH₂, —(CH₂)₃NHC=NHNH₂, —CH(CH₃)CH₂CH₃, —CH₂Ph, —CH₂CH(CH₃)₂, —CH₃, —(CH₂)₂SCH₃, —CH₂CO₂H, —(CH₂)₂CO₂H, —CH(OH)CH₃, —(CH₂)₂CONH₂, —CH₂OH, —CH₂SH, —CH₂CONH₂, —CH(CH₃)₂,

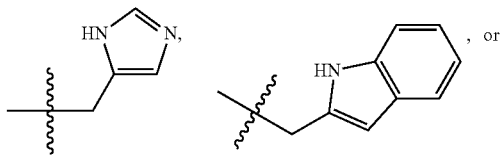

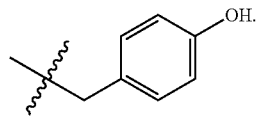

The compounds of formula (I) may be neutral or ionic salts. Preferably, the ionic salt counter ions will be selected from chloride, bromide, trifluoroacetate, p-toluenesulfonate, acetate, sulfate, hydrogen sulfate, carbonate, hydrogen carbonate, phosphate, hydrogen phosphate, triethylammonium, ammonium or pyridinium. Suitable salt forms would be known to those skilled in the art and are described in Stahl (2002).

Preferably, the substituent X is a leaving group or $OP^3$, wherein $P^3$ is as defined above. More preferably, X is OH and $P^3$ is alkyl, aralkyl or benzyl.

As is clear from the above, the dendrimers of the present invention have tertiary amines at the branching point allowing the use of amino acids as building blocks. In particular, the dendrimers of the present invention are built on glycine as the branching point. However, glycine can be substituted with other amino acids to give many possible substituents and variations.

Suitable building blocks for use in the present invention include the following:

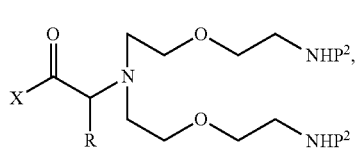

A

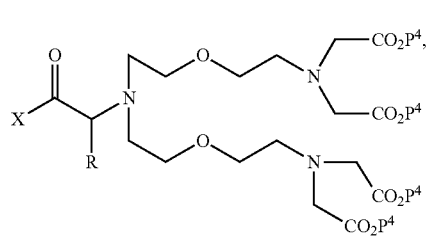

B

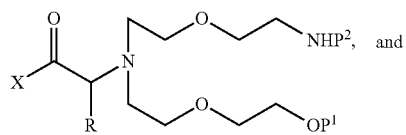

C

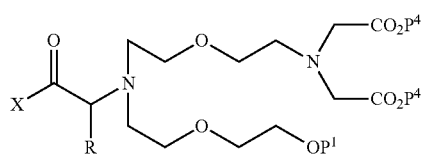

D

In each of these building blocks, $P^1$, $P^2$, $P^4$ and R are as previously defined and the substituent X is a leaving group or $OP^3$, wherein $P^3$ is as defined previously.

Preferably, the dendrimers of the present invention are made by coupling together any one or more of the above building blocks. In one embodiment of the present invention, the compounds of formula (I) are made by coupling together building block A as defined above. Examples of dendrimers which include only building block A include:

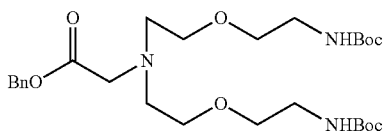
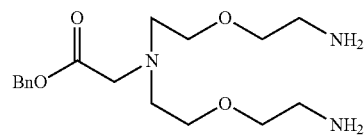

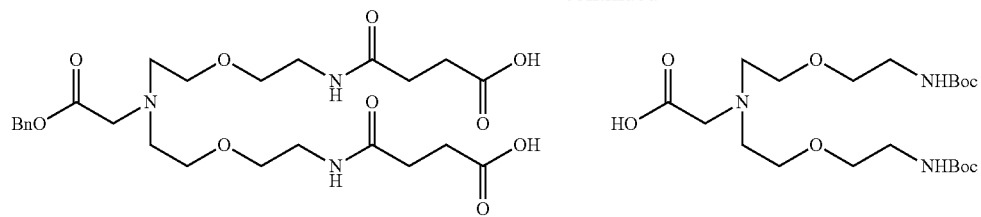
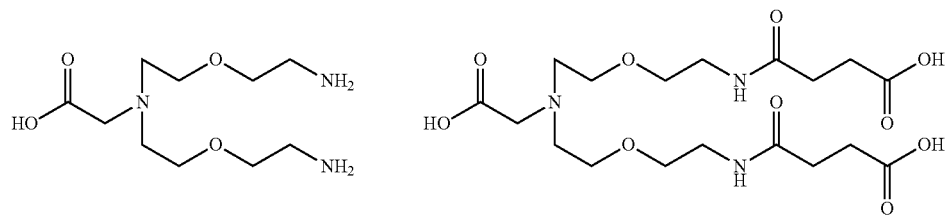
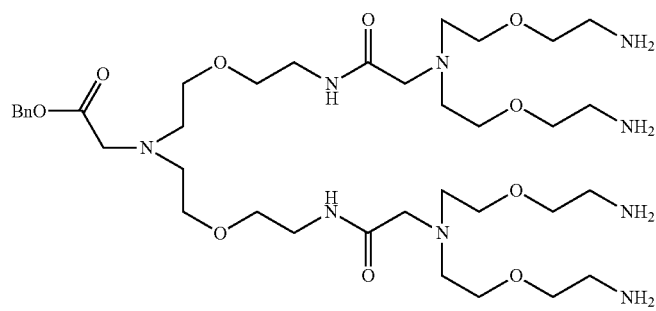
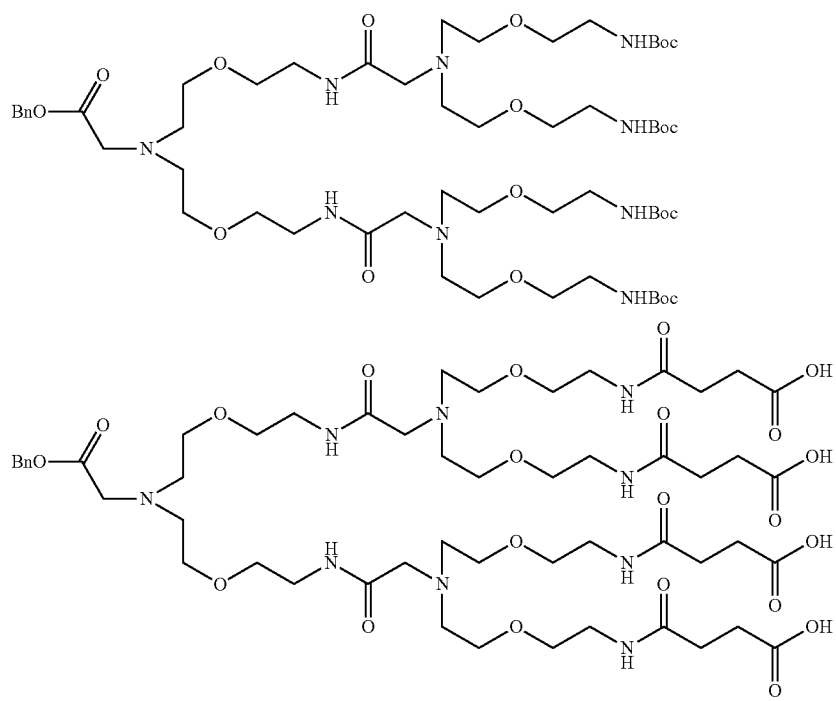

-continued
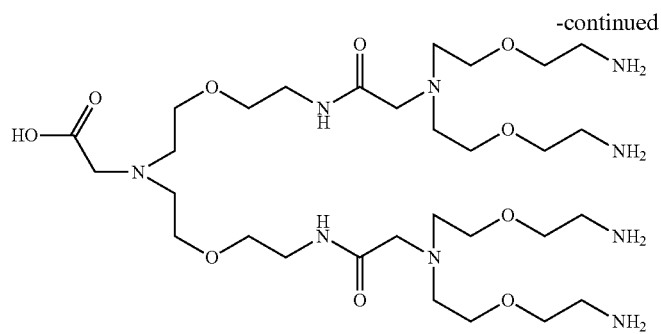
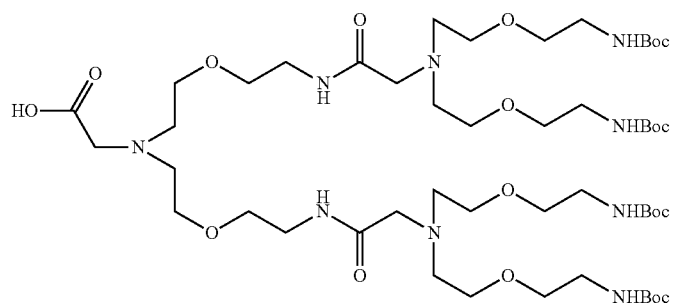
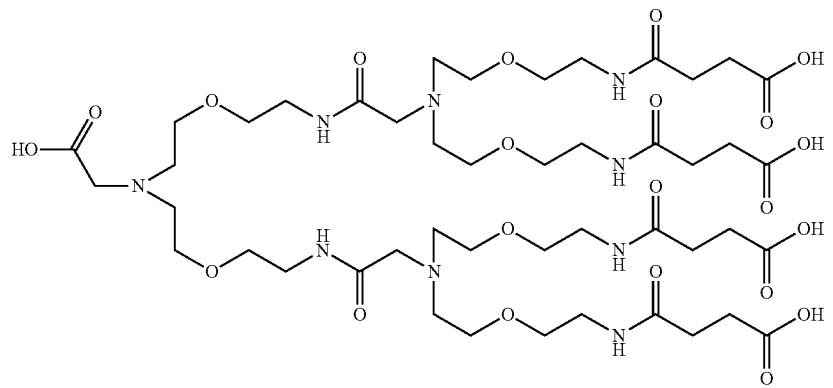

-continued
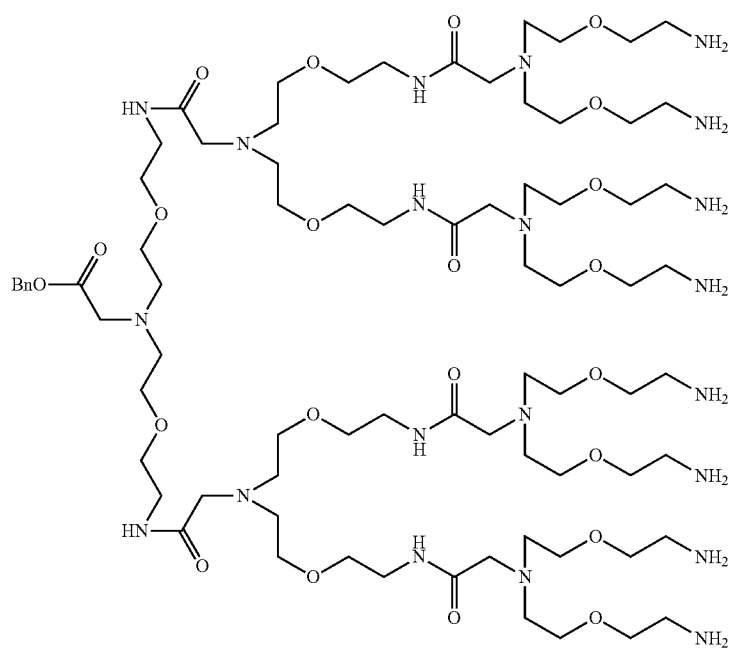
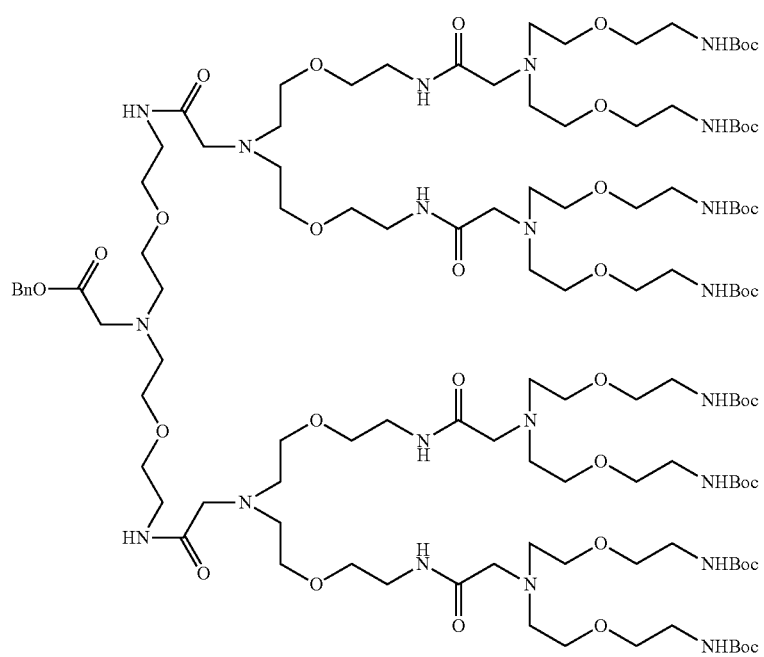

-continued
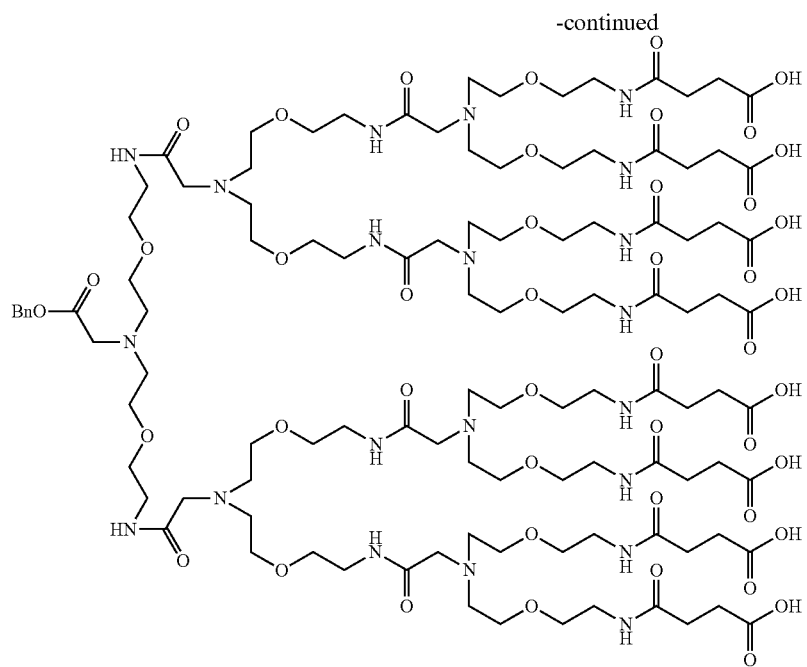
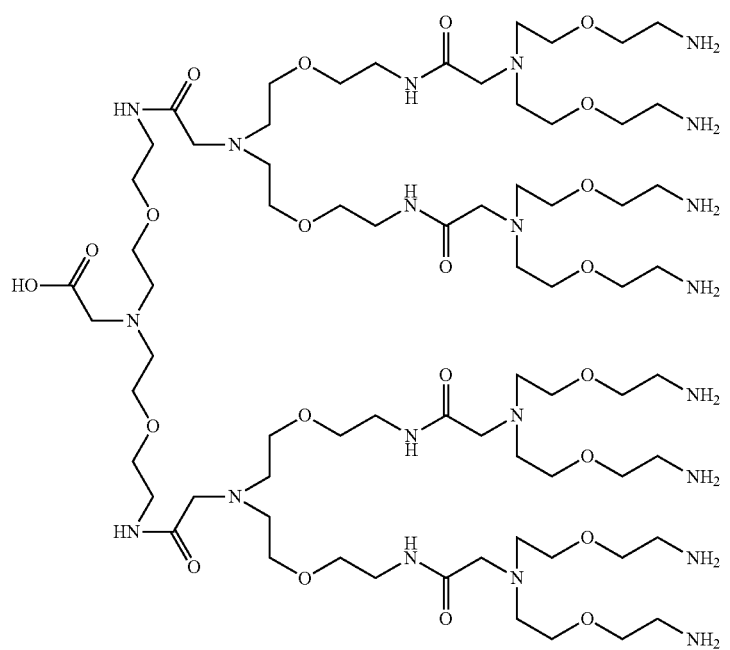

-continued
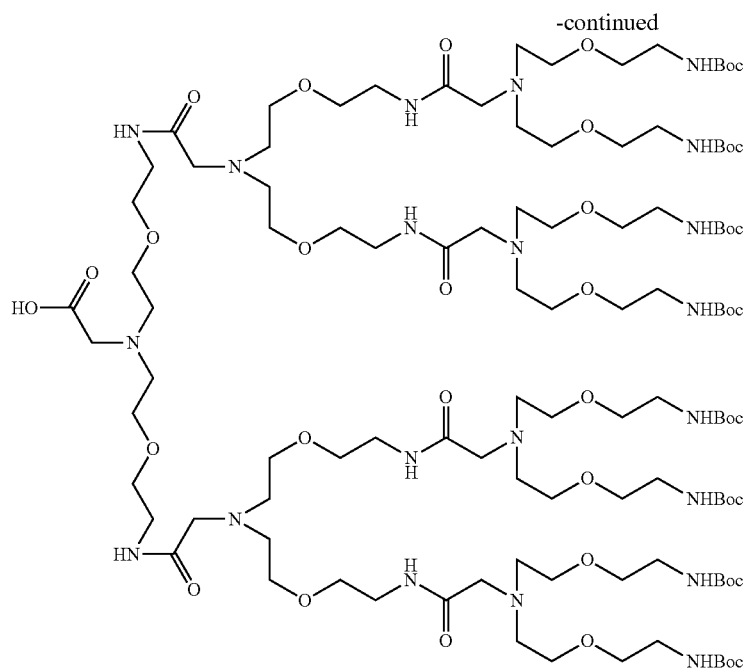
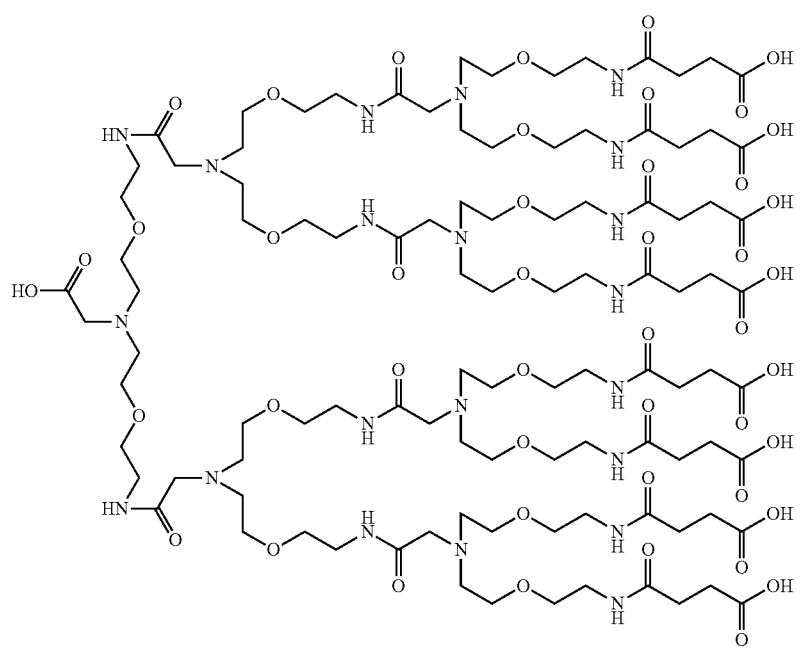

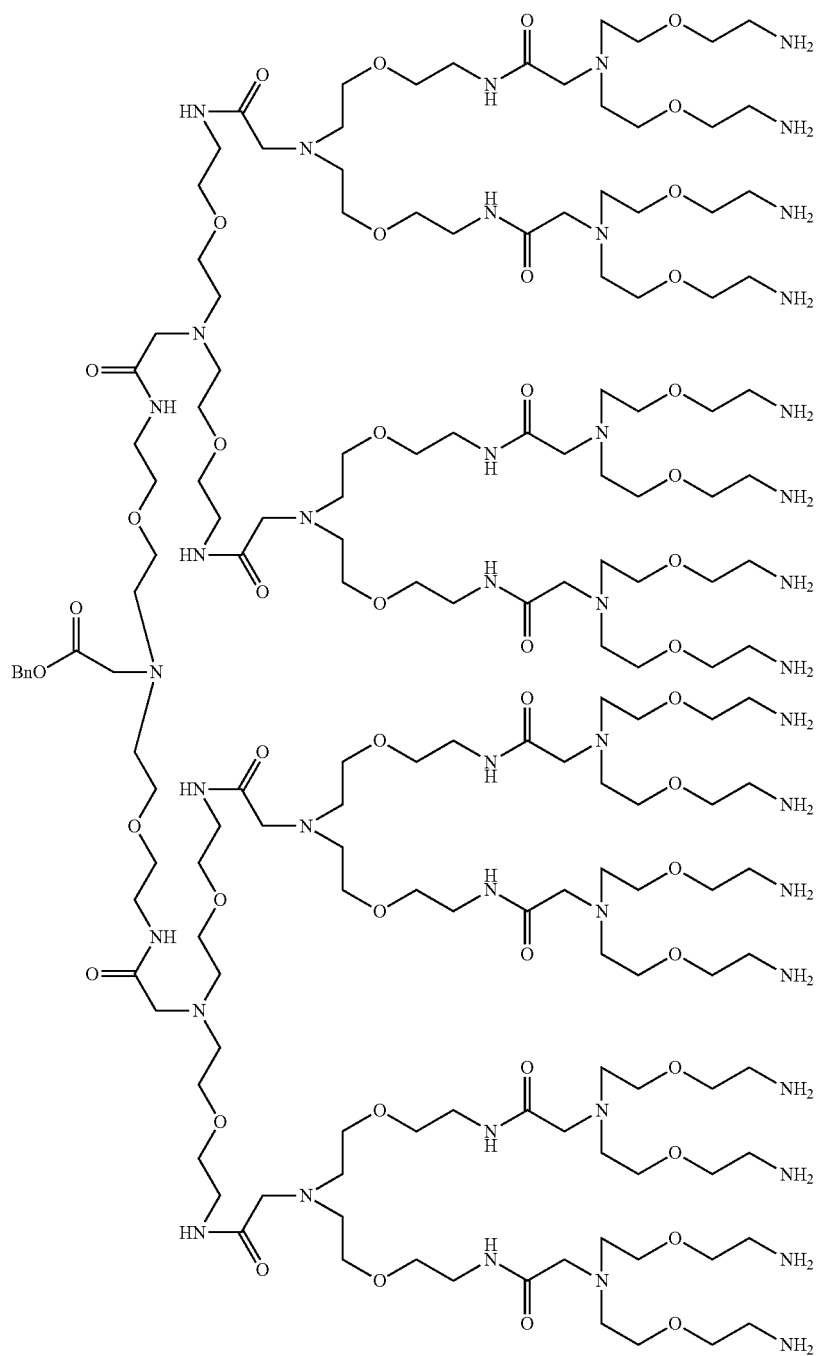 [SMILES: NCCOCCN(CCOCCN)CC(=O)NCCOCCN(CCOCCNC(=O)CN(CCOCCN)CCOCCN)CC(=O)NCCOCCN(CCOCCNC(=O)CN(CCOCCNC(=O)CN(CCOCCN)CCOCCN)CCOCCNC(=O)CN(CCOCCN)CCOCCN)CC(=O)NCCOCCN(CCOCCNC(=O)CN(CCOCCNC(=O)CN(CCOCCNC(=O)CN(CCOCCN)CCOCCN)CCOCCNC(=O)CN(CCOCCN)CCOCCN)CCOCCNC(=O)CN(CCOCCNC(=O)CN(CCOCCN)CCOCCN)CCOCCNC(=O)CN(CCOCCN)CCOCCN)CC(=O)OCc1ccccc1]

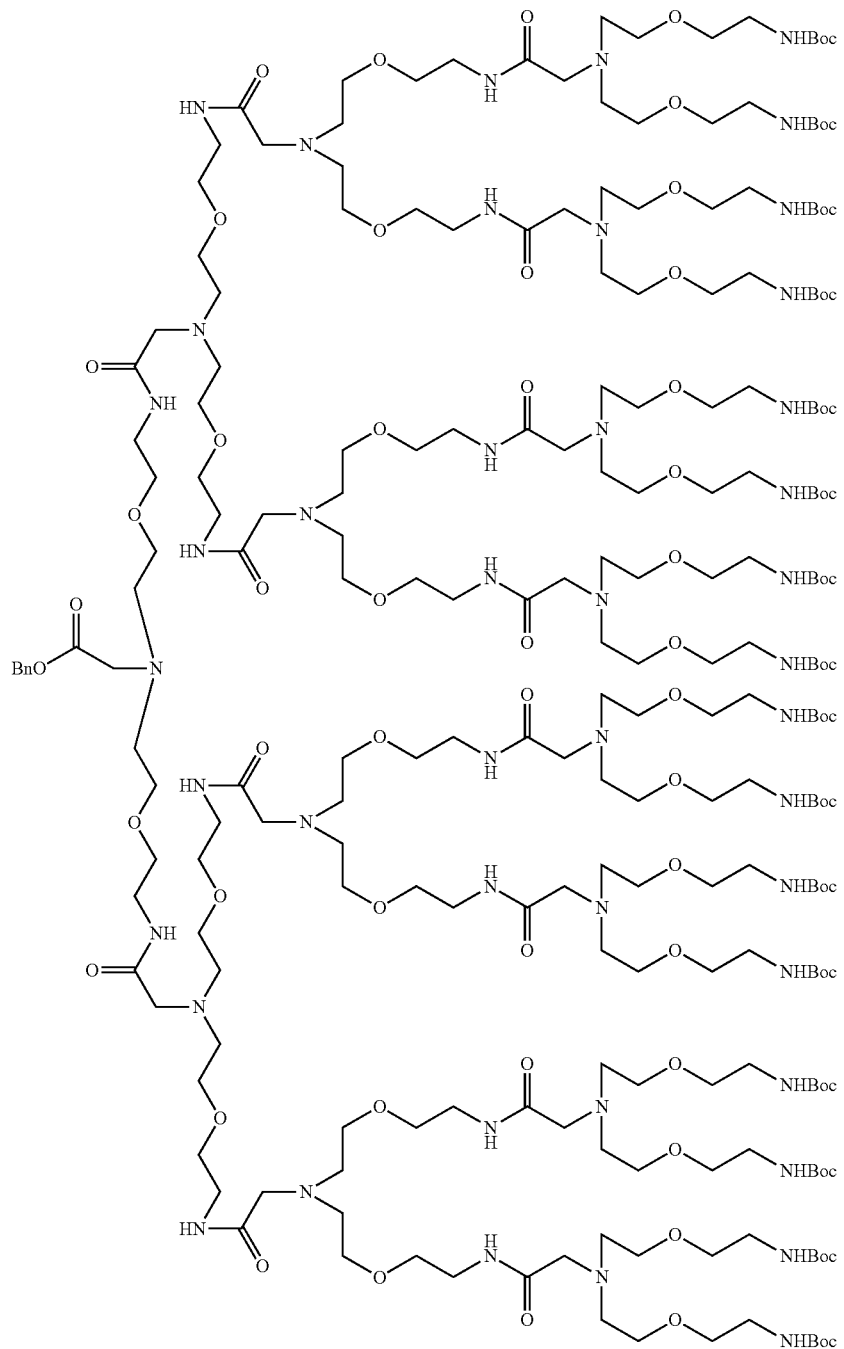

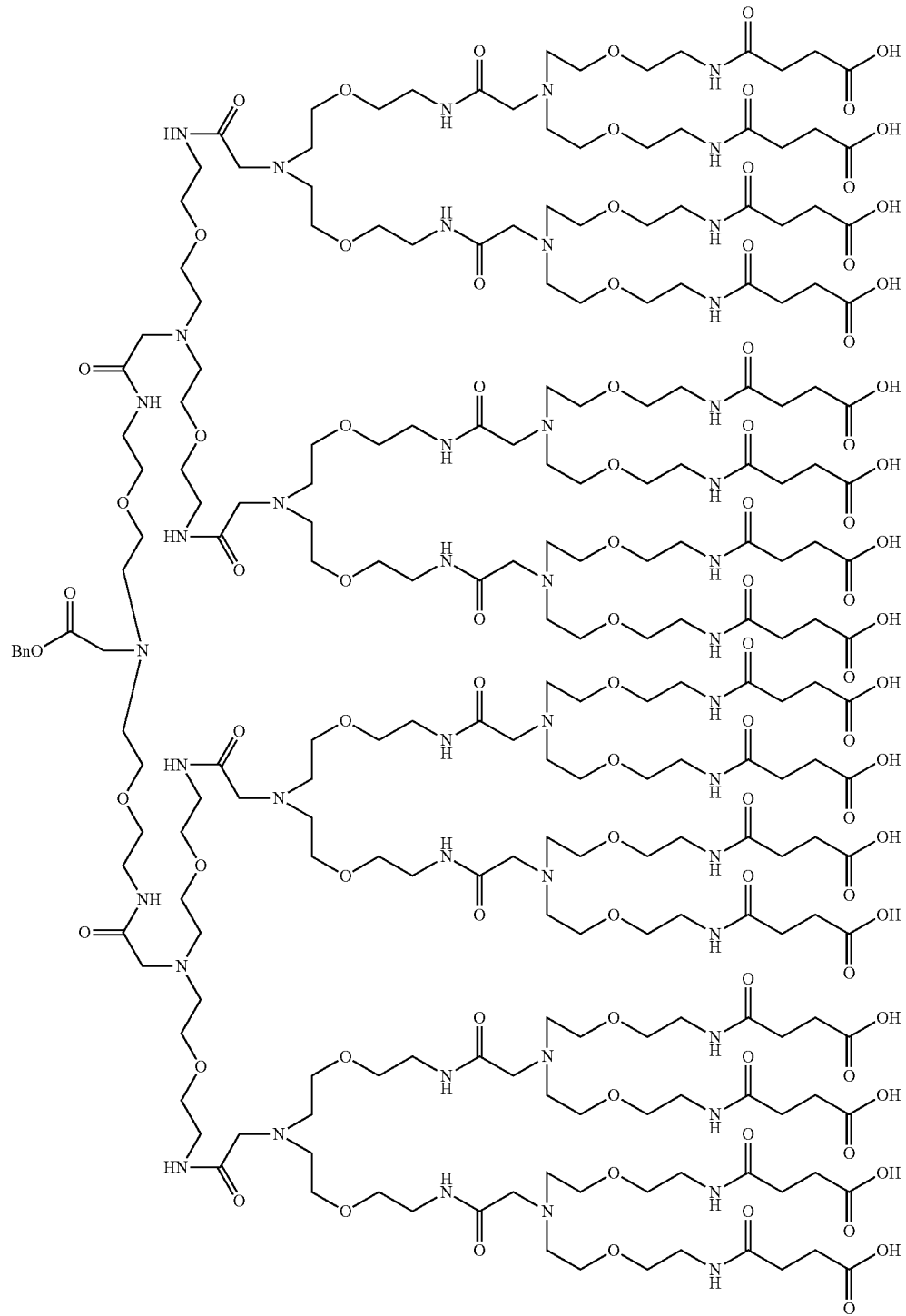

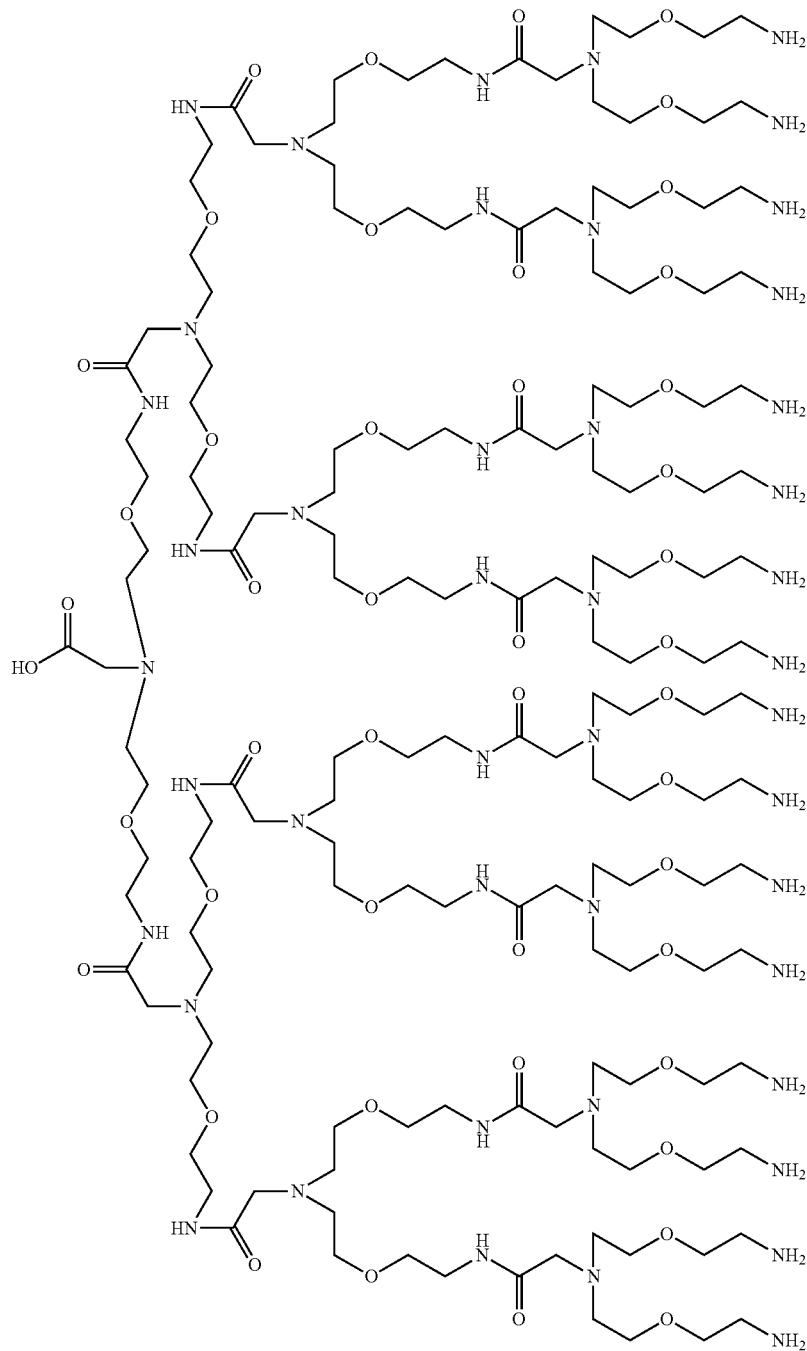 [SMILES: NCCOCCN(CCOCCN)CC(=O)NCCOCCN(CCOCCNC(=O)CN(CCOCCN)CCOCCN)CC(=O)NCCOCCN(CCOCCNC(=O)CN(CCOCCNC(=O)CN(CCOCCN)CCOCCN)CCOCCNC(=O)CN(CCOCCN)CCOCCN)CC(=O)NCCOCCN(CCOCCNC(=O)CN(CCOCCNC(=O)CN(CCOCCNC(=O)CN(CCOCCN)CCOCCN)CCOCCNC(=O)CN(CCOCCN)CCOCCN)CCOCCNC(=O)CN(CCOCCNC(=O)CN(CCOCCN)CCOCCN)CCOCCNC(=O)CN(CCOCCN)CCOCCN)CC(=O)O]

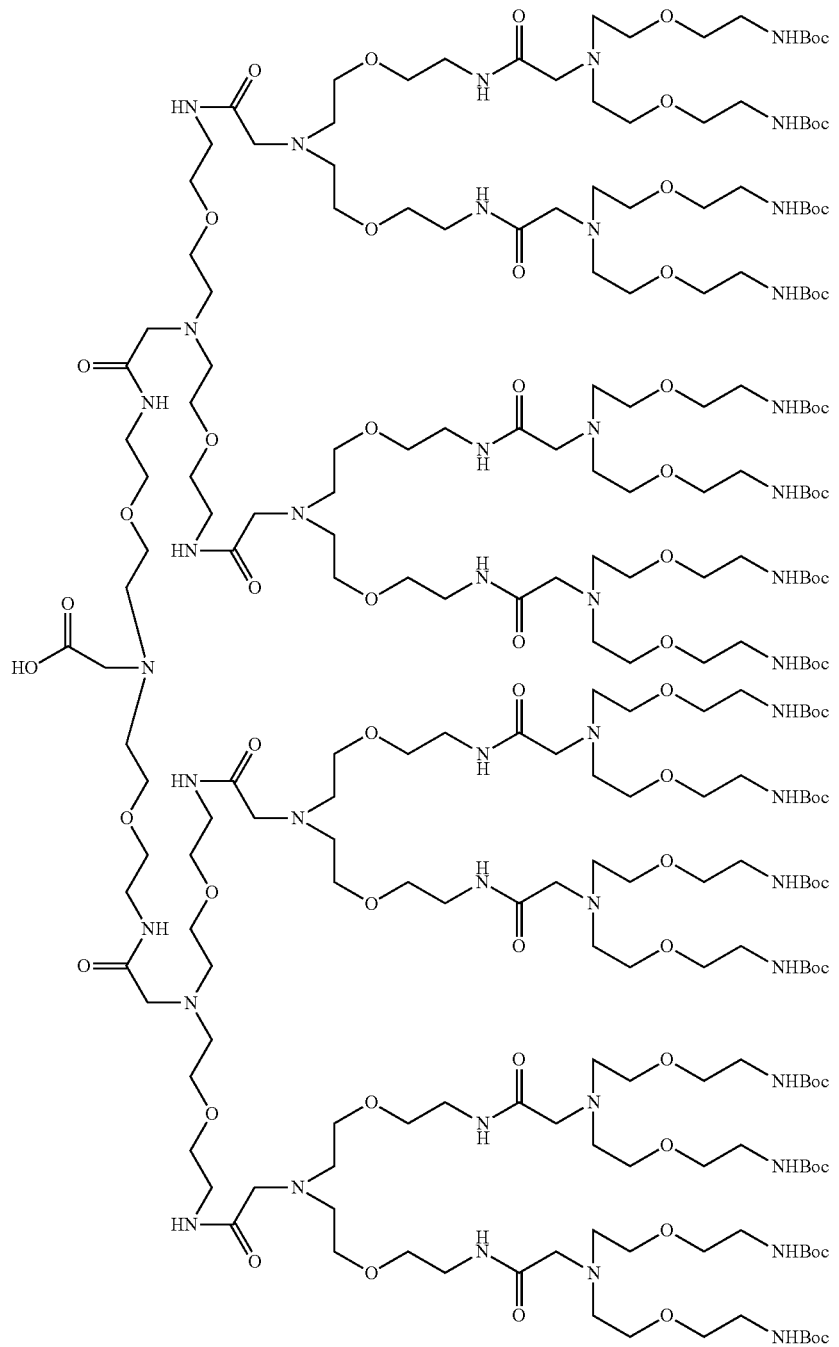

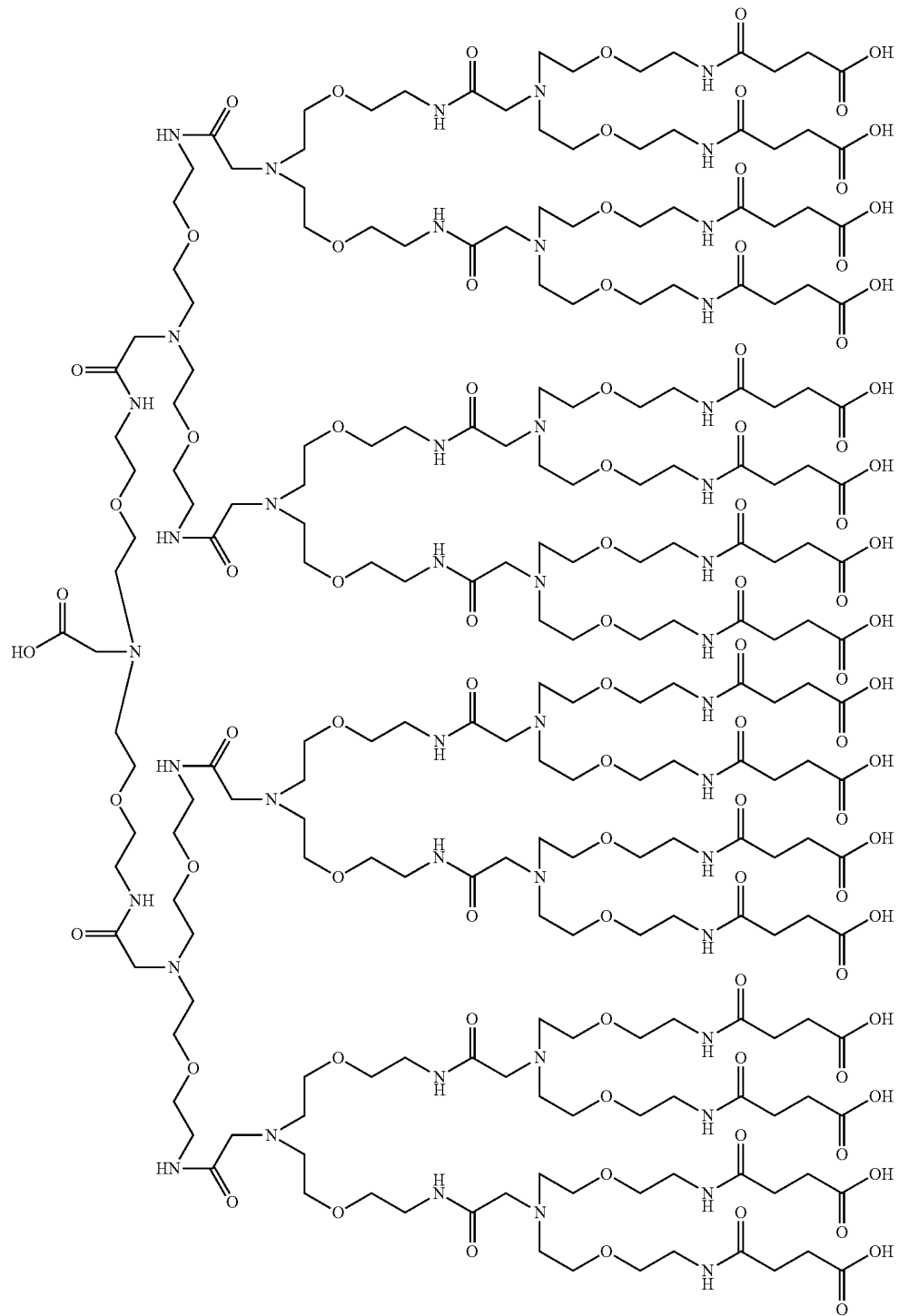

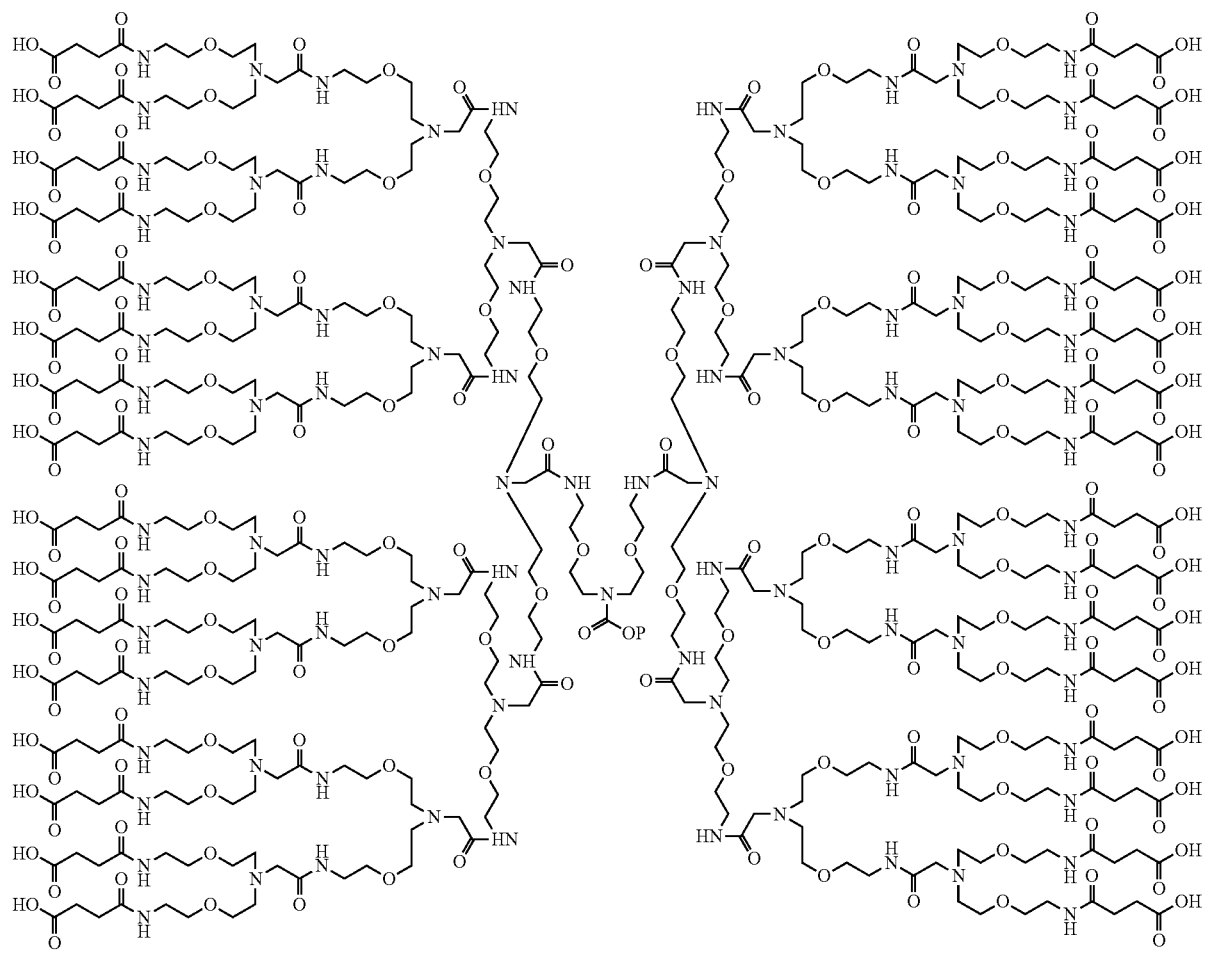
P = H or Bn

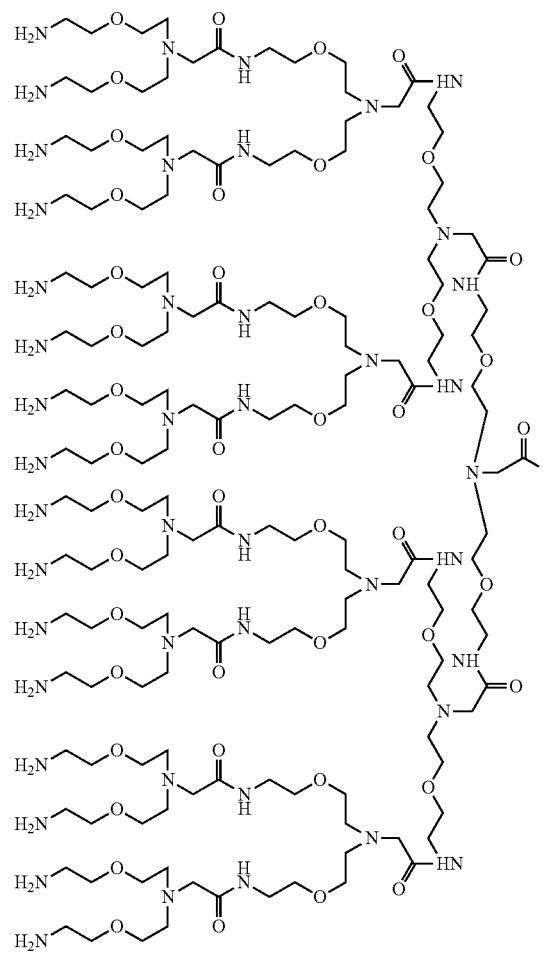 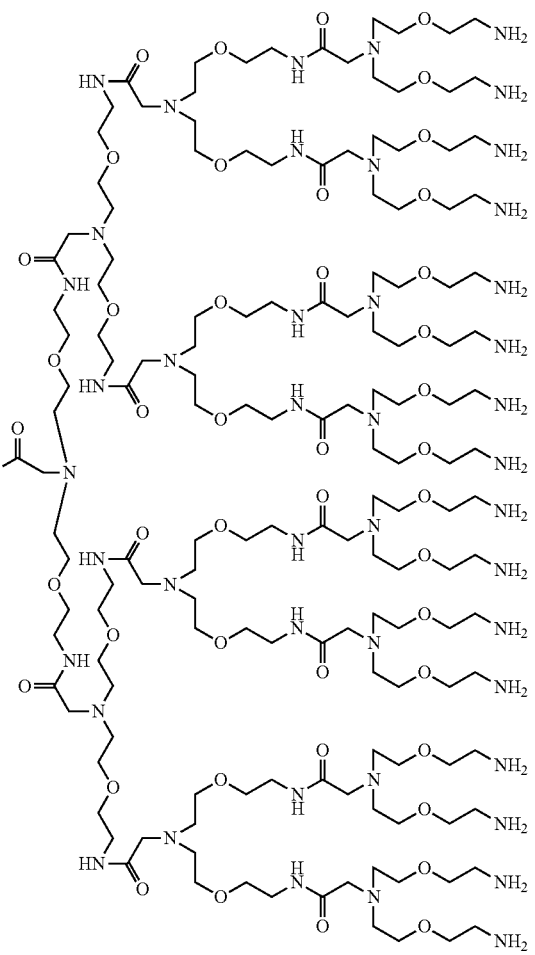
P = H or Bn

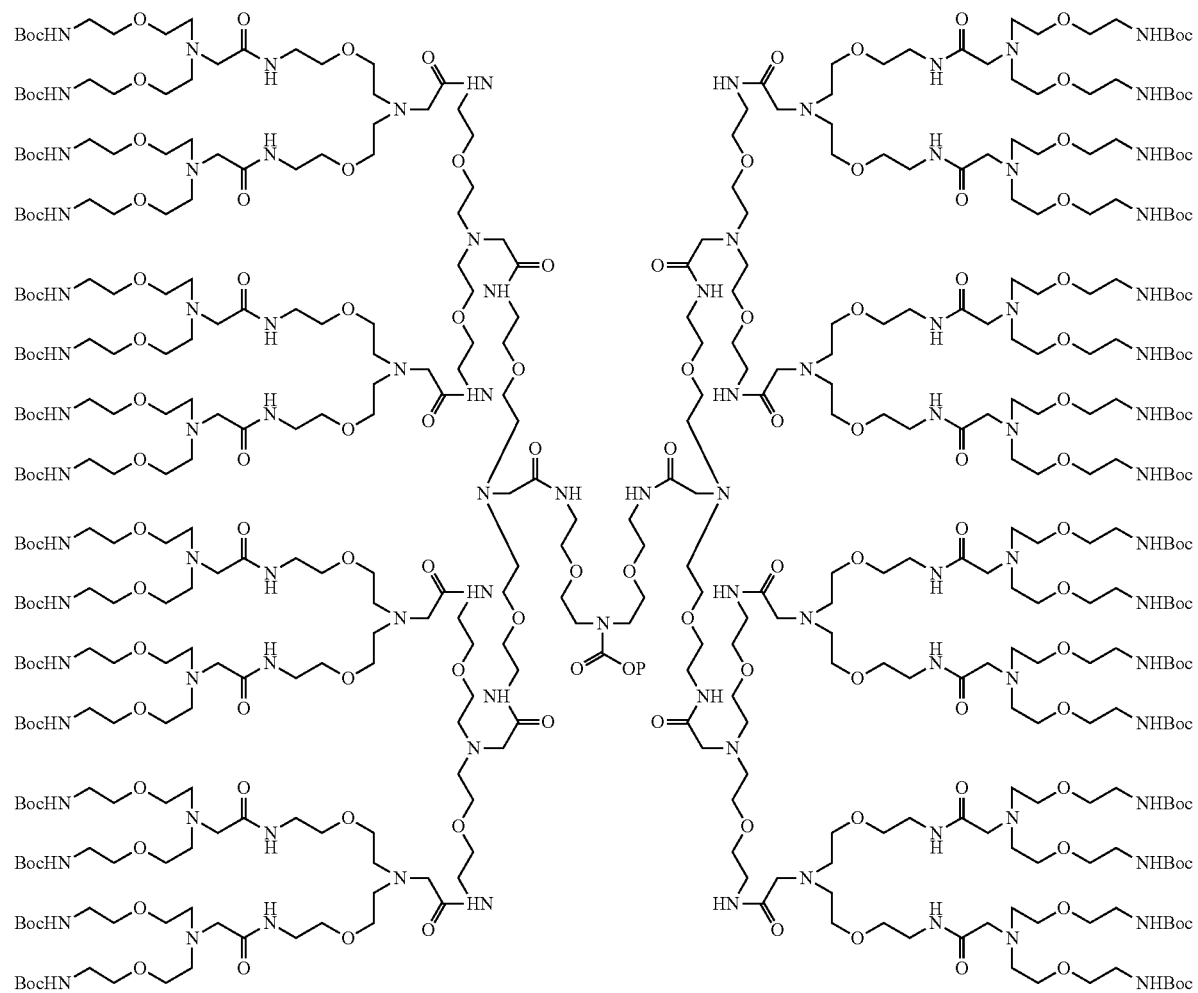
P = H or Bn

Any one or more of the OH groups in the each of the dendrimers of formula (I) may be replaced with OP¹ (as defined previously). Likewise, any one or more of the NH₂ groups may be replaced with NHP² (as defined previously) and any one or more of the CO₂H groups may be replaced with CO₂P³ (as defined previously).

As will be understood by a person skilled in the art, the present invention is not limited to the above examples of dendrimers which have been built up using only building block A. Rather the above represent examples of what can be achieved when the same building blocks are employed.

Alternatively, in another embodiment of the present invention, the compounds of formula (I) are made by coupling together different building blocks selected from A to D as previously defined.

Two examples of dendrimers of the present invention which have been formed by coupling different building blocks together are:

A further example of a dendrimer which is built up from different building blocks is:

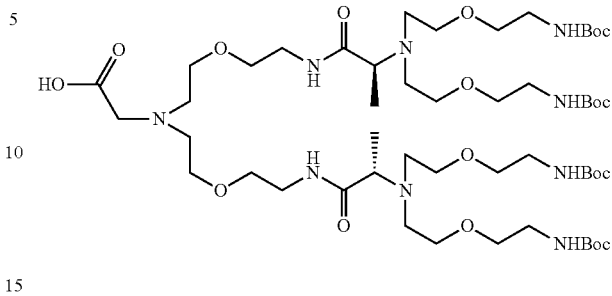

In this dendrimer, R, R⁰, R¹, R², R³ or R⁴ are the side chain of a natural amino acid.

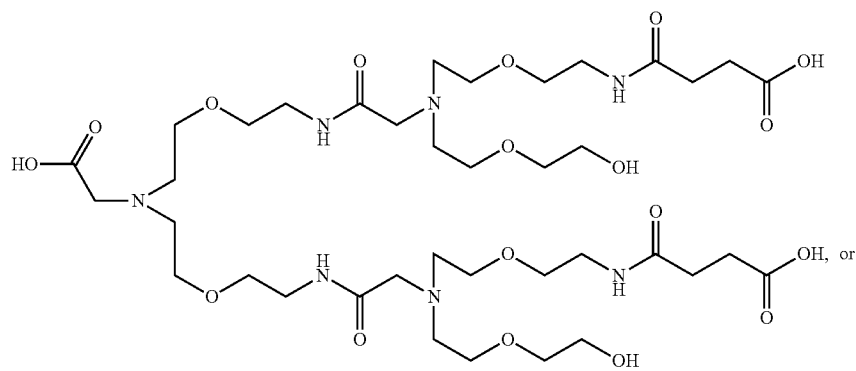

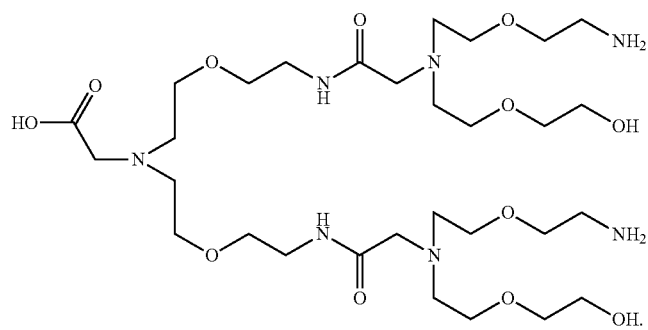

In the above dendrimers, building blocks A and C are employed. They are also an example of dendrimers where the substituents Y¹, Y², Y³, Y⁴ or Y⁵ are

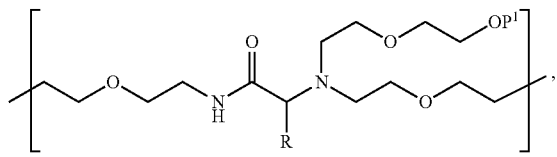

wherein P¹ is as previously defined.

Preferably, any one or more of building blocks A to D are linked by the following building block: $(NHP^2)_s$-D-$(NH_2)_r$ E. Employment of E results in the formation of two or more of the same or different dendrimer structures connected to the central building block E. In building block E, D and r are as previously defined and s is 1, 2 or 3, such that s+r equals 2, 3 or 4. Preferably, D is a straight chain alkyl. This results in the formation of 'bow-tie' or 'Janus' dendrimers.

An example of a dendrimer where building block E is employed as a linker is:

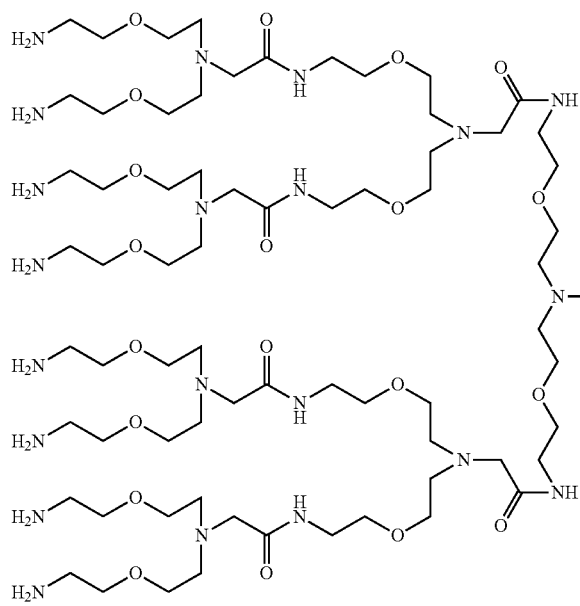
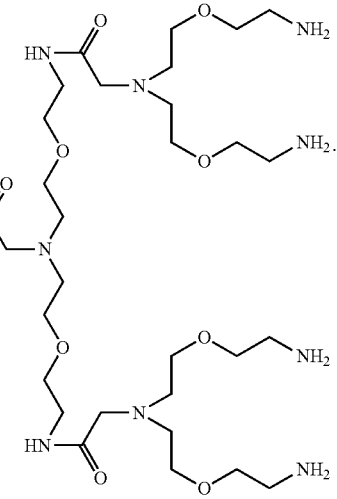

The above dendrimer comprises multiple building block A's linked by a building block E. It is also an example of a dendrimer where the substituent Y is

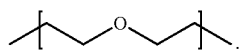

Another example of a dendrimer comprising

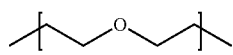

as substituent Y is:

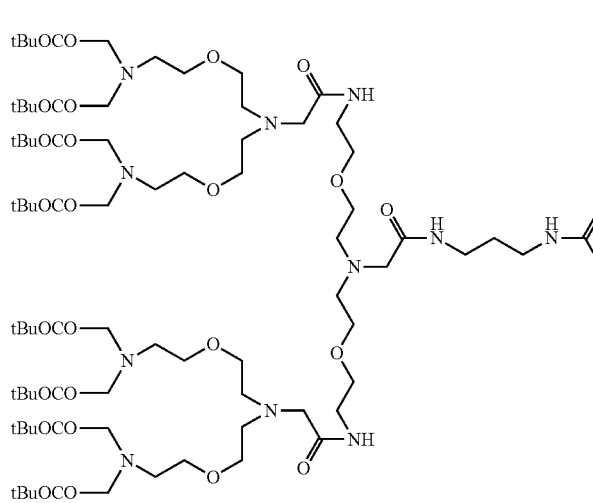

In another embodiment of the present invention, any one of the substituents $C^1$, $C^2$, $C^3$, $C^4$ or $C^5$ may also form a terminal group in the dendrimers of the present invention. Preferably, $C^1$, $C^2$, $C^3$, $C^4$ or $C^5$ is $N(CH_2CO_2P_4)_2$ when employed as a terminal group, wherein $P^4$ is as previously defined. Alternatively, $Y^1C^1$, $Y^2C^2$, $Y^3C^3$, $Y^4C^4$ or $Y^5C^5$ is

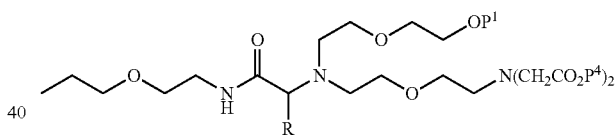

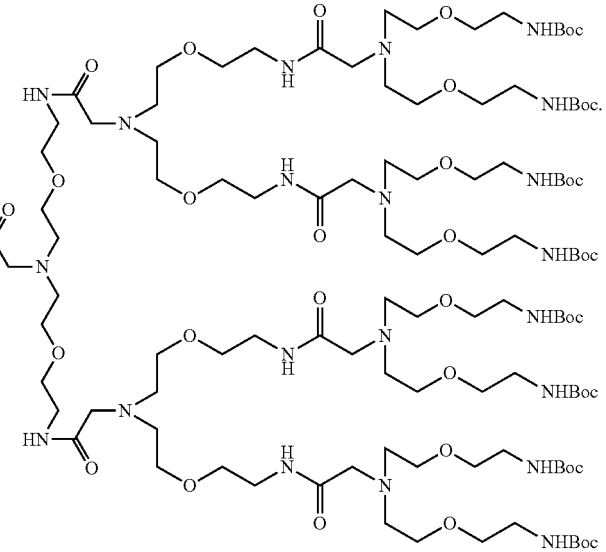

when employed as a terminal group, wherein $P^1$ and $P^4$ are as previously defined. As a further alternative, $Y^1C^1$, $Y^2C^2$, $Y^3C^3$, $Y^4C^4$ or $Y^5C^5$ is

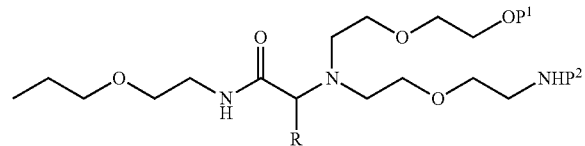

when employed as a terminal group, wherein $P^1$ and $P^2$ are as previously defined.

Examples of dendrimers where $C^1$, $C^2$, $C^3$, $C^4$ or $C^5$ are $N(CH_2CO_2P^4)_2$ include:

These are also examples of dendrimers built up from different building blocks, the first comprising building blocks A and B, the second comprising building blocks A and D, and the final 'bow-tie' dendrimer comprising building blocks A, B and E.

As will be understood by a person skilled in the art, the present invention is not limited to the above examples of dendrimers which have been built up from different building blocks. Rather the above represent examples of what can be achieved when different building blocks are employed.

In another embodiment of the present invention, building blocks B, C, or D may form an outer generation of the dendrimers of the present invention. Examples of dendrimers where building block B forms the outer generation include:

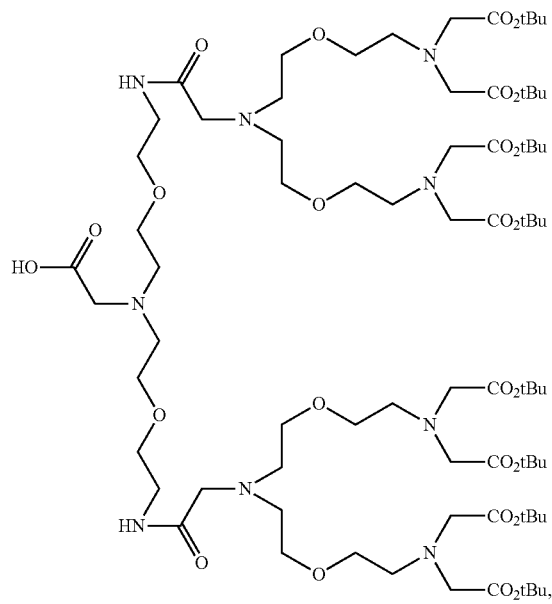

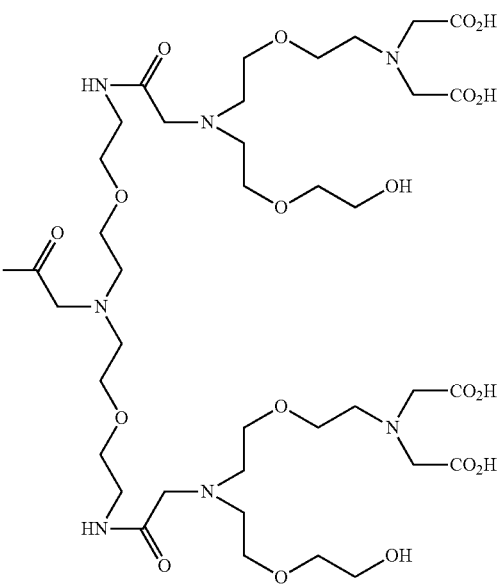

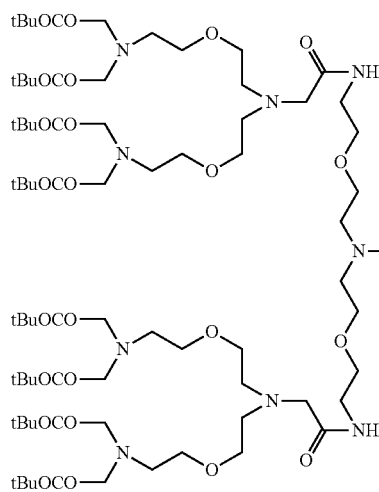

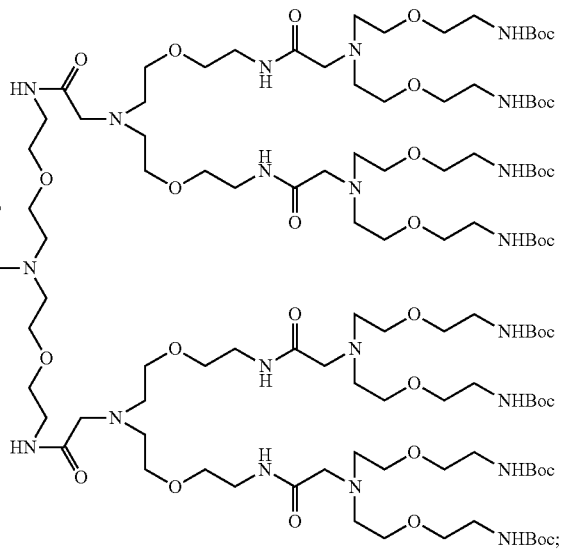

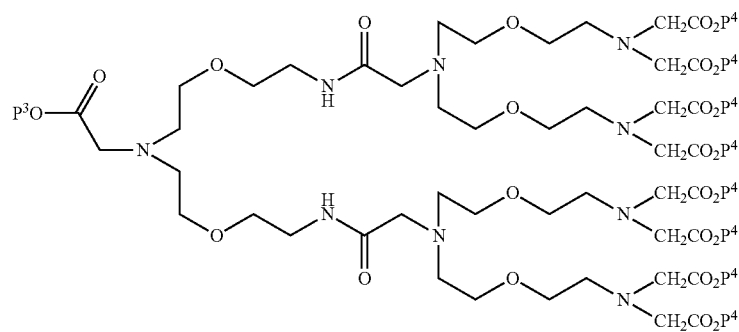
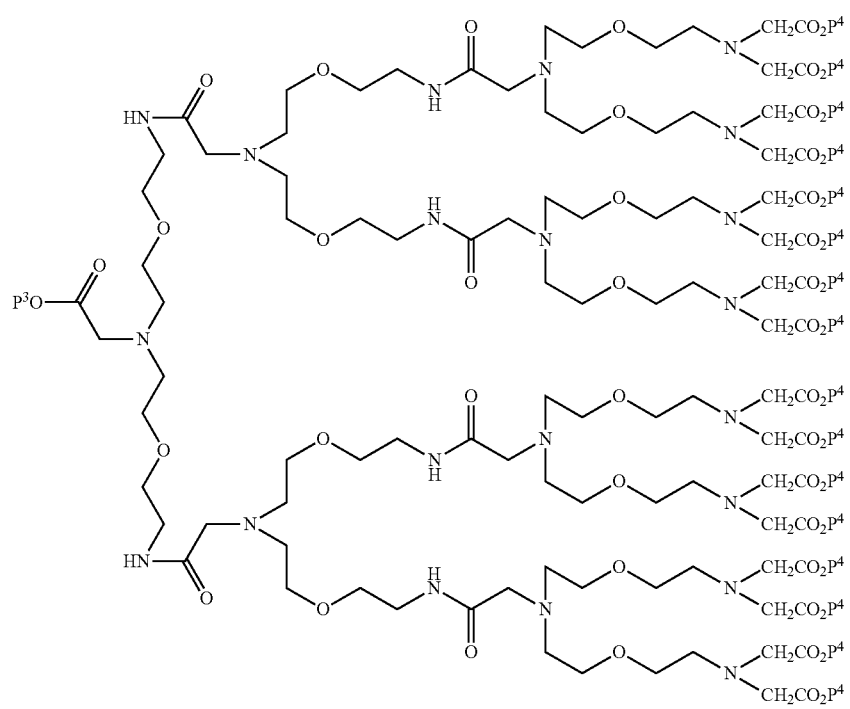

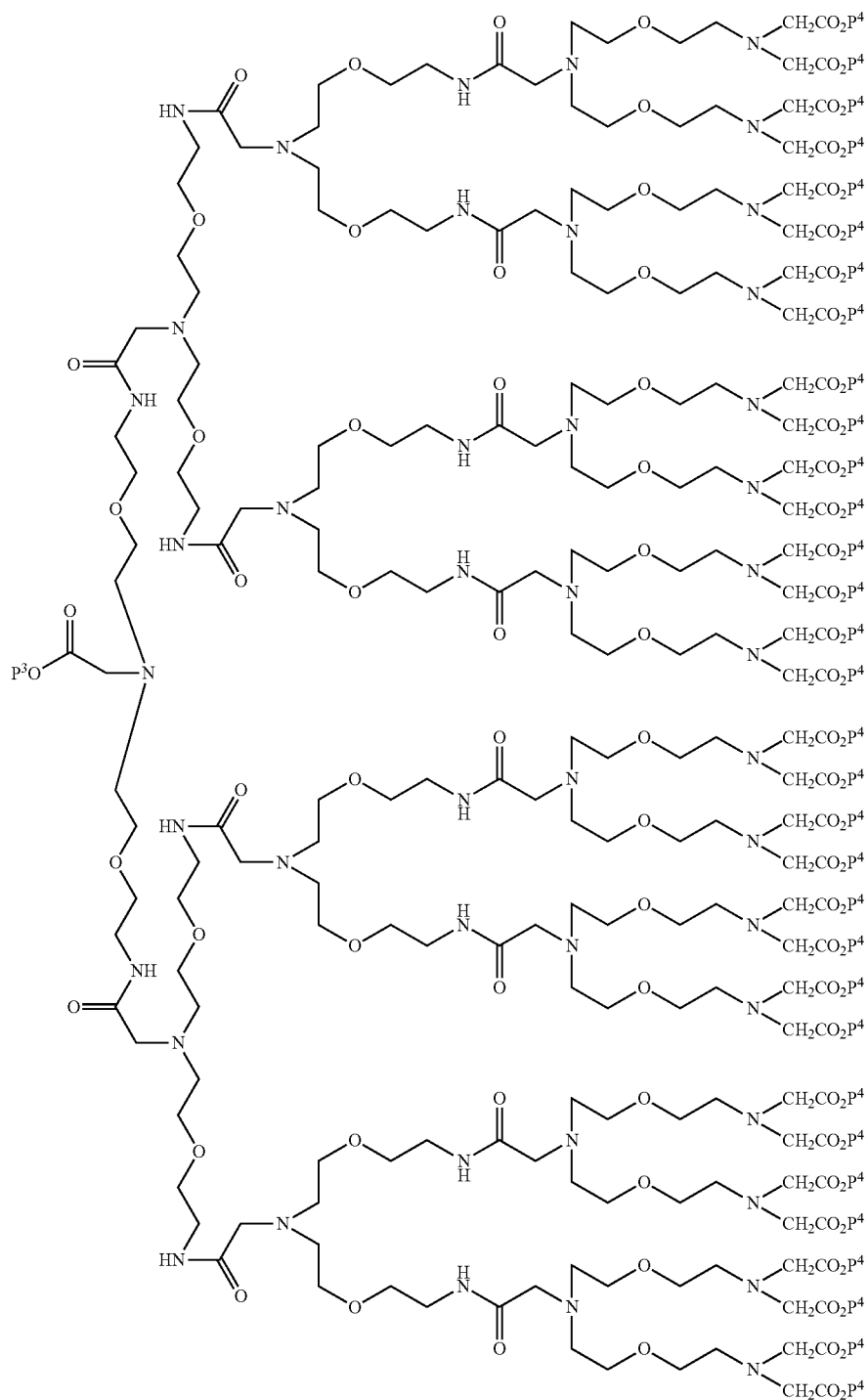

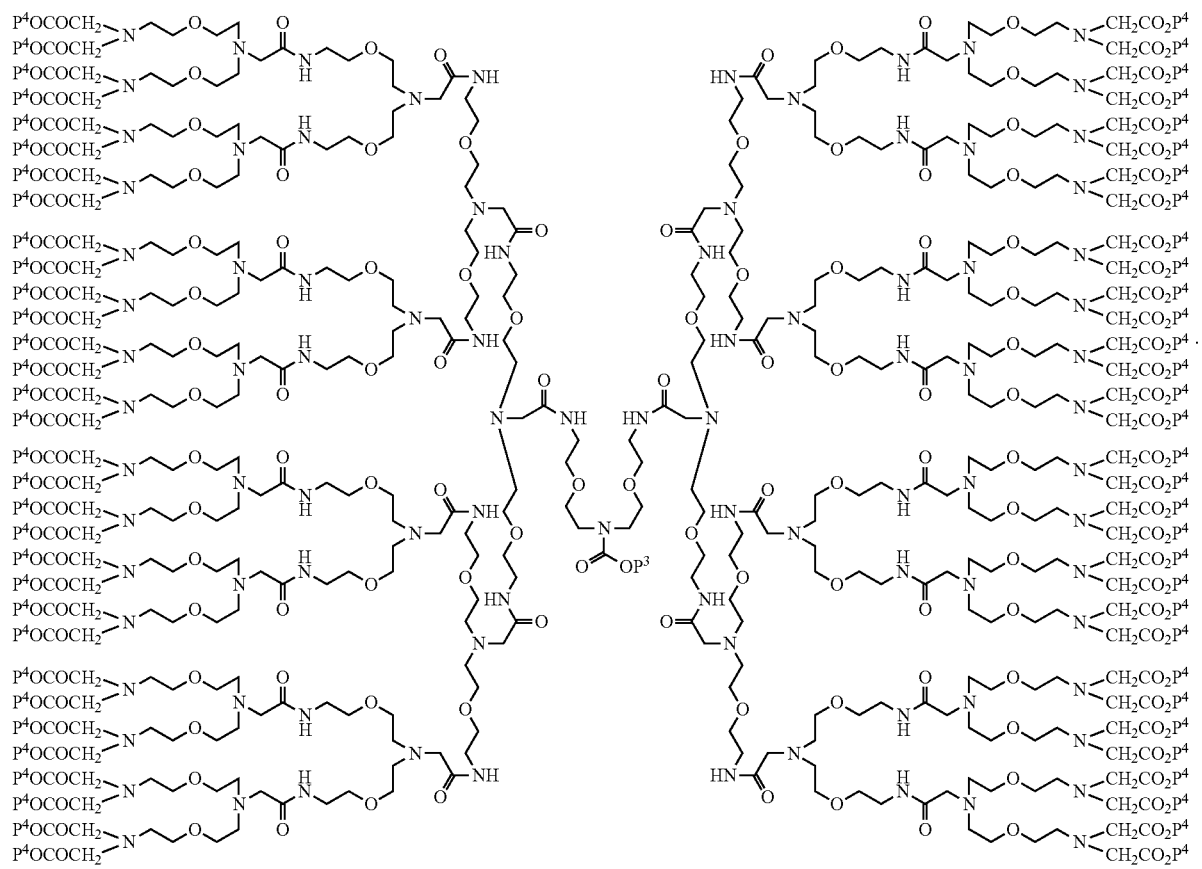

Examples of dendrimers where building block C forms the outer generation include:
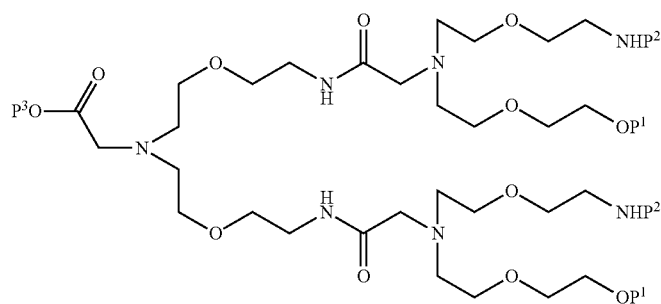
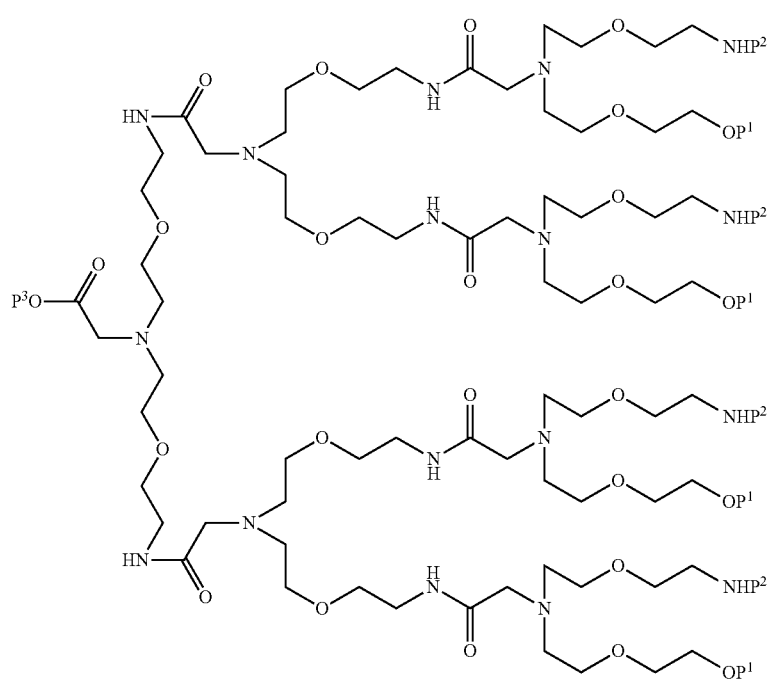

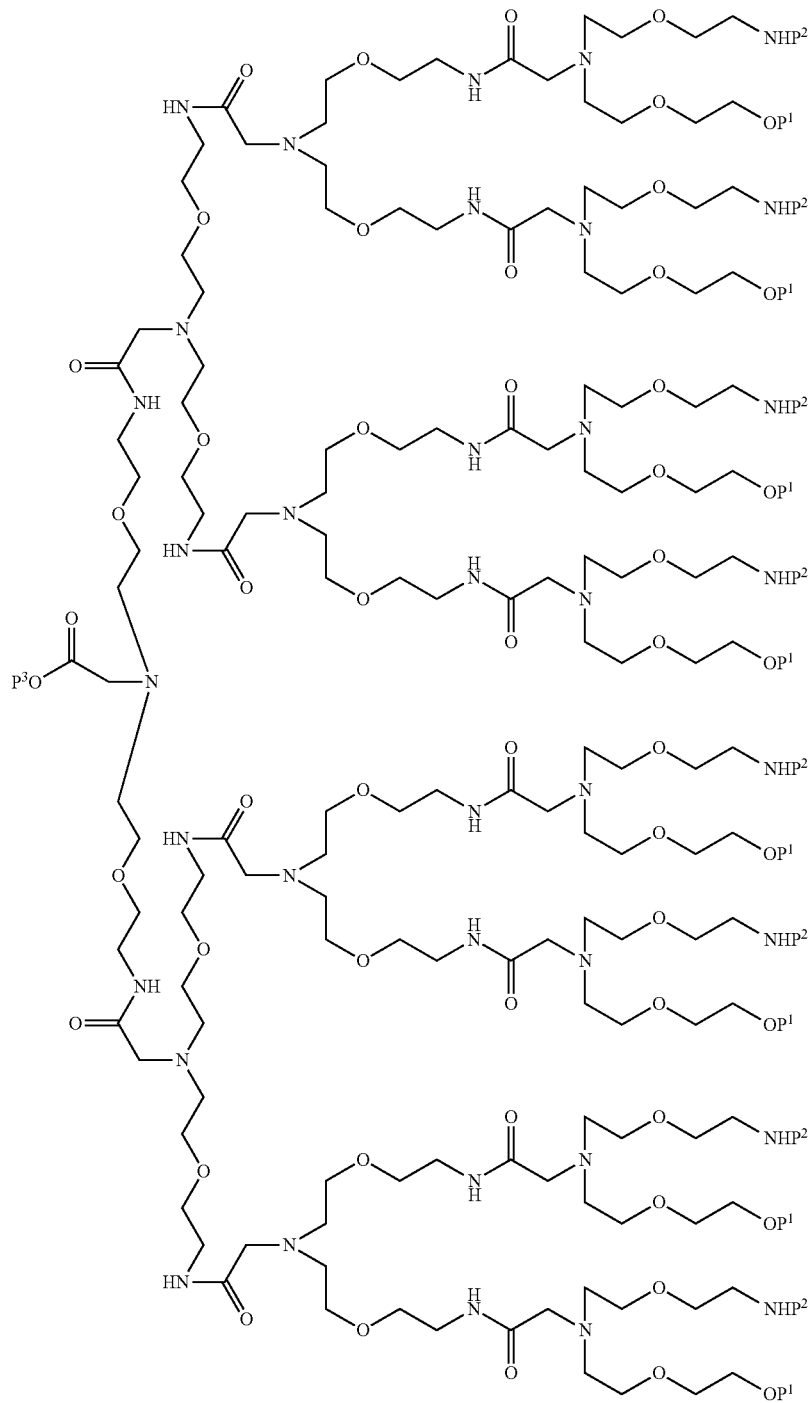

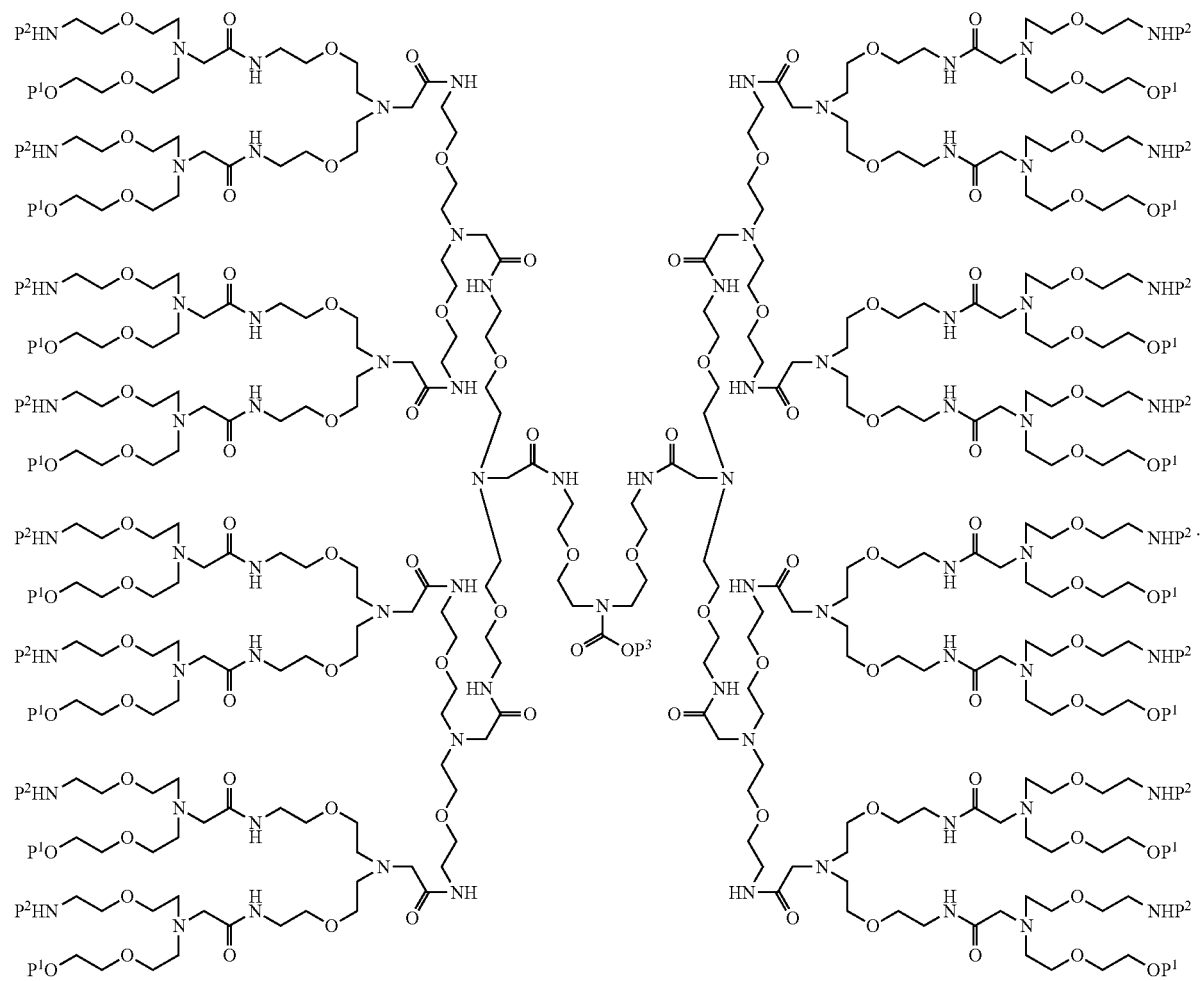

Examples of dendrimers where building block D forms the outer generation include:
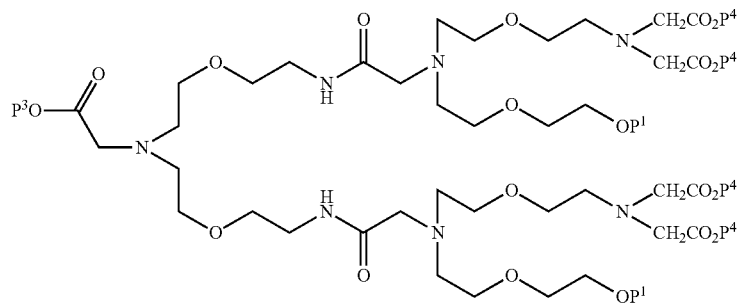
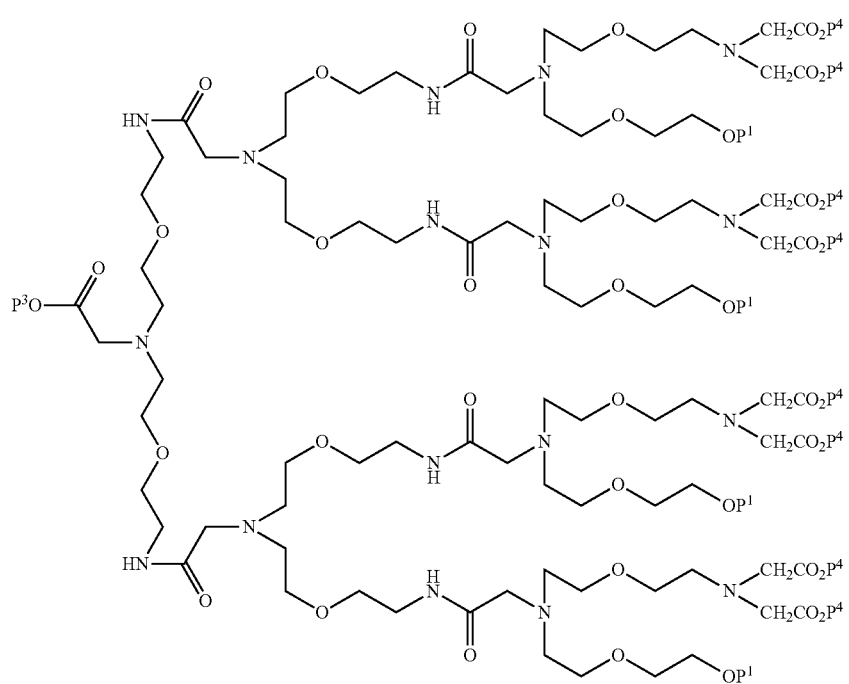

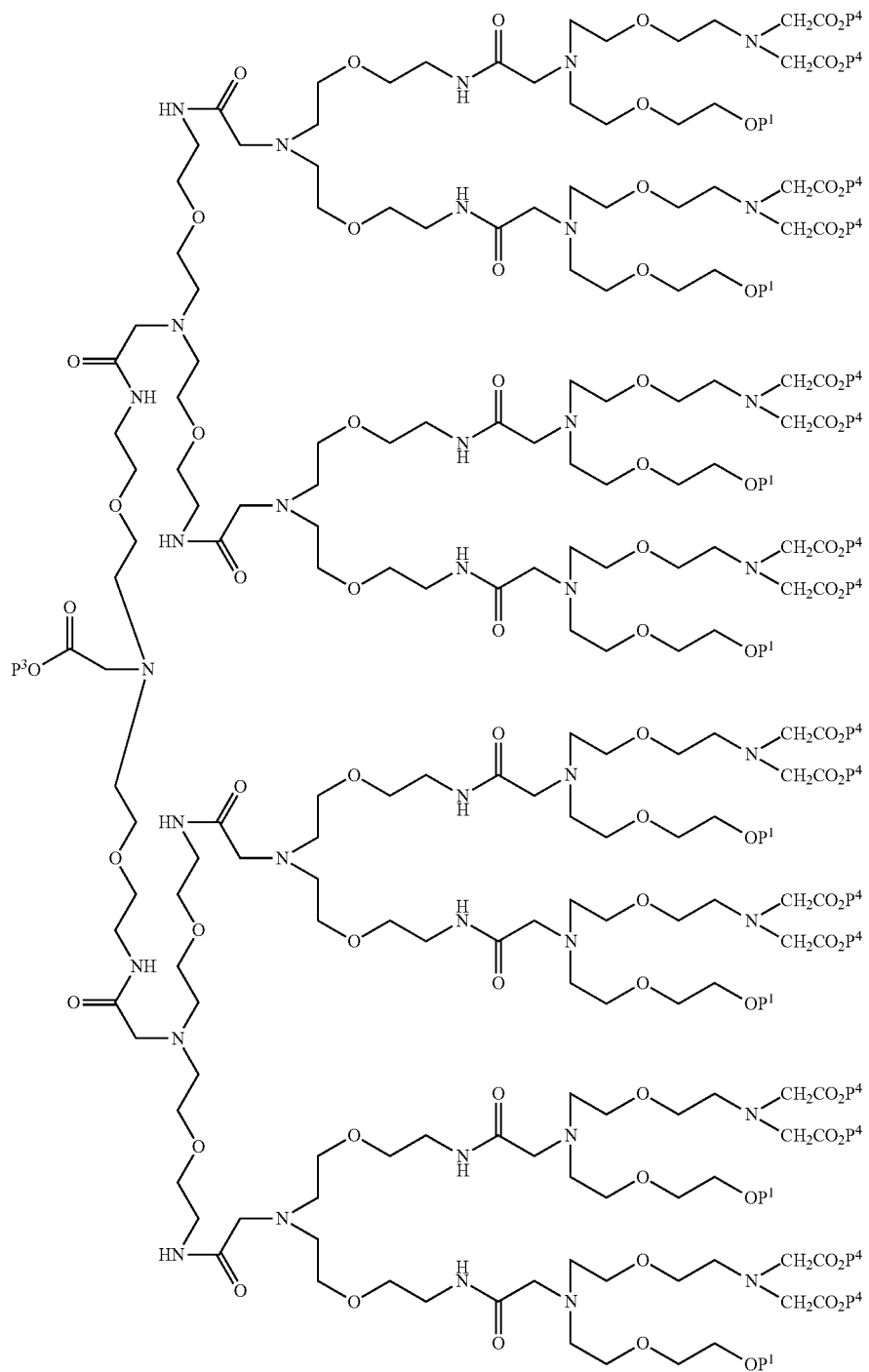

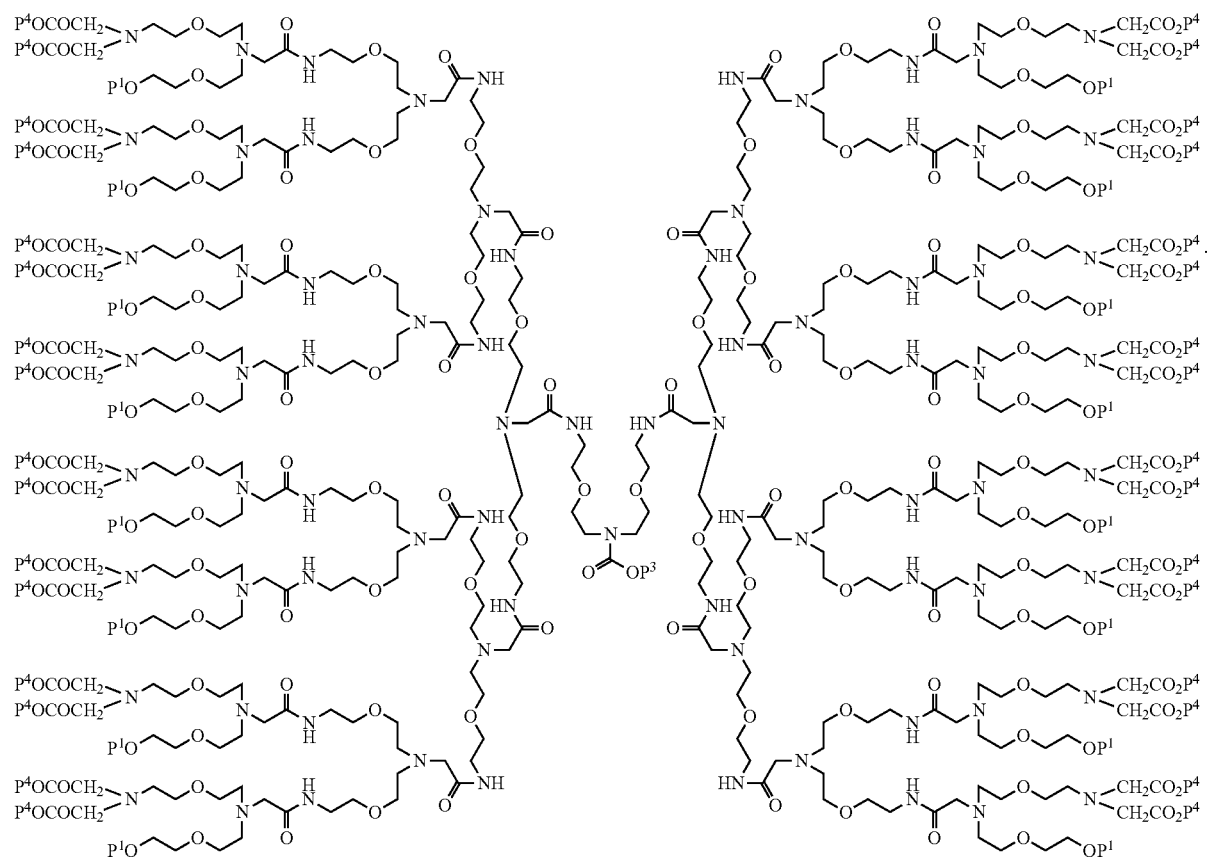

General Methods

The invention may also be said to lie in the method of manufacture of dendrimers of formula (I) from any one or more of building blocks A to E. In a preferred option, the method of manufacture makes use of different building blocks, wherein the building blocks include natural amino acids.

In particular, the dendrimers of the present invention have tertiary amines at the branching point. The use of amino acids in the synthesis of the dendrimers of the present invention is preferable as they are low cost and their use gives easy access to a range of structures and functionalities. The present invention also makes use of $(CH_2)_2O(CH_2)_2$ linkers which allow for an increase in dendrimer size and solubility in biological media.

The dendrimers of the present invention also have an increased linker length. This has the advantage of giving increased size and increased flexibility in less synthetic steps. This results in a more efficient synthesis with minimal effect on biological efficacy due to loss of multi-valency.

Synthesis of Building Blocks A to E

Building Block A

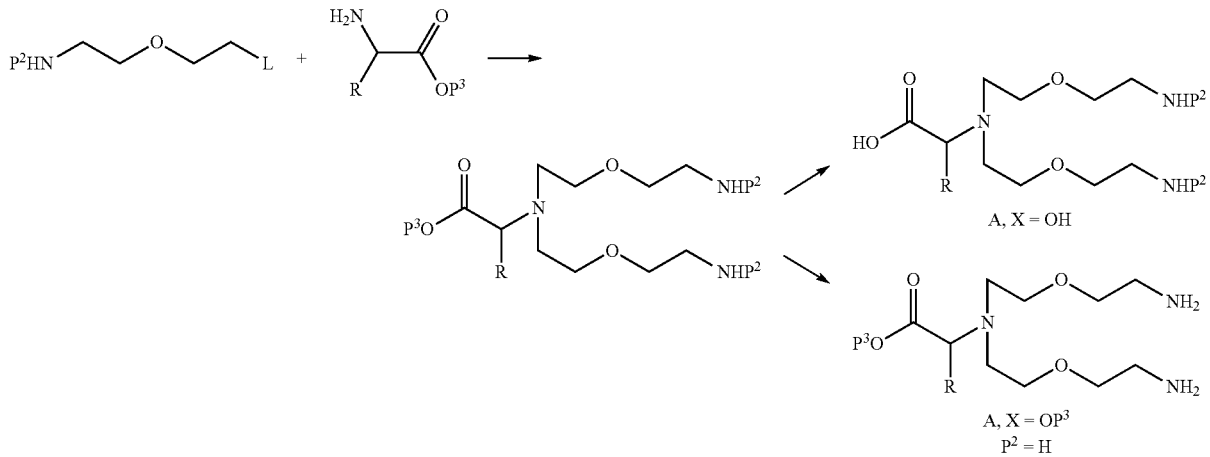

An amino acid with protection on the carboxylic acid and, if necessary, protection on the side chain (R) is reacted with a nitrogen protected aminoethoxyethyl species substituted with a suitable leaving group L such as a halide, mesylate, triflate or p-toluenesulfonate. The reaction requires the presence of a base such as a tertiary amine or inorganic base. Suitable bases include, but are not limited to, triethylamine, disopropylethylamine, potassium carbonate, cesium carbonate and sodium hydrogencarbonate. Suitable solvents include anhydrous, non-nucleophilic solvents which are able to dissolve at least one of the reactants, reagents or final product. Preferably, the suitable solvent is selected from methanol, THF, DMF, DCM, MeCN, DMSO, 1,4-dioxane and pyridine. A catalyst such as an iodide species may also be required for use in the reaction.

Protecting groups are removed separately. It is therefore essential that suitable conditions are used to result in the removal or either $P^3$ or $P^2$, but not both. For example, where $P^3$ is Bn and $P^2$ is Boc, for the removal of $P^3$ the starting material is dissolved in a suitable solvent and hydrogen and a hydrogenolysis catalyst such as palladium on carbon are added to give A (X=OH).

Alternatively, again where $P^2$ is Boc and $P^3$ is Bn, for the removal of $P^2$ the starting material is dissolved in a suitable solvent and an acid such as HCl, HBr or trifluoroacetic acid is added to give A (X=$OP^3$ and $P^2$=H). Other suitable acids for the removal of Boc include p-toluenesulfonic acid and sulfuric acid, which may be used safely on a larger scale.

The removal of protecting groups such as Boc or Bn are well known in the art (Greene, 1999, pp 415-419 and 518-525). Therefore, the choice of a suitable solvent for the removal of each would be known to a person skilled in the art.

Building Block B

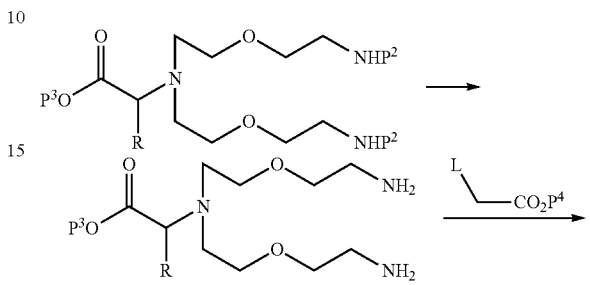

-continued

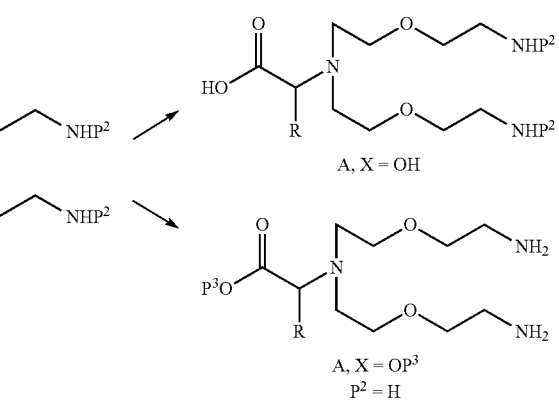

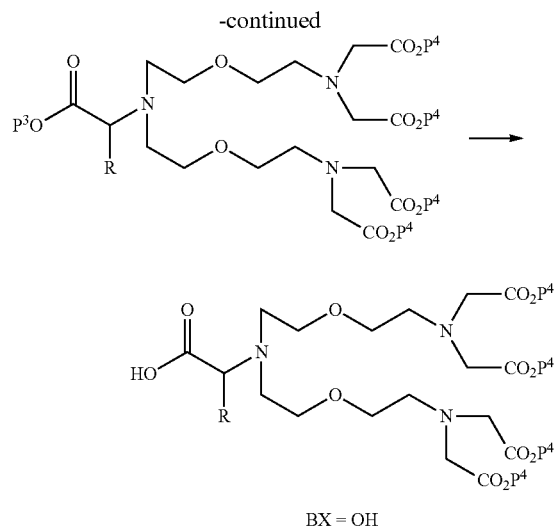

The $P^2$ protection group on a protected building block A is removed using conditions that are suitable to remove it and which do not remove $P^3$. For example, where $P^2$ is Boc and $P^3$ is Bn, the starting material is dissolved in a suitable solvent, the choice of which would be known to a person skilled in the art, and an acid such as HCl, HBr or trifluoroacetic acid is added.

The resulting bis-primary amine is alkylated four times with an acetate species with the carboxylic acid protected with $P^4$ and substituted with a suitable leaving group L such as a halide, mesylate or p-toluenesulfonate. The reaction should be done in a suitable solvent and requires the presence of a base such as a tertiary amine or inorganic base. Suitable solvents are as described for building block A. Suitable bases include, but are not limited to, triethylamine, disopropylethylamine, potassium carbonate, cesium carbonate and sodium hydrogencarbonate. The reaction may also require heating and/or a catalyst such as an iodide species, for example sodium iodide or potassium iodide.

Again, protecting group $P^3$ is removed using conditions that are suitable to remove it and which do not remove $P^4$. For example, where $P^3$ is Bn and $P^4$ is Cert-butyl, the starting material is dissolved in a suitable solvent, the choice of which would be known to a person skilled in the art, and hydrogen and a hydrogenolysis catalyst such as palladium on carbon are added to give B (X=OH).

Building Block C

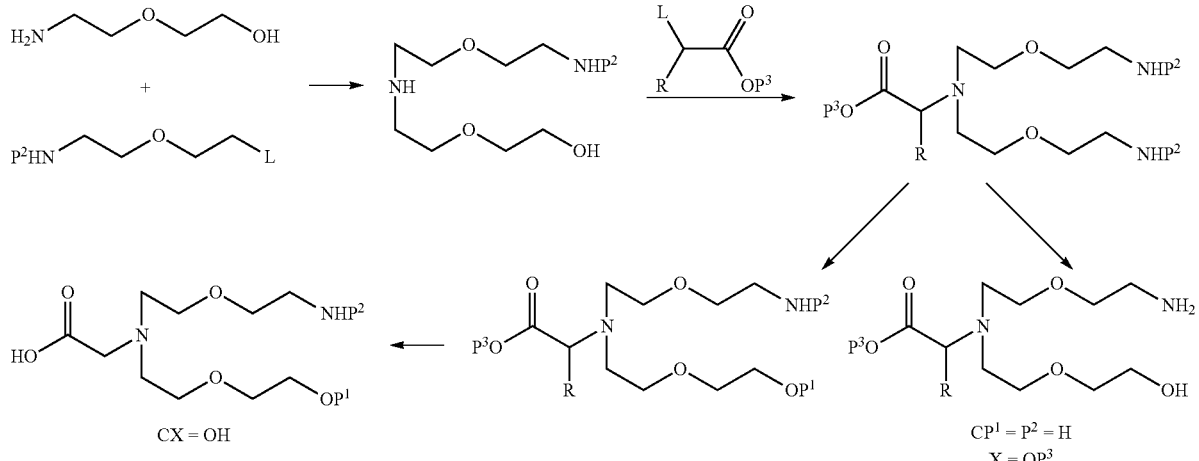

2-(2-Aminoethoxy)ethanol is reacted with a nitrogen protected aminoethoxyethyl species substituted with a suitable leaving group L such as a halide, mesylate, triflate or p-toluenesulfonate. The reaction should be done in a suitable solvent, and may require heating. Suitable solvents are as described for building block A. A catalyst such as an iodide species, for example sodium iodide or potassium iodide, may also be required. The resulting secondary amine is reacted by nucleophilic substitution of a leaving group alpha to an activated ester and if necessary, protection on any side chain (R).

A suitable protecting group may or may not be necessary to protect the free hydroxyl. The protecting group is introduced using established methods (Greene 1999). Suitable protecting groups for $P^1$ include acetate, substituted acetates, benzoate, trialkylsilyl, allyl, benzyl and others as described (Greene 1999). $P^1$ mayor may not have orthogonal reactivity to $P^2$ and $P^3$ Again, protecting group $P^3$ is removed using conditions that are suitable to remove it and which do not remove $P^2$. For example, where $P^3$ is Bn and $P^2$ is Boc, the starting material is dissolved in a suitable solvent, the choice of which would be known to a person skilled in the art, and hydrogen and a hydrogenolysis catalyst such as palladium on carbon are added to give C (X=OH).

Likewise, protecting group $P^2$ is removed using conditions that are suitable to remove it and which do not remove $P^3$. For example, where $P^2$ is Boc and $P^3$ is Bn, the starting material is dissolved in a suitable solvent, the choice of which would be known to a person skilled in the art, and an acid such as HCl, HBr or trifluoroacetic acid is added to give C ($P^1$=$P^2$=H and X=$OP^3$). Other suitable acids for the removal of Boc include p-toluenesulfonic acid and sulfuric acid, which may be used safely on a larger scale.

Building Block D

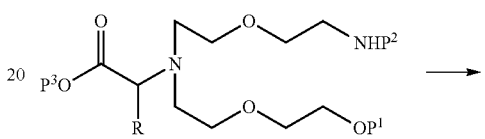

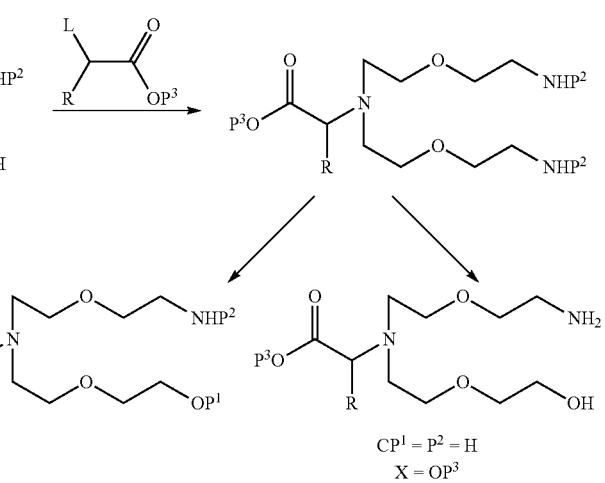

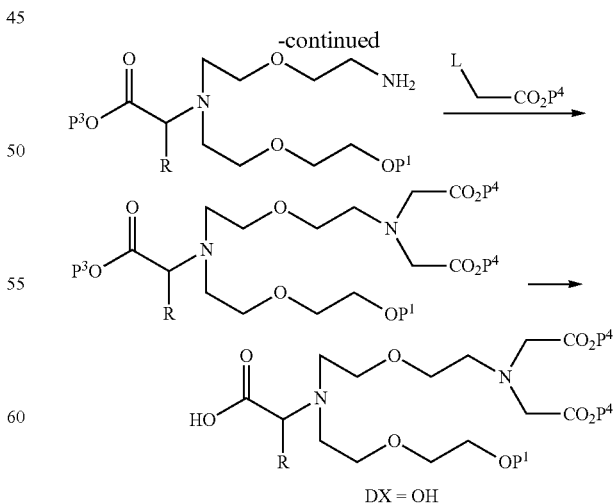

The $P^2$ protection group on a protected building block C is removed using conditions that are suitable to remove it and which do not remove P³ or P¹. For example, where P² is Boc and P³ is Bn and P¹ is acetate, the starting material is dissolved in a suitable solvent, the choice of which would be known to a person skilled in the art, and an acid such as HCl, HBr or trifluoroacetic acid is added.

The resulting primary amine is alkylated twice with an acetate species with the carboxylic acid protected with P⁴ and substituted with a suitable leaving group L such as a halide, mesylate or p-toluenesulfonate. The reaction should be done in a suitable solvent and requires the presence of a base such as a tertiary amine or inorganic base. Suitable solvents are as described for building block A. Suitable bases include, but are not limited to, triethylamine, disopropylethylamine, potassium carbonate, cesium carbonate and sodium hydrogencarbonate. The reaction may also require heating and/or a catalyst such as an iodide species, for example sodium iodide or potassium iodide.

Again, protecting group P³ is removed using conditions that are suitable to remove it and which do not remove P⁴ or P¹. For example, where P³ is Bn, P¹ is acetate and P⁴ is tert-butyl, the starting material is dissolved in a suitable solvent, the choice of which would be known to a person skilled in the art, and hydrogen and a hydrogenolysis catalyst such as palladium on carbon are added to give D (X=OH).

Building Block E

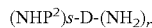

Building blocks E are prepared by the reaction of a di-, tri- or tetra-amine with sub-stoichiometric amounts of a reagent to result in partial protection of the amino groups with protecting group P². For example, reaction with di-tert-butyl dicarbonate in the presence of a base and in a suitable solvent provides the partially Boc protected species. Suitable solvents are as described for building block A. Discrete products can then be obtained from the resultant mixture by the use of silica chromatography.

Dendrimer Synthesis

The synthesis of the dendrimers involves combination of the building blocks described above. This is done in a stepwise fashion. The unprotected amine(s) of one building block is coupled with the unprotected carboxylic acid of another building block. The dendrimer can either be built up from the centre out (divergent synthesis) or more preferably from the outside in (convergent synthesis). Each coupling step can be followed by a deprotection step. This alternation of coupling and deprotection is continued until the desired dendrimer is synthesised.

The coupling step is carried out in an anhydrous solvent in the presence of a non-nucleophilic base. Suitable solvents for use in the coupling step include DMF, DMSO or acetonitrile. Preferably the solvent is anhydrous, however water may also be employed. Suitable non-nucleophilic bases are N-methylmorpholine, triethylamine, pyridine, or DIPEA.

A coupling agent or mixture of agents is then added, such as HBTU, NHS, Benzotriazol-1-yloxy)tripyrrolidinophosphoniumhexafluorophosphate (PyBOP), N,N' Dicyclohexylcarbodiimide (DCC) or N-(3-Dimethylaminopropyl)-N'-ethylcarbodiimide (EDC). These include some of the more popular reagents for use in this reaction, however, there is a vast library of suitable reagents which may be employed in this reaction and which would be known to a person skilled in the art (Montalbetti, 2005).

The reaction is generally carried out at ambient temperatures but can be warmed or cooled.

In the convergent synthetic approach, the next step is deprotection of the carboxylic acid. For example, where P³ is Bn, the material is dissolved in a suitable solvent and hydrogen and a hydrogenolysis catalyst such as palladium on carbon are added. The product can then be coupled with the unprotected amine on another building block as described above.

In the divergent synthetic approach, the next step is deprotection of the amines. For example, where P² is Boc, the material is dissolved in a suitable solvent and an acid such as HCl, HBr or trifluoroacetic acid is added. The product can then be coupled with the unprotected carboxylic acid on another building block as described above.

As indicated previously, suitable reagents for the removal of protecting groups such as Bn Boc are well known in the art (Greene, 1999).

An amino terminated dendrimer can be converted to a carboxylic acid terminated dendrimer by reaction with succinic anhydride in a solvent in the presence of a base. Preferably, non-nucleophilic solvents and bases are employed. Suitable solvents include, but are not limited to, water and DMSO. Other suitable solvents would be known to a person skilled in the art. Suitable bases include, but are not limited to, DIPEA, triethylamine, pyridine and N-methylmorpholine. Other suitable bases would be known to a person skilled in the art.

A number of dendrimer structures have been the subject of publications and/or patent applications; however there are very few examples where the purity of these dendrimer products has been measured by high performance liquid chromatography (HPLC) methods. This method of purity measure is the industry standard for release of pharmaceutical intermediates and ingredients. The synthesis of SPL7013 uses HPLC to control the process and analyse the final product to demonstrate that the material is primarily a single molecular entity (McCarthy 2005). HPLC analysis of commercially available poly(amido amine) (PAMAM) dendrimers showed that they required further purification (Mullen 2012). Numerous other publications demonstrate dendrimer purity by MALDI and size-exclusion chromatography methods, but these methods are unlikely to meet regulatory requirements for demonstration of process control and product purity.

The dendrimers described in this invention have been made by a process controlled by regular HPLC analysis for purity, resulting in high purity products as shown by the following examples.

Use of Dendrimers

The dendrimers of the present invention provide a convenient scaffold or tool which may act as carriers for active agents which may be attached to, or encapsulated within, the dendrimers.

As a carrier of active agents, the elaborated dendrimers of the present invention can improve the bioavailability of the active agents because they solubilise insoluble actives and/or stop actives from being cleared too fast. They can also provide a delivery mechanism for the active agents to allow for the treatment or prevention of various diseases or conditions. By attachment to, or encapsulation within, a dendrimer of the present invention, the active agent may be beneficially modified to act as a slow release or targeting active agent. Co-delivery of two or more active agents to the same location may also be achieved. The dendrimers may also be used to effect sustained release of a therapeutic agent so as to offer a larger therapeutic window.

Active agents for use in imaging may also be attached to, or encapsulated within, the elaborated dendrimers of the present invention.

Attachment of active agents is achieved by covalent interactions between the active agent and the amine of carboxylic acid of the dendrimers of the present invention to form amide or ester linkages (Montalbetti, 2005). Alternatively, a linker moiety can be inserted between the active agent and the dendrimer. Where the active agents are encapsulated, non-covalent interactions are involved and have been described by Risch (1995).

Suitable active agents include therapeutic agents and imaging agents. Examples of therapeutic agents which may be attached to the dendrimers of the present invention include anti-cancer agents such as taxol, doxorubicin, and paclitaxel. The dendrimers may also be used to administer analgesic and anti-inflammatory agents such as ibuprofen, celebcoxib, indomethacin, naproxen, diclofenac, morphine and codeine or targeting agents such as folate. Examples of drugs which may be encapsulated within the dendrimers of the present invention include camptothecin (Morgan, 2006) and methotrexate (Kojima, 2000) for the treatment of cancer, primaquine (Bhadra, 2005) for the treatment of malaria and analgesics such as naproxen sodium (Mucalo, 2012). Anti-malarial drugs suitable for use with the dendrimers of the present invention may also include doxycycline, mefloquine and quinine. A more comprehensive list of active agents can be obtained from the British, European and United States Pharmacopeias (2013).

A wide variety of antibiotics from classes such as penicillins, sulfonamides, macrolides, tetracyclines, quinolones, cephalosporins, aminoglycosides and glycopeptides may also be attached or encapsulated within the dendrimers of the present invention. Likewise, anti-virals such as oseltamivir, acyclovir, abacavir and interferon may also be attached to, or encapsulated within, the dendrimers of the present invention.

Examples of suitable imaging agents which may be attached to dendrimers of the present invention include lanthanide complexes such as gadolinium diethylenetriaminepentacetate (Gd-DTPA), gadodiamide, gadofosveset and gadoxetic acid, and fluorophores.

Other suitable active agents for use with the dendrimers of the present invention will be known to those skilled in the art.

The dendrimers of the present invention may also be converted into therapeutic agents themselves by the attachment of inactive agents. Examples of suitable inactive agents for such conversion include mono- or oligo-saccharides for multivalent presentation, anionic species used for binding, agents required for boron neutron capture therapy (BNCT) such as 4-boronophenylalanine (BPA) and also gadolinium neutron capture therapy (GdNCT). Other suitable inactive agents will be known to those skilled in the art.

In a second aspect, the present invention provides a method for the manufacture of a therapeutic composition, the method including the steps of adding an active agent to a dendrimer of formula (I). The addition of the active agent is achieved by either attachment, or encapsulation within, of the active agent to the dendrimer. Again, attachment of the active agent makes use of covalent interactions while encapsulation makes use of non-covalent interactions.

Thus, in a third aspect, the present invention includes a compound of formula (I) together with an active agent attached to, or encapsulated within, the compound of formula (I).

In a fourth aspect, the present invention includes a pharmaceutical composition comprising a compound of formula (I) together with an active agent attached to, or encapsulated within, the compound of formula (I) together with suitable carriers and/or excipients. Suitable carriers for use in the present invention include liposomes, microspheres, nanoparticles, protein conjugates, antibodies and virosomes. A wide variety of excipients may be used according to those outlined in Rowe (2012).

EXAMPLES

General Experimental

Analytical TLC was carried out on pre-coated 0.25 mm thick Merck 60 $F_{254}$ silica gel plates and visualization was by thermal development after dipping in potassium permanganate in dilute sodium hydroxide. Flash column chromatography was conducted using silica gel 60 (40-60 μm). Analytical RP-HPLC was conducted on a Kinetex 2.6 μm, C18, 100 Å, 100×3 mm column eluting with 0.1% formic acid in water/methanol gradients. $^{1}$H and $^{13}$C NMR spectra were recorded at 500 MHz and 126 MHz respectively and run in $CDCl_3$ with TMS as an internal standard unless otherwise stated; J values are given in Hz. Mass spectra were recorded on a Water Micromass Q-Tof Premier(ESI) mass spectrometer. Dendrimers were named according to the recommendations set out by Friedhoven and Vögtle, 2006.

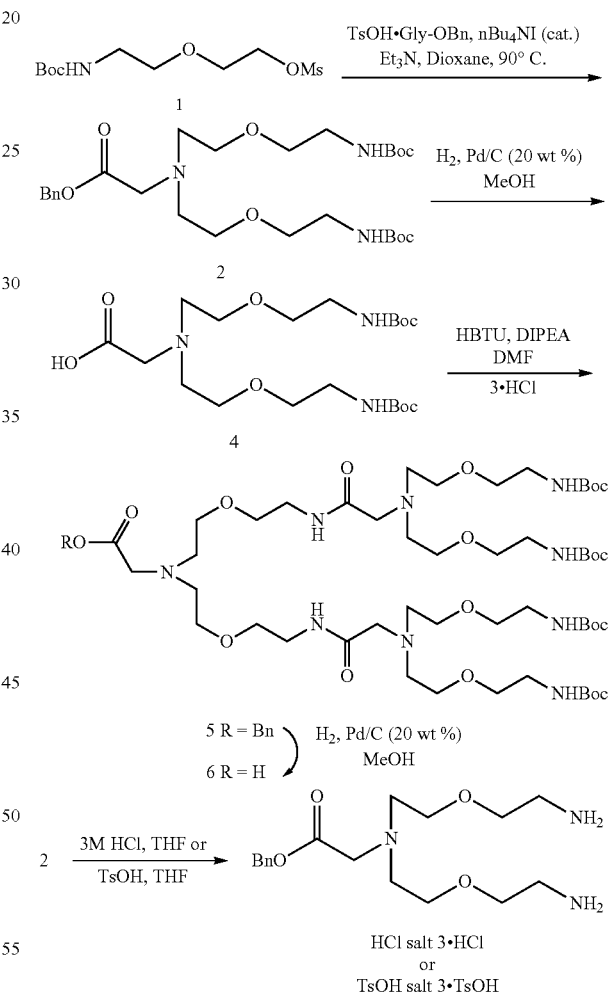

Synthesis and Use of an Example of Building Block A

Benzyl 2-[bis[2-[2-(tert-butoxycarbonylamino)ethoxy]ethyl]amino]acetate, 2

Benzyl glycinate p-toluenesulfonate (0.4 g, 1.2 mmol) was co-evaporated with toluene (3×2 mL) and dried in vacuo. A solution of 2-[2-(tert-butoxycarbonylamino)ethoxy]ethyl methanesulfonate (1) (Kim 2001) (0.84 g, 3.0 mmol) in dry 1,4-dioxane (2.0 mL, 23.0 mmol) was added. n-Tetrabutylammonium iodide (0.11 g, 0.3 mmol) and triethylamine (0.83 mL, 6.0 mmol) were added at 20° C. before the reaction mixture was heated to 90° C. for 24 hours. The reaction mixture was cooled to 20° C. and diluted with water (30 mL) before being extracted into ethyl acetate (2×30 mL). The combined organic phases were washed with water (50 mL) and brine (50 mL). The organic phase was dried ($Na_2SO_4$), filtered and concentrated to a dark orange oil 2 (0.28 g, 90% yield, >95% purity by HPLC). $^{13}C$ NMR ($CD_3OD$) δ 171.6, 157.0, 136.1, 128.1, 128.0, 127.9, 78.6, 69.4, 69.1, 65.8, 55.5, 53.9, 39.9, 27.4. ESMS ($C_{27}H_{45}N_3O_8$) [M+Na]$^+$ calc. 562.3104. found 562.3099.

Benzyl 2-(bis(2-(2-aminoethoxy)ethyl)amino)acetate, trihydrochloride, 3.HCl

Aqueous hydrochloric acid (3M, 16 mL) was added to a solution of benzyl 2-[bis[2-[2-(tert-butoxycarbonylamino)ethoxy]ethyl]amino]acetate (2) (0.83 g, 1.5 mmol) in tetrahydrofuran (4 mL) and stirred for one hour. The reaction mixture was co-evaporated with toluene (3×20 mL) and dried under high vacuum to give a viscous yellow oil (0.69 g). This hydrochloride salt (3) was used without further purification. $^{13}C$ NMR ($D_2O$) δ 166.7, 134.5, 129.2, 129.1, 129.0, 68.9, 66.7, 64.4, 55.0, 54.2, 39.0. ESMS ($C_{17}H_{29}N_3O_4$) [M+H]$^+$ calc. 340.2236. found 340.2230.

Benzyl 2-(bis(2-(2-aminoethoxy)ethyl)amino)acetate, tri(p-toluenesulfonate), 3.TsOH p-Toluenesulfonic acid monohydrate (5.02 g, 25.3 mmol, 3.3 eq.) was added to a solution of benzyl 2-[bis[2-[2-(tert-butoxycarbonylamino)ethoxy]ethyl]amino]acetate (2) (4.14 g, 7.67 mmol, 1.0 eq.) in tetrahydrofuran (25 mL) and stirred for 30 minutes at 50° C. The reaction mixture was concentrated in vacuo producing white solid. The crude product was dissolved in ethanol (100 mL) at approximately 45° C. Ethyl acetate (50 mL) was added and the mixture was slowly cooled to 7° C. and left for 18 h. The resultant crystals were washed with ethyl acetate (50 mL) before being dried under vacuum to give the product (5.18 g, 79%). $^{13}C$ NMR ($CD_3OD$) δ 167.5, 143.4, 142.0, 136.2, 130.0, 129.9, 129.8, 127.0, 69.4, 68.1, 66.0, 56.2, 55.5, 40.4, 21.3.

2-[Bis[2-[2-(tert-butoxycarbonylamino)ethoxy]ethyl]amino]acetic acid, 4

A solution of benzyl 2-[bis[2-[2-(tert-butoxycarbonylamino)ethoxy]ethyl]amino]acetate (2) (2.2 g, 4.1 mmol) in methanol (70 mL) was degassed by bubbling argon through solution for five minutes. Palladium (10%) on activated carbon (220 mg) was added to the solution and the reaction mixture was placed under an atmosphere of hydrogen. The reaction was allowed to stir at 15° C. for 15 h before being filtered through a pad of Celite. The Celite was washed with methanol (2×20 mL) and the combined filtrates were concentrated at reduced pressure to provide a colourless oil (1.69 g, 3.8 mmol, 92%, >95% purity by HPLC). The product (4) was used without further purification. $^{13}C$ NMR ($CD_3OD$) δ 170.1, 158.5, 80.2, 71.5, 65.9, 58.4, 55.8, 41.2, 28.8. ESMS ($C_{20}H_{39}N_3O_8$) [M+Na]$^+$ calc. 472.2635. found 472.2623.

Benzyl-2-aminoacetate(N,N):{6,9-diaza-3-oxa-7-oxononanyl(9,9)}$_{2x}^{G1}$:(6-aza-9,9-dimethyl-3,8-dioxa-7-oxodecanyl)$_4$-cascadane, 5

N,N-Diisopropylethylamine (18 mL, 102 mmol) was added to a mixture of benzyl 2-[bis[2-(2-aminoethoxyl)ethyl]amino]acetate trihydrochloride (3.HCl) (4.57 g, 10.2 mmol) in dry DMF (60 mL). A solution of carboxylic acid 4 (10.01 g, 22.27 mmol) in dry DMF (80 ml) was added and the resulting mixture was stirred at 20° C. N,N,N',N'-Tetramethyl-O-(1H-benzotriazol-1-yl)uroniumhexafluorophosphate (8.95 g, 22.4 mmol) was added in one solid portion and stirring was continued for 17 hours. The reaction was diluted with water (300 mL) and extracted into ethyl acetate (2×300 mL). The combined organic phases were washed with saturated aqueous sodium hydrogencarbonate (1×500 mL), water (1×500 mL) and brine (2×500 mL) before being dried ($Na_2SO_4$), filtered and concentrated to provide the 5 as an orange oil (12 g, 98%, 95% purity by HPLC). The product was used without further purification. $^{13}C$ NMR ($CD_3OD$) δ 175.0, 173.1, 158.4, 137.6, 129.7, 129.5, 129.4, 80.2, 79.5, 71.1, 71.0, 70.7, 70.5, 67.2, 60.3, 57.1, 56.4, 55.4, 41.4, 39.9, 38.9, 28.9.

2-Aminoacetic acid(N,N):{6,9-diaza-3-oxa-7-oxononanyl(9,9)}$_{2x}^{G1}$:(6-aza-9,9-dimethyl-3,8-dioxa-7-oxodecanyl)$_4$-cascadane, 6

A solution of 5 (13.3 g, 11.1 mmol) in methanol (300 mL) was degassed by bubbling argon through solution for five minutes. Palladium (10%) on activated carbon (0.65 g) was added to the solution and the reaction mixture was placed under an atmosphere of hydrogen. The reaction was allowed to stir at 15° C. for 15 hours before being filtered through a glass fibre filter. The filter was washed with methanol (2×20 mL) and the combined filtrates were concentrated at reduced pressure to provide carboxylic acid 6 as a colourless oil (10.5 g, 85%, 90% purity by HPLC). The product was used without further purification. $^{13}C$ NMR ($CD_3OD$) δ 174.9, 171.0, 158.4, 80.1, 71.2, 71.1, 70.2, 66.5, 60.1, 58.7, 56.2, 55.9, 41.4, 39.7, 39.0, 28.9.

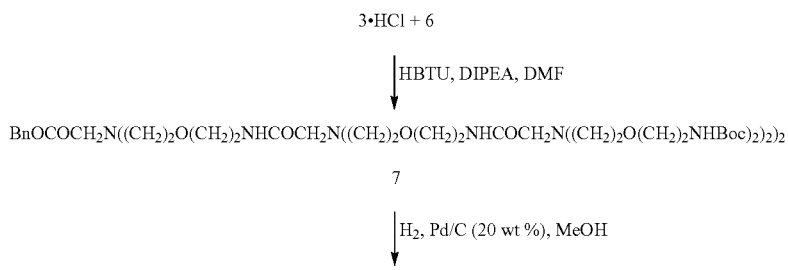

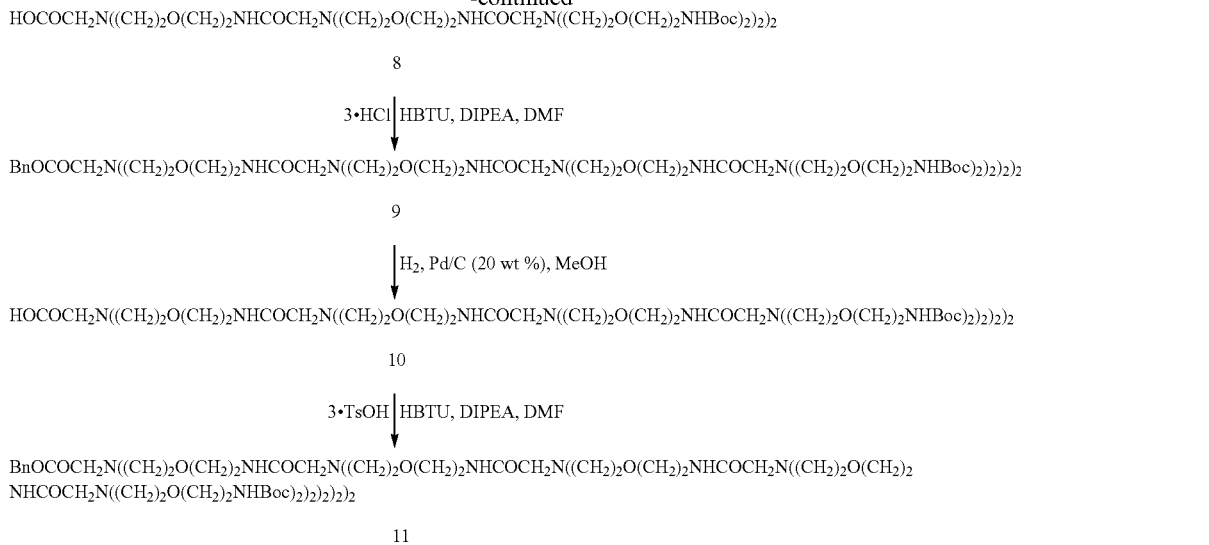

Synthesis of Examples of Dendrimers Containing Only Building Block A

Benzyl-2-aminoacetate(N,N):{6,9-diaza-3-oxa-7-oxononanyl(9,9)}$_{2x,4x}^{G1,G2}$ ⊛ 6-aza-9,9-dimethyl-3,8-dioxa-7-oxodecanyl)$_8$-cascadane, 7

N,N-Diisopropylethylamine (7.45 mL, 42.3 mmol) was added to a mixture of benzyl 2-[bis[2-(2-aminoethoxyl)ethyl]amino]acetate trihydrochloride 3.HCl (1.9 g, 4.20 mmol) in dry DMF (20 mL). A solution of carboxylic acid 6 (10.4 g, 9.31 mmol) in dry DMF (40 ml) was added and the resulting mixture was stirred at 20° C. N,N,N',N'-Tetramethyl-O-(1H-benzotriazol-1-yl)uroniumhexafluorophosphate (3.60 g, 9.31 mmol) was added in one solid portion and stirring was continued for 18 hours. The reaction was diluted with saturated aqueous sodium hydrogencarbonate (200 mL) and extracted into ethyl acetate (2×200 mL). The combined organic phases were washed with water (2×500 mL) and brine (1×500 mL) before being dried (Na$_2$SO$_4$), filtered and concentrated to provide an orange oil (11.7 g). The crude product was purified on silica gel (220 g) eluting with a gradient from 1% to 7% methanolic ammonia (7M) in dichlorormethane. Purified 7 was isolated as a pale yellow oil (9.8 g, 92%, 90% purity by HPLC). $^{13}$C NMR (CD$_3$OD) δ174.9, 174.6, 173.0, 158.4, 137.6, 129.7, 129.4, 80.1, 79.5, 71.1, 70.7, 70.5, 70.4, 67.2, 60.3, 57.1, 56.3, 56.2, 55.5, 41.4, 39.9, 28.9.

2-Aminoacetic acid(N,N):{6,9-diaza-3-oxa-7-oxononanyl(9,9)}$_{2x,4x}^{G1,G2}$ ⊛ 6-aza-9,9-dimethyl-3,8-dioxa-7-oxodecanyl)$_8$-cascadane, 8

A solution of 7 (6.8 g, 2.7 mmol) in methanol (150 mL) was degassed by bubbling argon through solution for five minutes. Palladium (10%) on activated carbon (0.35 g) was added to the solution and the reaction mixture was placed under an atmosphere of hydrogen. The reaction was allowed to stir at 15° C. for 18 hours before being filtered through a glass fibre filter. The filter was washed with methanol (2×20 mL) and the combined filtrates were concentrated at reduced pressure to provide carboxylic acid 8 as a colourless oil (5.9 g, 90%, 90% purity by HPLC). The product was used without further purification. $^{13}$C NMR (CD$_3$OD) δ 174.9, 174.7, 170.5, 158.4, 80.1, 71.1, 70.7, 70.4, 66.5, 60.2, 60.1, 58.6, 56.2, 56.1, 55.8, 42.6, 41.4, 39.9, 39.7, 28.9.

Benzyl-2-aminoacetate(N,N):{6,9-diaza-3-oxa-7-oxononanyl(9,9)}$_{2x,4x,8x}^{G1,G2,G3}$ ⊛ 6-aza-9,9-dimethyl-3,8-dioxa-7-oxodecanyl)$_{16}$-cascadane, 9

N,N-Diisopropylethylamine (1.76 mL, 10.0 mmol) was added to a mixture of benzyl 2-[bis[2-(2-aminoethoxyl)ethyl]amino]acetate trihydrochloride 3.HCl (0.45 g, 1.0 mmol) in dry DMF (16 mL). A solution of carboxylic acid 8 (5.36 g, 2.2 mmol) in dry DMF (20 ml) was added and the resulting mixture was stirred at 20° C. N,N,N',N'-Tetramethyl-O-(1H-benzotriazol-1-yl)uroniumhexafluorophosphate (0.85 g, 2.2 mmol) was added in one solid portion and stirring was continued for 18 hours. The reaction was diluted with saturated aqueous sodium hydrogencarbonate (100 mL) and extracted into ethyl acetate (2×100 mL). The combined organic phases were washed with water (1×200 mL) and brine (2×200 mL) before being dried (Na$_2$SO$_4$), filtered and concentrated to provide 9 as an orange oil (5.9 g, 98%, 78% purity by HPLC). The product was used without further purification. $^{13}$C NMR (CD$_3$OD) δ174.9, 174.5, 173.1, 158.4, 137.7, 129.8, 129.5, 80.1, 71.1, 70.8, 70.5, 70.4, 67.2, 60.3, 57.1, 56.3, 56.1, 55.5, 41.4, 40.0, 29.0.

2-Aminoacetic acid(N,N):{6,9-diaza-3-oxa-7-oxononanyl(9,9)}$_{2x,4x,8x}^{G1,G2,G3}$ ⊛ 6-aza-9,9-dimethyl-3,8-dioxa-7-oxodecanyl)$_{16}$-cascadane, 10

A solution of 9 (2.20 g, 0.43 mmol) in methanol (50 mL) was degassed by bubbling argon through solution for five minutes. Palladium (10%) on activated carbon (0.11 g) was added to the solution and the reaction mixture was placed under an atmosphere of hydrogen. The reaction was allowed to stir at 25° C. for 2.5 hours before being filtered through a glass fibre filter. The filter was washed with methanol (2×20 mL) and the combined filtrates were concentrated at reduced pressure to provide carboxylic acid 10 as a colourless oil (1.95 g, 90%, 63% purity by HPLC). The product was used without further purification. $^{13}$C NMR (CD$_3$OD) δ 174.8, 174.6, 164.9, 158.3, 80.1, 79.5, 71.1, 70.8, 70.3, 66.6, 60.2, 60.1, 56.2, 56.1, 55.9, 42.7, 41.4, 40.0, 39.7, 39.7, 29.0.

Benzyl-2-aminoacetate(N,N):{6,9-diaza-3-oxa-7-oxononanyl(9,9)}$_{2x,4x,8x,16x}^{G1,G2,G3,G4}$ ⊗ 6-aza-9,9-dimethyl-3,8-dioxa-7-oxodecanyl)$_{32}$-cascadane, 11

Benzyl 2-[bis[2-(2-aminoethoxyl)ethyl]amino]acetate tri (p-toluenesulfonate) 3.TsOH (11 mg, 0.013 mmol) was added to a solution of N,N-diisopropylethylamine (23 μL, 0.13 mmol) and carboxylic acid 10 (140 mg, 0.028 mmol) in dry DMF (3 mL). N,N,N',N'-Tetramethyl-O-(1H-benzotriazol-1-yl)uroniumhexafluorophosphate (11 mg, 0.028 mmol) was added in one solid portion and the reaction stirred at room temperature for 1 hour. The reaction was diluted with water (25 mL) and extracted into ethyl acetate (3×25 mL). The combined organic phases were washed with brine (100 mL) before being dried (Na$_2$SO$_4$), filtered and concentrated. The residue was purified by flash silica chromatography eluting with 1-5% methanolic ammonia in DCM to provide 11 as a colourless oil (45 mg, 33%). $^{13}$C NMR (CD$_3$OD) δ174.8, 174.5, 173.1, 158.3, 137.7, 129.8, 129.5, 80.1, 71.1, 70.8, 70.7, 70.5, 70.4, 67.2, 60.3, 56.3, 56.1, 41.4, 40.0, 29.0. ESMS deconvoluted (C$_{476}$H$_{913}$N$_{33}$O$_{158}$) calc. 10,468.0. found 10,468.5.

a colourless oil (26 mg). $^{13}$C NMR (D$_2$O) S 170.4, 169.7, 69.1, 68.9, 66.5, 66.3, 64.6, 56.7, 56.4, 54.9, 54.5, 54.4, 39.1, 38.9.

2-Aminoacetic acid(N,N):{6,9-diaza-3-oxa-7-oxononanyl(9,9)}$_{2x,4x,8x}^{G1,G2,G3}$:(6-aza-3,11-dioxa-7,10-dioxoundecanyl)$_{16}$-cascadane, 13

Pyridine (5.5 mL) was added to a stirred solution of 12 (16×NH$_2$, 1×COOH) (0.5 g, 0.11 mmol) in a mixture of DMSO (8 mL) and water (2 mL). Solid succinic anhydride (2.74 g, 27.1 mmol) was added in one portion and the reaction mixture was stirred for 18 hours at 15° C. The reaction mixture was then diluted with water (30 mL) before a portion of the reaction mixture (20 mL) was subjected to centrifugal ultrafiltration (1 kDa cut off, 5000 g, 10 h per pass). The retentate was diluted with injection water (10 mL) and centrifuged for a further 10 hours. The process was repeated with water then using two portions of aqueous sodium hydrogencarbonate (0.2 M, 10 mL) followed by a further two portions of water for injection. The retentate (3 mL) was evaporated at reduced pressure to provide the product 13 (17×COOH) as a pale yellow oil (196 mg, 63% purity by HPLC). $^{13}$C NMR (D$_2$O) δ 176.0, 174.1, 69.3, 68.9, 68.9, 68.4, 64.8, 58.1, 58.0, 54.6, 54.3, 54.2, 39.0, 38.8, 38.7, 33.2, 32.5.

HOCOCH$_2$N((CH$_2$)$_2$O(CH$_2$)$_2$NHCOCH$_2$N((CH$_2$)$_2$O(CH$_2$)$_2$NHCOCH$_2$N((CH$_2$)$_2$O(CH$_2$)$_2$NHCOCH$_2$N((CH$_2$)$_2$O(CH$_2$)$_2$NHBoc)$_2$)$_2$)$_2$)$_2$

10

HOCOCH$_2$N((CH$_2$)$_2$O(CH$_2$)$_2$NHCOCH$_2$N((CH$_2$)$_2$O(CH$_2$)$_2$NHCOCH$_2$N((CH$_2$)$_2$O(CH$_2$)$_2$NHCOCH$_2$N((CH$_2$)$_2$O(CH$_2$)$_2$NH)$_2$)$_2$)$_2$)$_2$

12

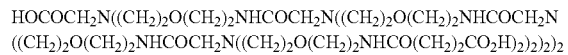

HOCOCH$_2$N((CH$_2$)$_2$O(CH$_2$)$_2$NHCOCH$_2$N((CH$_2$)$_2$O(CH$_2$)$_2$NHCOCH$_2$N((CH$_2$)$_2$O(CH$_2$)$_2$NHCOCH$_2$N((CH$_2$)$_2$O(CH$_2$)$_2$NHCO(CH$_2$)$_2$CO$_2$H)$_2$)$_2$)$_2$)$_2$

13

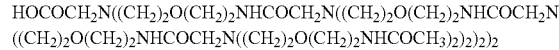

HOCOCH$_2$N((CH$_2$)$_2$O(CH$_2$)$_2$NHCOCH$_2$N((CH$_2$)$_2$O(CH$_2$)$_2$NHCOCH$_2$N((CH$_2$)$_2$O(CH$_2$)$_2$NHCOCH$_2$N((CH$_2$)$_2$O(CH$_2$)$_2$NHCOCH$_3$)$_2$)$_2$)$_2$)$_2$

14

Modifying the Termini of Dendrimers Containing Only Building Block A

2-Aminoacetic acid(N,N):{6,9-diaza-3-oxa-7-oxononanyl(9,9)}$_{2x,4x,8x}^{G1,G2,G3}$ ⊗ 6:(5-amino-3-oxapentanyl)$_{16}$-cascadane, 12

Aqueous hydrochloric acid (40 mL) was added to a solution of carboxylic acid 10 (1.8 g, 0.35 mmol) in THF (10 mL). The mixture was stirred at 40° C. for 18 hours. The reaction mixture was concentrated at reduced pressure to give a viscous colourless oil. The residue was co-evaporated with water (3×5 mL) at reduced pressure to provide 12 (16×NH$_2$, 1×COOH) (1.5 g, 92%). A portion (50 mg) of the product was subjected to centrifugal ultrafiltration (1 kDa cut off, 5000 g, 10 h per pass) with injection water (4×10 mL). The retentate was concentrated at reduced pressure to provide purified 12 as

2-Aminoacetic acid(N,N):{6,9-diaza-3-oxa-7-oxononanyl(9,9)}$_{2x,4x,8x}^{G1,G2,G3}$:(6-aza-3-oxa-7-oxooctanyl)$_{16}$-cascadane, 14

N,N-Diisopropylethylamine (1.2 mL, 6.5 mmol) was added to a stirred solution of 12 (16×NH$_2$, 1×COOH) (70 mg, 0.015 mmol) in a mixture of DMSO (4 mL) and water (1 mL). Acetic anhydride (0.53 mL, 3.8 mmol) was added in one portion and the reaction mixture was stirred for 18 hours at 25° C. The reaction mixture was then diluted with water (15 mL) before a portion of the reaction mixture (15 mL) was subjected to centrifugal ultrafiltration (1 kDa cut off, 5000 g, 10 h per pass) with injection water (4×10 mL). The retentate was concentrated at reduced pressure to provide the product as a colourless oil (23 mg, 60% purity by HPLC). $^{13}$C NMR (D$_2$O) δ 174.1, 172.7, 69.3, 68.9, 67.9, 67.7, 64.5, 57.7, 57.5, 54.7, 54.5, 54.3, 39.1, 38.8, 22.0.

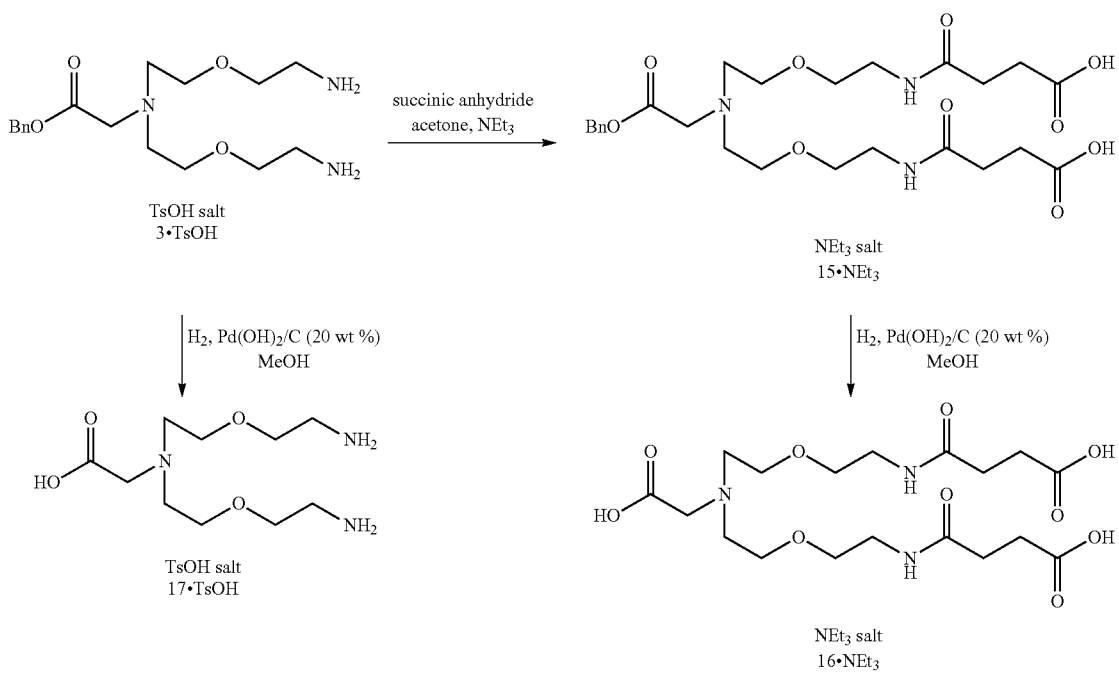

Conversion of Dendrimers to Alternately Functionalised or Protected Forms

Benzyl 2-[bis[2-[2-(3-carboxypropanamido)ethoxy]ethyl]amino]acetate, triethylammonium salt, 15.NEt₃

Succinic anhydride (55 mg, 0.54 mmol, 4.8 eq.) was added to a solution of benzyl 2-(bis(2-(aminomethoxy)ethyl)amino)acetate, tri(p-toluenesulfonate) (3.TsOH) (97 mg, 0.11 mmol, 1 eq.) in acetone (1 mL) and triethylamine (200 μL) and the reaction mixture was stirred at room temperature for 18 h. The solvents were removed in vacuo. The crude residue was purified by silica column chromatography eluting with methanol in chloroform (0-30%) to give 64 mg (88%) of 15.NEt₃ as a colourless oil. $^{13}$C NMR (CD₃OD) δ 178.7, 175.3, 173.2, 137.5, 129.6, 129.5, 129.4, 70.6, 70.2, 67.4, 56.8, 55.5, 47.6, 40.3, 32.7, 32.3, 9.2. ESMS (C₂₅H₃₆N₃O₁₀) [M−H]⁻ calc. 538.2406. found 538.2400.

2-[Bis[2-[2-(3-carboxypropanamido)ethoxy]ethyl]amino]acetic acid, triethylammonium salt, 16.NEt₃

A solution of benzyl 2-[bis[2-[2-(3-carboxypropanamido)ethoxy]ethyl]amino]acetate, triethylammonium salt (15.NEt₃) (62 mg, 0.11 mmol) in methanol (2 mL) was degassed by repeated pump-purge (argon) cycles. Palladium hydroxide (20%) on activated carbon (10 mg) was added to the solution and the reaction mixture was placed under an atmosphere of hydrogen. The reaction was allowed to stir at room temperature for 5 h before being filtered through a pad of Celite. The Celite was washed with methanol (2×20 mL) and the combined filtrates were concentrated at reduced pressure to give 49 mg (95%) of 16.NEt₃ as a colourless oil. $^{13}$C NMR (CD₃OD) δ 178.7, 178.2, 175.5, 171.2, 71.0, 66.2, 58.2, 56.0, 47.6, 40.2, 32.5, 32.2, 32.1, 9.2. ESMS (C₁₈H₃₀N₃O₁₀) [M−H]⁻ calc. 448.1937. found 448.1930.

2-(Bis(2-(2-aminoethoxyl)ethyl)amino)acetic acid, tri(p-toluenesulfonate), 17.TsOH A solution of benzyl 2-(bis(2-(aminomethoxy)ethyl)amino)acetate, tri(p-toluenesulfonate) (3.TsOH) (103 mg, 0.12 mmol, 1 eq.) in methanol (3 mL) was degassed by repeated pump-purge (argon) cycles. Palladium hydroxide (20%) on activated carbon (10 mg) was added to the solution and the reaction mixture was placed under an atmosphere of hydrogen. The reaction was allowed to stir at room temperature for 18 h before being filtered through a pad of Celite. The Celite was washed with methanol (2×20 mL) and the combined filtrates were concentrated at reduced pressure to give 91 mg (95%) of 17.TsOH as a white solid. $^{13}$C NMR (CD₃OD) δ 170.4, 143.5, 141.9, 129.9, 126.9, 68.0, 66.1, 57.0, 56.9, 40.5, 21.3. ESMS (C₁₀H₂₄N₃O₄) [M+H]⁺ calc. 250.1767. found 250.1772.

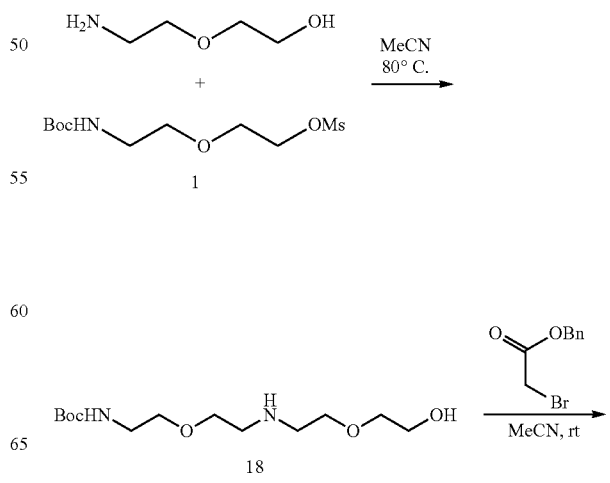

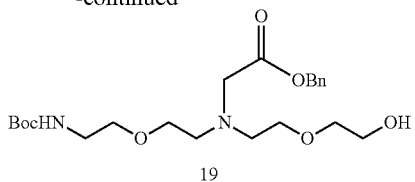

19

Synthesis of an Example of Building Block C tert-Butyl (2-(2-((2-(2-hydroxyethoxyl)ethyl)amino)ethoxy)ethyl)carbamate, 18

2-(2-Aminoethoxyl)ethanol (0.7 g, 5 eq.) was added to a solution of 2-[2-(tert-butoxycarbonylamino)ethoxy]ethyl 4-methylbenzenesulfonate (0.5 g, 1 eq.) in dry acetonitrile (10 mL) and the reaction mixture was heated to 75° C. for 3 h and then at 85° C. for 1 h. The acetonitrile was removed in vacuo. The crude residue was redissolved in DCM (25 mL) and washed with water (25 mL) the aqueous phase was re-extracted with DCM (2×25 mL). The combined organic phases were washed with water (50 mL), dried (MgSO$_4$), filtered and concentrated at reduced pressure to a pale yellow oil (0.4 g). The crude product was purified by silica column chromatography eluting with 10% methanolic ammonia in DCM to give 0.19 g (50%) of 18 as a colourless oil. $^{13}$C NMR (CDCl$_3$) δ 156.1, 72.5, 70.2, 70.1, 61.9, 49.2, 49.0, 40.5, 28.4. ESMS (C$_{13}$H$_{28}$N$_2$O$_5$) [M+H]$^+$ calc. 293.2076. found 293.2076.

Benzyl 11-(2-(2-hydroxyethoxyl)ethyl)-2,2-dimethyl-4-oxo-3,8-dioxa-5,11-diazatridecan-13-oate 19

DIPEA (0.23 mL, 2.0 eq.) was added to a solution of 18 (0.19 g, 1.0 eq.) in dry acetonitrile (1.5 mL) at 0° C. Benzyl-bromoacetate (0.11 mL, 1.0 eq.) was added in one portion and the reaction was allowed to warm to room temperature and stir for 18 hrs. A further portion of benzyl bromoacetate (55 μL) was added and the reaction was stirred for a further 2 h. The reaction was diluted with water (20 mL) and extracted into ethyl acetate (3×20 mL). The combined organic phases were washed with water (50 mL) and brine (50 mL) before being dried (MgSO$_4$), filtered and concentrated at reduced pressure to yield give a colourless oil (0.40 g). The crude product was purified by silica column chromatography eluting with 3% methanolic ammonia in DCM to give 0.23 g (79%) of 19 as a colourless oil. $^{13}$C NMR (CDCl$_3$) δ 171.3, 156.2, 135.7, 128.6, 128.4, 79.0, 72.3, 70.2, 69.4, 69.2, 66.2, 61.9, 55.2, 54.2, 40.5, 28.5. ESMS (C$_{22}$H$_{36}$N$_2$O$_7$) [M+H]$^+$ calc. 441.2601. found 441.2596.

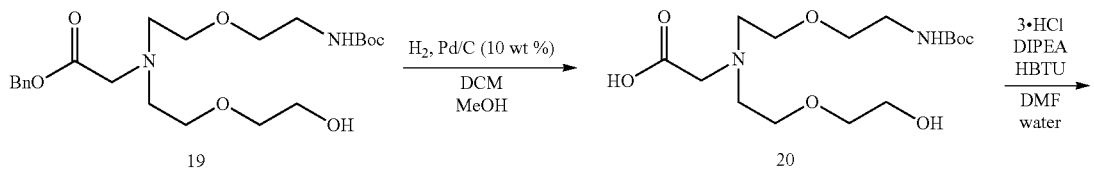

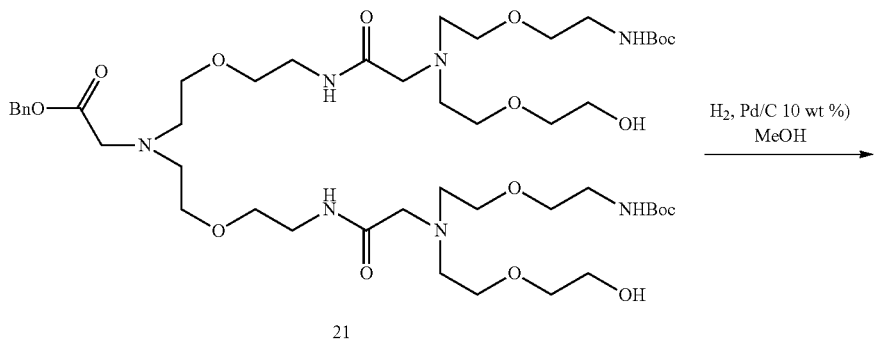

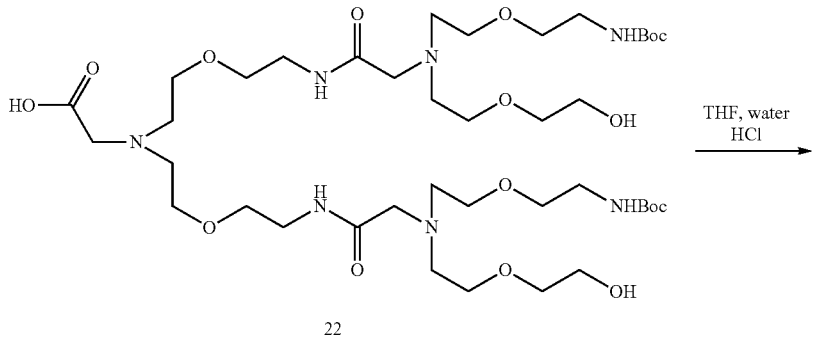

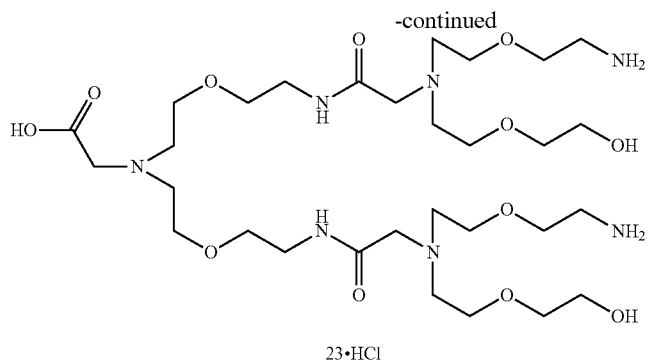
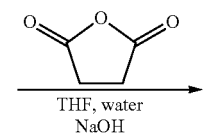

23·HCl

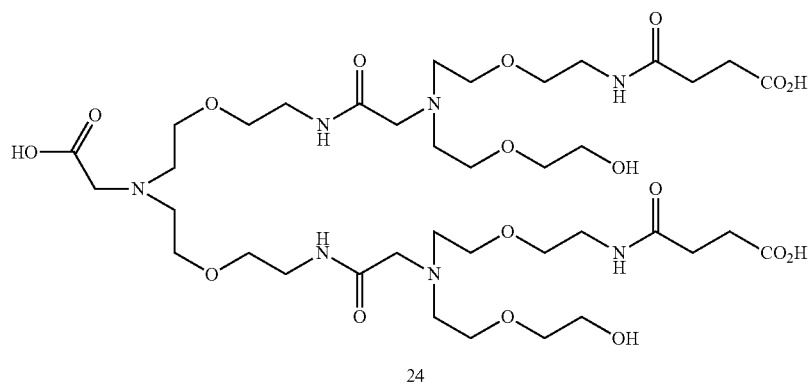 [SMILES: O=C(O)CCC(=O)NCCOCCN(CCOCCO)CC(=O)NCCOCCN(CCOCCNC(=O)CN(CCOCCO)CCOCCNC(=O)CCC(=O)O)CC(=O)O]

24

Use of an Example of Building Block C to Make Dendrimers Also Containing Building Block A 2-[2-[2-(tert-Butoxycarbonylamino)ethoxy]ethyl-[2-(2-hydroxyethoxyl)ethyl]amino]acetic acid, 20

To a solution of benzyl 2-[2-[2-(tert-butoxycarbonylamino)ethoxy]ethyl-[2-(2-hydroxyethoxyl)ethyl]amino]acetate (19) (1.25 g, 2.84 mmol) in DCM (4 mL) and methanol (6 mL) was added palladium (10%) on activated carbon (100 mg). The resulting mixture was placed under an atmosphere of hydrogen. The mixture was stirred at room temperature overnight and then filtered through Celite. The Celite was washed with methanol (2×20 mL) and the combined filtrates were concentrated at reduced pressure to give 1.20 g of 20. $^{13}$C NMR (CD$_3$OD, 125 MHz) δ 170.5, 156.2, 79.3, 72.8, 70.6, 66.8, 61.4, 55.2, 55.0, 40.3, 28.5. ESMS (C$_{15}$H$_{31}$N$_2$O$_7$) [M+H]$^+$ calc. 351.2131. found 351.2127.

Benzyl-2-aminoacetate(N,N):{6,9-diaza-3-oxa-7-oxononanyl(9,9)}$_{2x}$$^{G1}$:[N-(6-aza-9,9-dimethyl-3,8-dioxa-7-oxodecanyl)-N-(5-hydroxy-3-oxapentanyl)]$_2$-cascadane, 21

DIPEA (0.12 mL, 0.68 mmol, eq.) was added to a solution of benzyl 2-[bis[2-(2-aminoethoxyl)ethyl]amino]acetate dihydrochloride (3.HCl) (28 mg, 0.068 mmol, 1.0 eq.) in water (0.1 mL). A solution of 2-[2-[2-(tert-butoxycarbonylamino)ethoxy]ethyl-[2-(2-hydroxyethoxyl)ethyl]amino]acetic acid (20) (52 mg, 0.1484 mmol, 2.2 eq.) in DMF (0.5 mL) was added. HBTU (57 mg, 0.15 mmol, 2.2 eq.) was added in one portion and the reaction was stirred overnight at room temperature). The reaction was diluted with DCM (3 mL) and washed with water (2 mL). The aqueous phase was re-extracted with DCM (3 mL) and the combined organic phases were washed with brine (4 mL), dried (Na$_2$SO$_4$), filtered and concentrated at reduced pressure to give 100 mg of crude material. This material was purified by silica column chromatography eluting with 1% to 6% methanolic ammonia in DCM to give 33 mg (48%) of 21 as a colourless oil. $^{13}$C NMR (CDCl$_3$) δ 172.5, 171.6, 156.1, 135.7, 128.6, 128.4, 79.2, 72.5, 70.4, 70.1, 69.6, 69.1, 66.3, 61.5, 59.3, 55.9, 55.6, 55.5, 54.0, 40.5, 38.8, 28.5. ESMS (C$_{47}$H$_{86}$N$_7$O$_{16}$) [M+H]$^+$ calc. 1004.6131. found 1004.6138.

2-Aminoacetic acid(N,N):{6,9-diaza-3-oxa-7-oxononanyl(9,9)}$_{2x}$$^{G1}$:(N-(6-aza-9,9-dimethyl-3,8-dioxa-7-oxodecanyl)-N-(5-hydroxy-3-oxapentanyl))$_2$-cascadane, 22

To a solution of benzyl-2-aminoacetate(N,N):{6,9-diaza-3-oxa-7-oxononanyl(9,9)}$_{2x}$$^{G1}$:(N-(6-aza-9,9-dimethyl-3,8-dioxa-7-oxodecanyl)-N-(5-hydroxy-3-oxapentanyl))$_2$-cascadane (21) (32 mg, 0.032 mmol) in methanol (3 mL) was added palladium (10%) on activated carbon (8 mg). The resulting mixture was degassed by pumping under vacuum and then placed under an atmosphere of hydrogen. The mixture was stirred at room temperature for 18 h and then filtered through Celite. The Celite was washed with methanol and the combined filtrates were concentrated at reduced pressure to give 27 mg of 22 as a colourless oil. $^{13}$C NMR (CDCl$_3$) δ 172.6, 156.2, 79.2, 72.4, 70.4, 68.9, 68.7, 67.8, 67.1, 61.3, 59.2, 57.8, 55.4, 55.2, 54.8, 40.4, 38.7, 28.5. ESMS (C$_{40}$H$_{80}$N$_7$O$_{16}$) [M+H]$^+$ calc. 914.5662. found 915.5670.

2-Aminoacetic acid(N,N):{6,9-diaza-3-oxa-7-oxononanyl(9,9)}$_{2x}$$^{G1}$:(N-(5-amino-3-oxapentanyl)-N-(5-hydroxy-3-oxapentanyl))$_2$-cascadane hydrochloride, 23.HCl Aqueous hydrochloric acid (3 mol/L, 2 mL) was added to a stirred solution of 2-aminoacetic acid(N,N):{6,9-diaza-3-oxa-7-oxononanyl(9,9)}$_{2x}$$^{G1}$:(N-(6-aza-9,9-dimethyl-3,8-dioxa-7-oxodecanyl)-N-(5-hydroxy-3-oxapentanyl))$_2$-cascadane (22) (27 mg, 0.030 mmol, 1.0 eq.) in tetrahydrofuran (0.5 mL) at 40° C. for 2 h. The reaction mixture was concentrated at reduced pressure to give 30 mg of 23.HCl as a yellow oil. $^{13}$C NMR (CD$_3$OD) δ 168.8, 165.6, 72.0, 68.9, 66.7, 64.4, 64.2, 60.5, 55.1, 55.1, 55.0, 54.9, 54.7, 39.3, 39.2. ESMS (C$_{30}$H$_{64}$N$_7$O$_{12}$) [M+H]$^+$ calc. 714.4613. found 714.4614.

2-Aminoacetic acid(N,N):(6,9-diaza-3-oxa-7-ox-ononanyl(9,9))$^{G}_{2x}{}^{1}$:(N-(6-aza-3-oxa-7,10-dioxo-decan-10-olyl)-N-(5-hydroxy-3-oxapentanyl))$_2$-cascadane, 24

A solution of succinic anhydride (8.5 mg, 0.084 mmol, 2.2 eq.) in tetrahydrofuran (0.4 mL) was added to a solution of 2-aminoacetic acid(N,N):{6,9-diaza-3-oxa-7-oxononanyl(9,9)}$_{2x}{}^{G1}$:(N-(5-amino-3-oxapentanyl)-N-(5-hydroxy-3-oxapentanyl))$_2$-cascadane hydrochloride (23.HCl) (27 mg, 0.038 mmol, 1.0 eq.) in aq. sodium hydroxide (0.5 mol/L, 0.8 mL, 0.4 mmol, 10.5 eq.) at room temperature, then stirred overnight. The reaction mixture was concentrated at reduced pressure to give 30 mg of 24. $^{13}$C NMR (D$_2$O, 125 MHz) δ 177.2, 165.7, 72.0, 69.4, 68.9, 66.8, 64.5, 64.2, 60.5, 55.3, 55.2, 55.1, 55.0, 39.4, 39.2, 39.1, 28.9. ESMS (C$_{38}$H$_{71}$N$_7$O$_{18}$Na) [M+Na]$^+$ calc. 936.4753. found 936.4749.

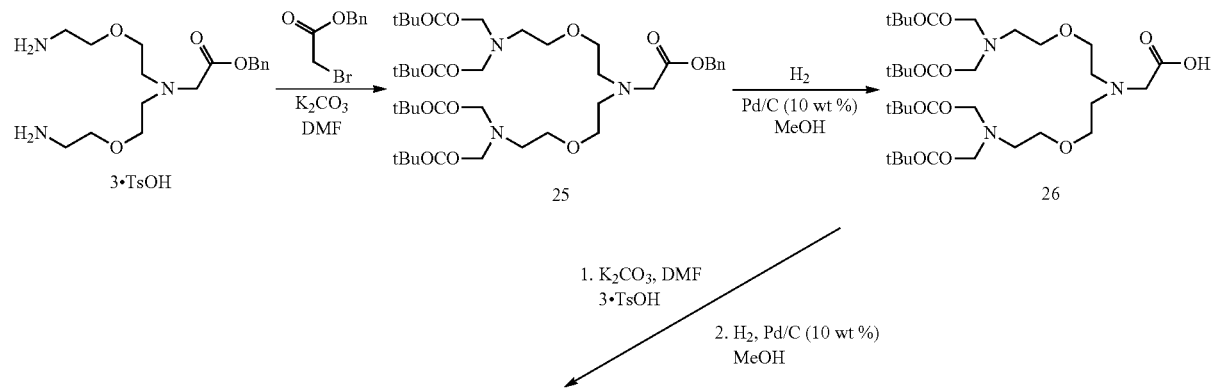

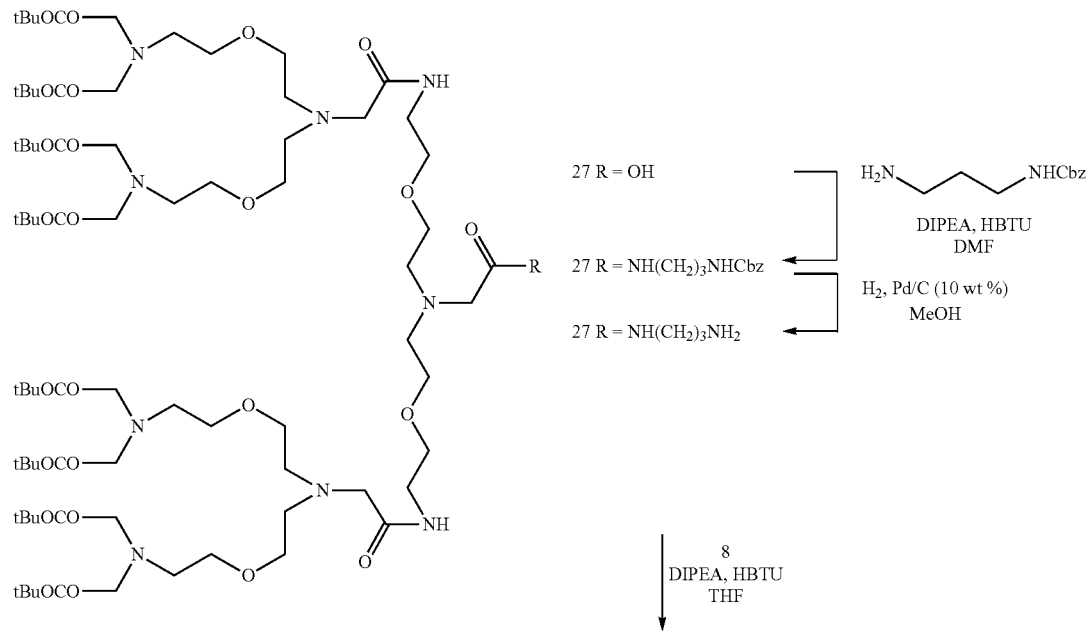

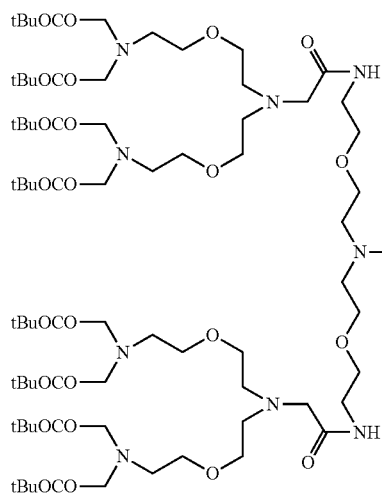
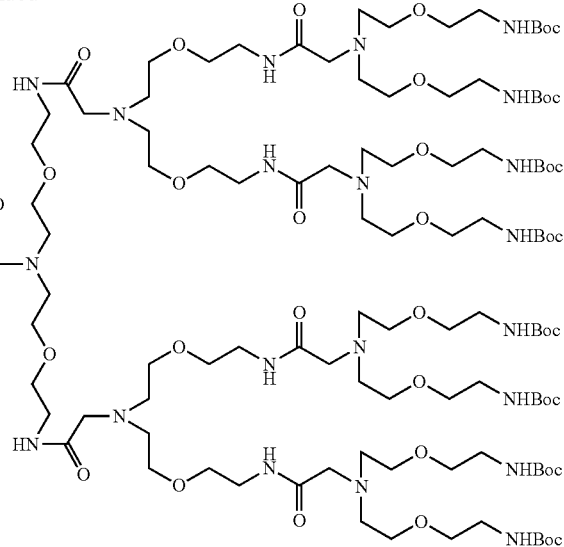

28

Synthesis and Use of an Example of Building Block B and the Synthesis of a 'Bow-Tie' Dendrimer

Benzyl-2-aminoacetate(N,N):{6-aza-3-oxahexanyl (6,6)}$_{2x}^{G1}$:(4,4-dimethyl-3-oxa-2-oxopentanyl)$_4$-cascadane, 25

Potassium carbonate (2.07 g, 15.0 mmol, 10.0 eq.) and then tert-butyl bromoacetate (1 mL, 6.82 mmol, 4.6 eq.) were added to a mixture of benzyl 2-[bis[2-(2-aminoethoxy)ethyl]amino]acetate trihydrochloride (3.TsOH) (0.67 g, 1.5 mmol, 1 eq.) in dry DMF (10 mL). The reaction mixture was allowed to stir at room temperature for 30 mins, before being heated at 70° C. for 90 min. The reaction mixture was cooled to 20° C. and diluted with water (50 mL) and extracted into toluene (2×100 mL). The combined organic phases were washed with water (100 mL) and brine (100 mL), before being dried (Na$_2$SO$_4$), filtered and concentrated at reduced pressure to give a yellow oil (0.9 g). The crude product was purified by silica column chromatography eluting with 2.5%-5% methanolic ammonia in DCM to give 0.56 g (47%) of 25 as a pale yellow oil. $^{13}$C NMR (CDCl$_3$) δ 171.6, 170.8, 136.0, 128.5, 128.3, 128.2, 80.8, 70.3, 70.0, 66.0, 56.7, 56.2, 54.2, 53.5, 28.2. ESMS (C$_{41}$H$_{70}$N$_3$O$_{12}$) [M+H]$^+$ calc. 818.4779. found 818.4781.

2-Aminoacetic acid(N,N):{6-aza-3-oxahexanyl (6,6)}$_{2x}^{G1}$:(4,4-dimethyl-3-oxa-2-oxopentanyl)$_4$-cascadane, 26

A solution of benzyl-2-aminoacetate(N,N):{6-aza-3-oxahexanyl(6,6)}$_{2x}^{G1}$:(4,4-dimethyl-3-oxa-2-oxopentanyl)$_4$-cascadane (25) (0.53 g, 0.67 mmol) in methanol (50 mL) was degassed by bubbling argon through the solution for 5 minutes prior to use. Palladium (10%) on activated carbon (25 mg) was added to the solution and the reaction mixture was placed under an atmosphere of hydrogen for 2.5 h. The reaction mixture was filtered through glass fibre filter paper. One portion of methanol (10 mL) was used to wash the residual palladium/carbon. The filtrate was concentrated at reduced pressure to give 0.44 g (94%) of 26. $^{13}$C NMR (CD$_3$OD) δ 172.3, 170.1, 82.4, 70.2, 65.8, 58.1, 57.3, 55.3, 54.8, 28.5. ESMS (C$_{34}$H$_{63}$N$_3$O$_{12}$Na) [M+Na]$^+$ calc. 728.4309. found 728.4304.

2-Aminoacetic acid(N,N):{6,9-diaza-3-oxa-7-oxononanyl(9,9)}$_{2x}^{G1}$:{6-aza-3-oxahexanyl(6,6)}$_{4x}^{G2}$:(4,4-dimethyl-3-oxa-2-oxopentanyl)$_8$-cascadane, 27 R=OH A heterogeneous mixture of 2-[bis[2-(2-aminoethoxy)ethyl]amino]acetic acid dihydrochloride (3.HCl) (85 mg, 0.264 mmol, 1 eq.) and DMF (1.5 mL) was stirred for 5 mins before the addition of DIPEA (0.46 mL, 2.6 mmol, 9.8 eq.). A solution of 2-aminoacetic acid(N,N):{6-aza-3-oxahexanyl(6,6)}$_{2x}^{G1}$:(4,4-dimethyl-3-oxa-2-oxopentanyl)$_4$-cascadane (26) (400 mg, 2.15 mmol, 8.1 eq.) in dry DMF (6 mL) was added to that mixture and the homogeneous solution was stirred for 5 mins before the addition of HBTU (0.22 g, 0.57 mmol, 2.2 eq.) in one portion. The reaction mixture was stirred at 20° C. for 2 h, then diluted with water (20 mL) and stirred for 5 minutes before being extracted into EA (3×20 mL). The combined organic phases were washed with water (2×50 ml) and brine (50 mL), then dried (Na$_2$SO$_4$), filtered and evaporated to a yellow oil (0.5 g). This crude product was purified by silica column chromatography eluting with 2.5% then 5% then 7.5% methanolic ammonia in DCM to give 0.35 g of a pale yellow oil. A solution of this intermediate, benzyl-2-aminoacetate(N,N):{6,9-diaza-3-oxa-7-oxononanyl(9,9)}$_{2x}^{G1}$:{6-aza-3-oxahexanyl(6,6)}$_{4x}^{G2}$:(4,4-dimethyl-3-oxa-2-oxopentanyl)$_8$-cascadane (0.220 g, 0.128 mmol) in methanol (20 mL) was degassed by bubbling argon through the solution for 5 minutes prior to use. Palladium (10%) on activated carbon (20 mg) was added to the solution and the reaction mixture was placed under an atmosphere of hydrogen for 5 h. The reaction mixture was filtered through glass fibre filter paper. Methanol (2×10 mL) was used to wash the residual palladium/carbon. The filtrate was concentrated at reduced pressure to give 0.168 g (38% yield for two steps) of 27 R=OH as a colourless oil. $^{13}$C NMR (CD$_3$OD) δ 171.7, 170.3, 166.7, 83.1, 70.7, 69.8, 69.5, 66.1, 65.9, 57.8, 57.4, 56.7, 56.5, 55.7, 55.4, 40.3, 30.4, 28.8, 28.5. ESMS (C$_{78}$H$_{146}$N$_9$O$_{26}$) [M+H]$^+$ calc. 1625.0379. found 1625.0371.

Benzyl (3-(2-aminoacetamido)propyl)carbamate(N, N):{6,9-diaza-3-oxa-7-oxononanyl(9,9)}$_{2x}^{G1}$:{6-aza-3-oxahexanyl(6,6)}$_{4x}^{G2}$:(4,4-dimethyl-3-oxa-2-oxopentanyl)$_8$-cascadane, 27 R═NH(CH$_2$)$_3$NHCbz DIPEA (26 µL, 0.148 mmol, 2.2 eq.) was added to a stirred solution of benzyl N-(3-aminopropyl)carbamate (14 mg, 0.067 mmol, 1 eq.) and 2-aminoacetic acid(N,N):{6,9-diaza-3-oxa-7-oxononanyl(9,9)}$_{2x}^{G1}$:{6-aza-3-oxahexanyl(6,6)}$_{4x}^{G2}$:(4,4-dimethyl-3-oxa-2-oxopentanyl)$_8$-cascadane (27 R═OH) (120 mg, 0.0738 mmol, 1.1 eq.) in dry DMF (2.6 mL). HBTU (28 mg, 0.074 mmol, 1.1 eq.) was added in one portion and the mixture was stirred at room temperature for 2 h. The reaction mixture was diluted with water (5 mL) and extracted into EA (3×5 ml). The combined organic phases were washed with water and brine (20 mL each), dried (Na$_2$SO$_4$), filtered and concentrated at reduced pressure to give a pale yellow oil (130 mg). This crude product was purified by silica column chromatography eluting with 1% then 3% then 5% methanolic ammonia in DCM to give 75 mg (61%) of 27 R═NH(CH$_2$)$_3$NHCbz as a pale yellow oil. $^{13}$C NMR (CD$_3$OD) δ 174.8, 174.2, 172.5, 158.8, 138.5, 129.6, 129.0, 128.9, 82.4, 70.6, 70.6, 70.5, 69.9, 67.4, 60.3, 59.5, 57.5, 56.3, 26.2, 55.2, 40.0, 39.3, 37.5, 31.0, 28.9, 28.6, 28.4. ESMS (C$_{89}$H$_{160}$N$_{11}$O$_{27}$) [M+H]$^+$ calc. 1815.1485. found 1815.1470.

2-amino-N-(3-aminopropyl)acetamide(N,N):{6,9-diaza-3-oxa-7-oxononanyl(9,9)}$_{2x}^{G1}$:{6-aza-3-oxahexanyl(6,6)}$_{4x}^{G2}$:(4,4-dimethyl-3-oxa-2-oxopentanyl)$_8$-cascadane, 27 R═NH(CH$_2$)$_3$NH$_2$ A solution of benzyl (3-(2-aminoacetamido)propyl)carbamate(N,N):{6,9-diaza-3-oxa-7-oxononanyl(9,9)}$_{2x}^{G1}$:{6-aza-3-oxahexanyl(6,6)}$_{4x}^{G2}$:(4,4-dimethyl-3-oxa-2-oxopentanyl)$_8$-cascadane (27 R═NH(CH$_2$)$_3$NHCbz) (72 mg, 0.040 mmol) in methanol (5 mL) was degassed by bubbling argon through the solution for 5 minutes prior to use. Palladium (10%) on activated carbon (7 mg) was added to the solution and the reaction mixture was placed under an atmosphere of hydrogen for 4 h. The reaction mixture was filtered through glass fibre filter paper. Methanol (3×5 mL) was used to wash the residual palladium/carbon. The filtrate was concentrated at reduced pressure to give 33 mg (49%) of 27 R═NH(CH$_2$)$_3$NH$_2$ as a colourless oil. $^{13}$C NMR (CD$_3$OD) δ 175.3, 175.4, 172.5, 82.5, 70.6, 70.6, 70.5, 70.0, 69.9, 60.2, 59.7, 57.5, 56.2, 56.0, 40.0, 38.9, 37.1, 30.4, 28.6. ESMS (C$_{81}$H$_{154}$N$_{11}$O$_{25}$) [M+H]$^+$ calc. 1681.1117. found 1681.1108.

1-(Amino(N,N):{7-oxo-3-oxa-6,9-diazanonanyl(9,9)}$_{2x}^{G1}$:{3-oxa-6-azahexyl(6,6)}$_{4x}^{G2}$:(4,4-dimethyl-2-oxo-3-oxapentyl)$_8$-cascadyl)-2,8-dioxo-3,7,10-triazadecane(10,10):{7-oxo-3-oxa-6,9-diazanonanyl(9,9)}$_{2x,4x}^{G1,G2}$:(5-aza-8,8-dimethyl-6-oxo-3,7-dioxanonanyl)$_8$-cascadane, 28

DIPEA (7 µL, 0.040 mmol, 3.2 eq.) was added to a stirred solution of 2-amino-N-(3-aminopropyl)acetamide(N,N):{6,9-diaza-3-oxa-7-oxononanyl(9,9)}$_{2x}^{G1}$:{6-aza-3-oxahexanyl(6,6)}$_{4x}^{G2}$:(4,4-dimethyl-3-oxa-2-oxopentanyl)$_8$-cascadane (27 R═NH(CH$_2$)$_3$NH$_2$) (21 mg, 0.013 mmol, 1.0 eq.) and 2-aminoacetic acid(N,N):{6,9-diaza-3-oxa-7-oxononanyl(9,9)}$_{2x,4x}^{G1,G2}$:(6-aza-9,9-dimethyl-3,8-dioxa-7-oxodecanyl)$_8$-cascadane (8) (30 mg, 0.012 mmol, 1 eq.) in dry THF (3 mL) at 20° C. HBTU (5 mg, 0.0129205 mmol, eq.) was added in one portion and the mixture was stirred for 5 h. The reaction mixture was concentrated at reduced pressure (30° C.) to give a colourless oil (65 mg). This crude product was purified by silica column chromatography eluting with 1% to 10% methanolic ammonia in DCM. The resulting purified material was dissolved in EA (5 mL) and washed with brine. The brine layer was re-extracted with EA (5 mL). The combined organic phases were dried (Na$_2$SO$_4$), filtered and concentrated at reduced pressure to give 28 mg (55%) of 28 as a colourless oil. 13C NMR (CD$_3$OD) δ 174.3, 172.6, 158.4, 82.5, 80.1, 71.1, 70.7, 70.6, 70.4, 70.3, 69.6, 60.2, 59.3, 57.6, 56.2, 56.1, 55.3, 41.4, 40.1, 40.0, 37.5, 31.0, 28.9, 28.6. ESMS (C$_{191}$H$_{368}$N$_{32}$O$_{62}$) [M+4H]$^{4+}$ calc. 1025.6656. found 1025.6646.

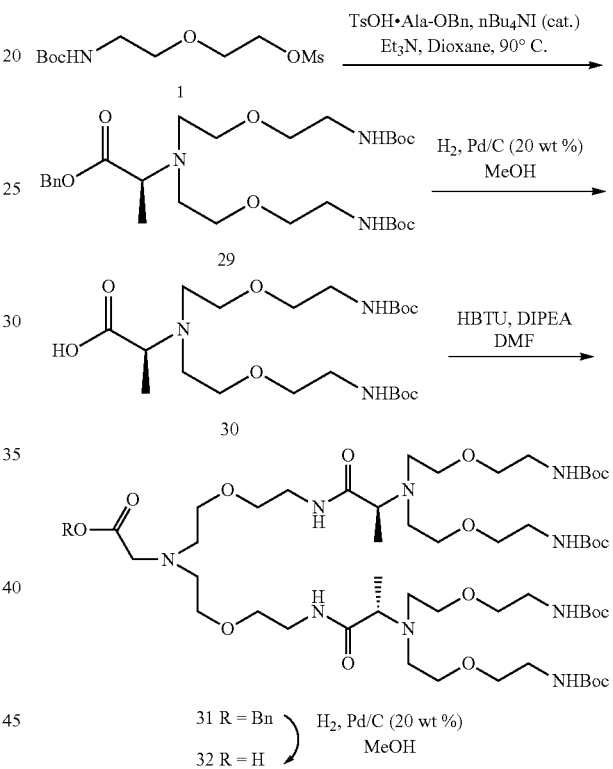

Example of a Dendrimer Containing an Amino Acid Component Other than Glycine

Benzyl 2-[bis[2-[2-(tert-butoxycarbonylamino)ethoxy]ethyl]amino]-2S-methylacetate, 29

Benzyl alaninate p-toluenesulfonate (0.5 g, 1.42 mmol) was dried under hi-vacuum then placed under an atmosphere of argon. A solution of 2-[2-(tert-butoxycarbonylamino)ethoxy]ethyl methanesulfonate (1) (1.01 g, 3.56 mmol) in dry 1,4-dioxane (5 mL) was added. n-Tetrabutylammonium iodide (0.13 g, 0.36 mmol) and triethylamine (0.99 mL, 7.1 mmol) were added and the reaction heated to 90° C. for 24 hours. The reaction mixture was cooled to room temperature and diluted with water (50 mL) and extracted into ethyl acetate (2×50 mL). The combined organic extracts were washed with water (50 mL) and brine (50 mL), then dried (MgSO4), filtered and concentrated. The crude mixture was purified on silica gel eluting with a gradient of 20% to 75% ethyl acetate in petroleum ether. 29 was isolated as a pale yellow oil (88 mg, 11% yield). $^{13}$C NMR (CDCl$_3$) δ 173.9, 156.0, 136.0, 128.6, 128.2, 79.1, 70.6, 69.9, 66.1, 60.0, 51.7, 40.4, 28.4, 16.1. ESMS (C$_{28}$H$_{47}$N$_3$O$_8$) [M+Na]$^+$ calc. 576.3261. found 576.3253.

2-[Bis[2-[2-(tert-butoxycarbonylamino)ethoxy]ethyl]amino]-2S-methylacetic acid, 30

A solution of 29 (94 mg, 0.17 mmol) in methanol (5 mL) was degassed by bubbling argon through the solution for two minutes. Palladium (10%) on activated carbon (20 mg) was added to the solution and the reaction mixture was placed under an atmosphere of hydrogen. The reaction was stirred at room temperature for 15 hours before being filtered through a pad of Celite. The Celite was washed with methanol (2×10 mL) and the combined filtrates were concentrated to provide a colourless oil (0.079 g, quant.) The product (30) was used without any further purification. $^{13}$C NMR (CD$_3$OD) δ 172.2, 158.5, 80.2, 71.5, 65.9, 63.6, 52.9, 41.1, 28.8, 11.9. ESMS (C$_{21}$H$_{41}$N$_3$O$_8$) [M+Na]$^+$ calc. 486.2791. found 486.2778.

Benzyl-2-aminoacetate(N,N):{6,9-diaza-8S-methyl-3-oxa-7-oxononanyl(9,9)}$_{2x}^{G1}$:(6-aza-9,9-dimethyl-3,8-dioxa-7-oxodecanyl)$_4$-cascadane, 31

N,N-Diisopropylethylamine (0.130 mL, 0.76 mmol) was added to a mixture of Benzyl 2-(bis(2-(2-aminoethoxyl)ethyl)amino)acetate, tri(p-toluenesulfonate) (3.TsOH) (65 mg, 0.076 mmol) in dry DMF (2 mL). A solution of carboxylic acid 30 (79 mg, 0.167 mmol) in dry DMF (2 mL) was added and the resulting mixture was stirred at 20° C. N,N,N',N'-Tetramethyl-O-(1H-benzotriazol-1-yl)uroniumhexafluorophosphate (67 mg, 0.168 mmol) was added in one solid portion and stirring was continued for 16 hours overnight. The reaction was diluted with water (20 mL) and extracted into ethyl acetate (2×30 mL). The combined organic phases were washed with saturated aqueous sodium hydrogencarbonate (1×50 mL), water (1×50 mL) and brine (2×50 mL) before being dried (MgSO$_4$), filtered and concentrated. The crude mixture was purified on silica gel eluting with a gradient of 0% to 5% methanol in chloroform to provide 31 as a pale yellow oil (53 mg, 57%). $^{13}$C NMR (CD$_3$OD) δ 176.9, 173.0, 158.35, 137.6, 129.7, 129.5, 129.4, 80.1, 71.0, 70.9, 70.8, 70.7, 27.2, 62.0, 57.1, 55.4, 51.9, 41.4, 40.1, 28.9, 11.1. ESMS (C$_{59}$H$_{107}$N$_9$O$_{18}$) [M+Na]$^+$ calc. 1252.7634. found 1252.7634.

2-Aminoacetic acid(N,N):{6,9-diaza-8S-methyl-3-oxa-7-oxononanyl(9,9)}$_{2x}^{G1}$:(6-aza-9,9-dimethyl-3,8-dioxa-7-oxodecanyl)$_4$-cascadane, 32

A solution of 31 (0.052 g, 0.042 mmol) in methanol (3 mL) was degassed by bubbling argon through the solution for two minutes. Palladium (10%) on activated carbon (20 mg) was added to the solution and the reaction mixture was placed under an atmosphere of hydrogen. The reaction was stirred at room temperature for 16 hours before being filtered through a pad of Celite. The Celite was washed with methanol (2×10 mL) and the combined filtrates were concentrated to provide 32 as a colourless oil (0.048 g, quant.). $^{13}$C NMR (CD$_3$OD) δ 170.8, 158.5, 80.2, 71.8, 71.6, 71.2, 71.0, 70.8, 66.9, 65.5, 58.2, 57.4, 52.4, 41.2, 40.3, 28.9, 12.6. ESMS (C$_{52}$H$_{101}$N$_9$O$_{18}$) [M+Na]$^+$ calc. 1162.7162. found 1162.7152.

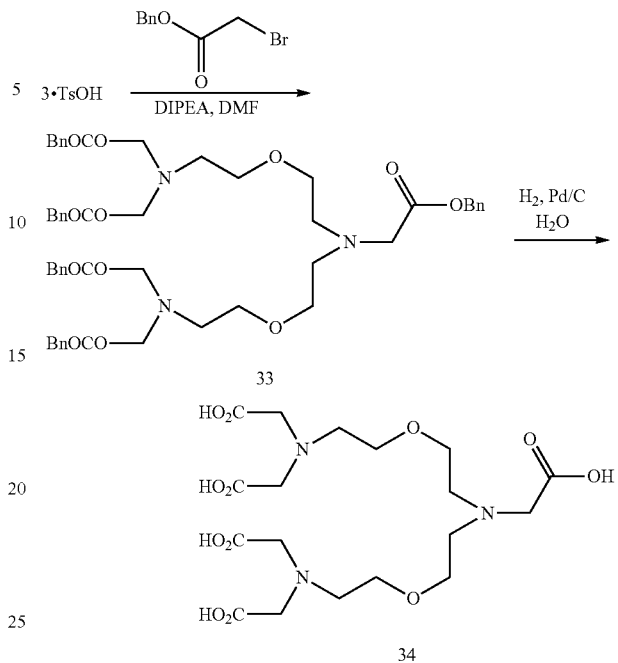

Another Example of Building Block B

2-Aminoacetic acid(N,N):{6-aza-3-oxahexanyl(6,6)}$_{2x}^{G1}$:(carboxymethyl)$_4$-cascadane, 34

DIPEA (0.41 mL, 2.3 mmol) was added to a stirred solution of 3.TsOH (100 mg, 0.12 mmol) in DMF (8.5 mL). Benzyl bromoacetate (0.15 mL, 0.91 mmol) was added immediately afterwards and the solution was left stirring at 20° C. overnight. The reaction was diluted with water (40 mL) and extracted into ethyl acetate (2×40 mL). The combined organic phases were washed with water (2×30 mL) and then brine (30 mL), dried (Na$_2$SO$_4$), filtered and concentrated to a yellow oil (0.3 g). The residue was purified by flash column chromatography on silica gel using a gradient elution (1 to 8% methanol ammonia in DCM) to provide the product 33 as a colourless oil (70 mg, 64%). $^{13}$C NMR (CDCl$_3$) δ 171.6, 171.2, 136.0, 135.8, 128.6, 128.5, 128.3, 128.2, 70.2, 70.0, 66.2, 66.0, 56.1, 55.9, 54.2, 53.7. ESMS (C$_{53}$H$_{61}$N$_3$O$_{12}$) [M+H]$^+$ calc. 932.4334. found 932.4336.

Palladium on activated carbon (10%, 9 mg) was added to a stirred solution of 33 (67 mg, 0.072 mmol) in methanol (5 mL). The mixture was stirred under an atmosphere of hydrogen for 3 hours at room temperature before being filtered through a glass fibre filter and washed with methanol (2×3 mL). The reaction mixture was concentrated to a white solid (20 mg) and was shown to be incomplete. The white residue was re-dissolved in a methanol and water mixture (1:1, 5 mL) and further palladium on activated charcoal (10%, 5 mg) was added before the mixture was stirred for a further 18 h under a hydrogen atmosphere. The reaction mixture was again filtered through a glass fibre filter and washed with methanol (2×3 mL). The reaction mixture was concentrated to give 34 as a white solid (12 mg, 35%). $^{13}$C NMR (D$_2$O) δ 169.7, 65.0, 64.8, 57.1, 56.0, 55.5, 55.2. ESMS ($C_{18}H_{31}N_3O_{12}$) $[M+Na]^+$ calc. 504.1805. found 504.1808.

Benzyl 2-[4-[2-(bis(2-(tert-butoxy)-2-oxoethyl)amino)ethoxy]ethyl-[2-(2-hydroxyethoxy)ethyl]amino]acetate, 35

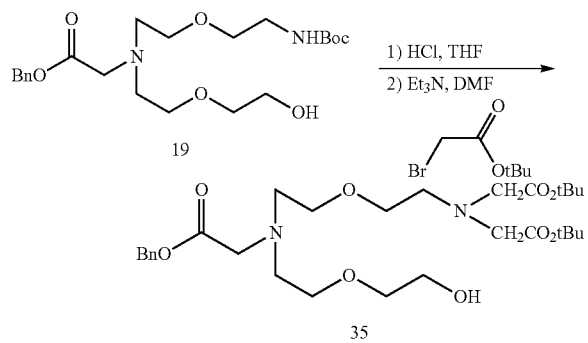

Another Example of Building Block D

Aqueous hydrochloric acid (3 M, 0.25 mL) was added to a stirred solution of benzyl 2-[2-[2-(tert-butoxycarbonylamino)ethoxy]ethyl-[2-(2-hydroxyethoxy)ethyl]amino]acetate, 19 (60 mg, 0.14 mmol) in tetrahydrofuran (1 mL). The solution was stirred at 30° C. for 1 h before being concentrated to a colourless oil. The residue was re-dissolved in N,N-dimethylformamide (2 mL, 26 mmol) and triethylamine (0.25 mL, 1.8 mmol) was added and the pH was approximately 8. Tert-butyl bromoacetate (45 µL, 0.3007 mmol) was added and the reaction mixture was stirred for 18 h. Water (20 mL) was added and the reaction mixture was extracted using ethyl acetate (2×20 mL). The combined organic phases were washed with water (2×50 mL), dried ($Na_2SO_4$), filtered and the filtrate was concentrated to a colourless oil (64 mg). Flash column chromatography on silica gel using gradient elution (2-8% methanol ammonia in dichloromethane) was used to purify the product (46 mg, 59%); $^{13}$C NMR ($CDCl_3$, 125 MHz) δ 171.6, 170.8, 135.8, 128.6, 80.9, 72.4, 70.3, 69.7, 66.1, 61.8, 56.6, 55.8, 54.3, 54.2, 53.5, 28.2. ESMS ($C_{29}H_{49}N_2O_9$) $[M+H]^+$ calc. 569.3433. found 569.3438.

MRI Contrast Agent

The following provides an example of the attachment of an imaging agent to a dendrimer of the present invention.

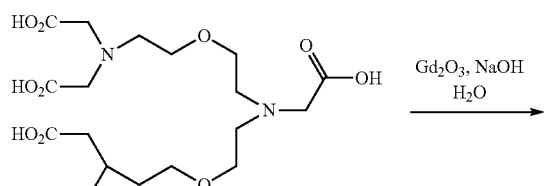

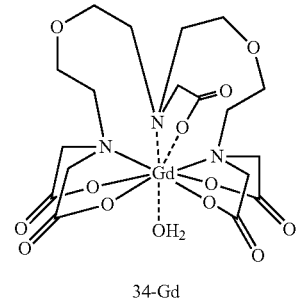

34-Gd

Gadolinium complex of 2-aminoacetic acid(N,N):{6-aza-3-oxahexanyl(6,6)}$_{2x}^{G1}$: (carboxymethyl)$_4$-cascadane, 34-Gd Gadolium oxide (3 mg, 0.008 mmol) was added to a stirred solution of 2-aminoacetic acid(N,N):{6-aza-3-oxahexanyl(6,6)}$_{2x}^{G1}$:(carboxymethyl)$_4$-cascadane 34 (9 mg, 0.019 mmol) in water (0.5 mL). The pH of the solution was adjusted to pH 8 using aqueous sodium hydroxide (1 M, 0.05 mL). The reaction mixture was heated at 80° C. for 18 h before being cooled and filtered. The filtrate was concentrated to give 34-Gd as a white solid (12 mg, quantitive yield). ESMS ($C_{18}H_{26}^{155}GdN_3Na_3O_{12}$) $[M+Na]^+$ calc. 700.0431. found 700.0436.

34-Gd is water soluble. This has the advantage over Gd-DPTA disodium salt which is sparingly water soluble. Therefore, an alternative cation is required. Gd-DPTA is the active ingredient in Magnevist, a commercial MRI contrast agent. In Magnevist, meglumine is used to make Gd-DPTA water soluble.

Water relaxivity measurements provide an indication of whether a material will increase contrast in MRI imaging techniques. Water relaxivity measurements were performed in aqueous solutions. $T_1$ measurements were made on a 500 MHz (11.75 T) Bruker NMR using a standard inversion recovery sequence (180-t-90) at 30° C. The relaxivity of water in $D_2O$ in the presence of (meglumine)$_2$[Gd(III)(DPTA)(OH$_2$)] (prepared using a literature procedure (Uggeri 1995)) and 34-Gd was found to be 3.84 and 1.20 mM$^{-1}$ s$^{-1}$, respectively. From these results it can be seen that 34-Gd is an effective paramagnetic relaxation enhancement agent and so should lead to increased contrast in MRI imaging techniques, but is less effective than the DPTA complex.

The use of higher generation dendrimers should result in higher relaxivities and may also lead to slower clearance of the resulting MRI contrast agent in vivo and hence result in contrast agents with longer resident lifetimes (Lim 2012).

Glycosylated Dendrimer

The following provides an example of the attachment of an inactive agent to a dendrimer of the present invention suitable for targeting.

125    126

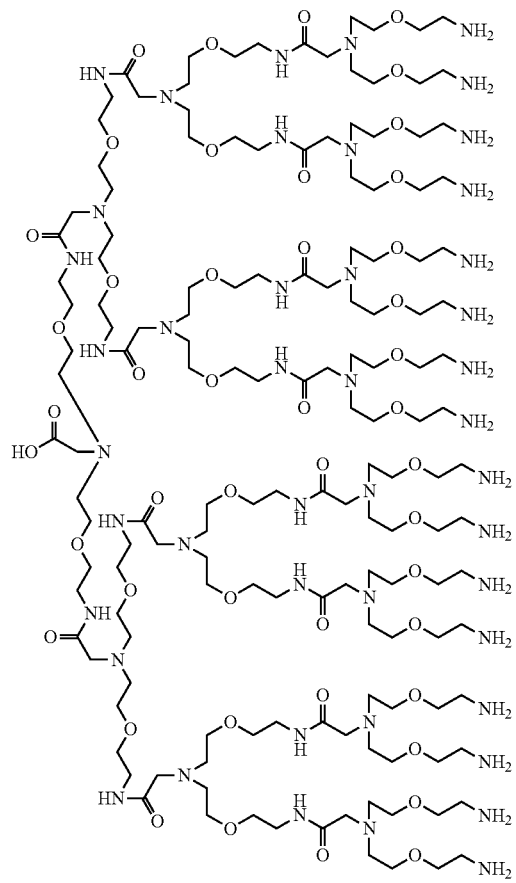

12

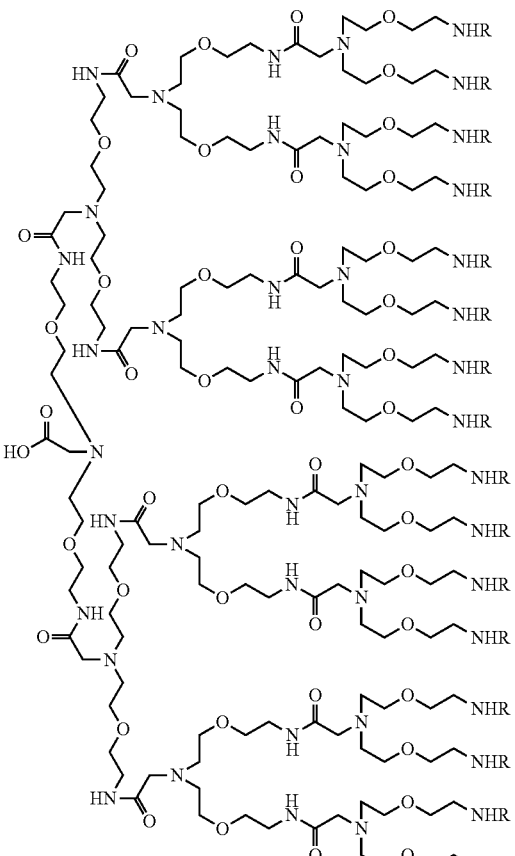

37

1) 36 (R—NHS), DIPEA, DMF, H₂O
2) NaOMe, MeOH H₂O

R =

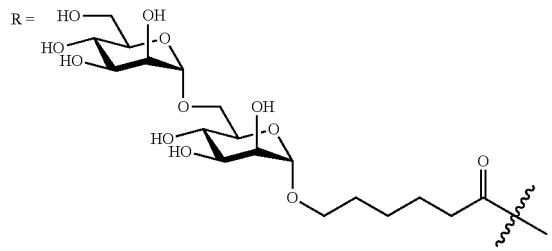

To amine terminated dendrimer 12 (33 mg, 7.1 μmol, 1.0 eq.) was added DMF (1.0 mL), DIPEA (200 μL, 1.14 mmol, 159 eq.) and water (0.1 mL) to aid in solubility. Active ester 36 (155 mg, 0.183 mmol, 25.6 eq.) was added and the resulting solution left for 2 days and then concentrated in vacuo.

The resulting residue was dissolved in methanol (5 mL) and then 5.4 M sodium methoxide in methanol was added until the pH=12. As acetate deprotection progressed, a precipitate started to form and so water (2.5 mL) was added to keep the reaction in solution. After 3 hours, the reaction was neutralised with solid CO₂ dry ice and then concentrated in vacuo. ¹H NMR at this point showed no acetates to be present.

Water (2.5 mL) was added to the crude product and the resulting mixture filtered through 1 μm filter and loaded into a washed Macrosep 3K Omega Centrifugal Device (Pall) followed by water (2.5 mL) washings. The solution was concentrated to approximately 2.5 mL (4500 rpm, 15° C.) and then dialysed with water (2.5 mL, 4500 rpm, 15° C.), aqueous sodium bicarbonate (28 mg/mL, 2.5 mL, 4500 rpm, 15° C., three times) and water (3 mL, 4500 rpm, 15° C., seven times). The pH was then adjusted from 10 to 5 using dilute hydrochloric acid and then the solution dialysed with water (3 mL, 4500 rpm, 15° C., twice), filtered through a 0.2 km cellulose acetate filter and lyophilised to give the product 37 (80 mg of a white powder, quantitative yield). $^{13}$C NMR (D$_2$O) δ 176.9, 165.6, 99.9, 99.5, 72.8, 71.0, 70.7, 70.2, 70.1, 69.2, 68.8, 67.8, 67.0, 66.8, 66.7, 65.8, 64.0, 61.0, 38.9, 35.8, 28.3, 25.2, 25.2. ESMS deconvoluted ($C_{438}H_{797}N_{45}O_{238}$.3HCl) calc. 10,610.1. found 10,609.5.

The specific targeting of mannose-capped dendrimers to mannose receptors, highly expressed in cells of the immune system, has the potential to provide drug/antigen delivery systems for vaccination or treatment of diseases localized in macrophages and other antigen-presenting cells (Irache 2008).

Stability

The stability of the dendrimers presented in this invention has been demonstrated by subjecting compound 13 to forcing degradation conditions with HPLC monitoring. Results were as follows:

No observable degradation after 24 h neat at 40° C.
12% degradation after 24 h in 1 M HCl at 20° C.
30% degradation after 24 h in 1 M NaOH at 20° C.
63% degradation after 24 h in 1% $H_2O_2$ at 20° C.
41% degradation after 24 h neat at 80° C.

Assessment of Potential Cytotoxicity

The potential cytotoxic properties of compounds 12, 13 and 14 were evaluated by measuring percentage cell viability of sheep spleen cells versus a PBS control after 24 h and 48 h exposure to 0.01, 0.1 and 1 mg/mL solutions of each compound in PBS at 36.5° C. Results were as follows:

|  | Cell viability | | | | | |
| --- | --- | --- | --- | --- | --- | --- |
|  | 12 | | 13 | | 14 | |
| Concentration | 24 h | 48 h | 24 h | 48 h | 24 h | 48 h |
| 0.01 mg/mL | 94% | 84% | 107% | 97% | 104% | 99% |
| 0.1 mg/mL | 92% | 85% | 104% | 98% | 104% | 97% |
| 1 mg/mL | 99% | 87% | 106% | 100% | 97% | 90% |

Reference to any prior art in this specification is not, and should not be taken as, an acknowledgment or any form of suggestion that the prior art forms part of the common general knowledge in New Zealand.

Throughout this specification, unless the context requires otherwise, the words "comprise", "comprising" and the like, are to be construed in an inclusive sense as opposed to an exclusive sense, that is to say, in the sense of "including, but not limited to".

The foregoing describes the invention including preferred forms thereof. Modifications and alterations that would be readily apparent to the skilled person are intended to be included within the spirit and scope of the invention described.

REFERENCES

Balieu, S; Cadiou, C; Martinez A; Nuzillard J-M; Oudart J-B; Maquart F-X; Chuburu F; Bouquillon S.; (2012); "Encapsulation of contrast imaging agents by polypropylene-imine-based dendrimers"; *J. Biomed. Mater. Res. Part A;* 00A:000-000.

Bhadra, D.; Yadav, A. K.; Bhadra, S. and Jain, N. K.; (2005); "Glycodendrimericnanoparticulate carriers of primaquinephosphate for liver targeting"; *Int. J. Pharm.;* 295; 221-233.

Boisselier, E.; Liang, L.; Dalko-Csiba, M.; Ruiz, J.; Astruc, D.; (2010); "Interactions and Encapsulation of Vitamins C, B 3, and B 6 with Dendrimers in Water"; *Chem. Eur. J.;* 16; 6056-6068.

British Pharmacopeia 2013; British Pharmacopoeia Commission Secretariat of the Medicines and Healthcare products Regulatory Agency.

European Pharmacopeia 2013; European Directorate for the Quality of Medicines & HealthCare.

Friedhofen J. H. and Vogtle F. (2006) "Detailed nomenclature for dendritic molecules" *New J. Chem.* 30, 32-43.

Green T. W. and Wuts P. G. M. (1999) Protective groups in organic synthesis. 3$^{rd}$ edition. John Wiley & Sons, Inc. New York.

Hafiz, A. A., Negm, N. A. and El Awady, M. Y. (2005) "Influence of structure on the cationic polytriethanol-ammonium bromide derivatives. III. Biological activity" *Egyptian Journal of Chemistry* 48(2), 245-250.

Irache J. M., Salman H. H., Gamazo C. and Espuelas S. (2008) " " *Expert Opin. Drug Deliv.* 5, 703-724.

Jain K., Kesharwani P., Gupta U. and Jain N. K. (2010) "Dendrimer toxicity: Let's meet the challenge" *Int. J. Pharm.* 394, 122-142.

Kim Y-S., Kim K. M., Song R., Jun M. J. and Sohn Y. S. (2001) "Synthesis, characterization and antitumor activity of quinolone-platinum(II) conjugates" *J. Inord. Biochem.* 87 (3), 157-163.

Kojima, C.; Kono, K.; Maruyama, K. and Takagishi, T.; (2000); "Synthesis of Polyamidoamine Dendrimers Having Poly(ethyleneglycol) Grafts and Their Ability To Encapsulate Anticancer Drugs"; *Bioconivaate Chem.;* 11; 910-917.

Lim, J.; Turkbey, B.; Bernardo, M.; Bryant, L. H. Jr.; Garzoni, M.; Pavan, G. M.; Nakajima, T.; Choyke, P. L.; Simanek, E. E. and Kobayashi, H. (2012) "Gadolinium MRI Contrast Agents Based on Triazine Dendrimers: Relaxivity and In Vivo Pharmacokinetics"; *Bioconjugate Chem.;* 23; 2291-2299.

McCarthy, T. D., Karellas, P., Henderson, S. A., Giannis, M., O'Keefe, D. F., Heery, G., Paull, J. R. A., Matthews, B. R. and Holan, G. (2005) "Dendrimers as Drugs: Discovery and Preclinical and Clinical Development of Dendrimer-Based Microbicides for HIV and STI Prevention" *Mol. Pharm.* 2 (4), 312-318

Menjoge A. R., Kannan R. M. and Tomalia, D. A. (2010) "Dendrimer-based drug and imaging conjugates: design considerations for nanomedical applications." *Drug Discovery Today* 15 (5/6), 171-185.

Montalbetti, C. A. G. N. and Falque, V.; (2005); "Amide bond formation and peptide coupling"; Tetrahedron; 61; 10827-10852.

Morgan, M. T.; Nakanishi, Y; Kroll, D. J.; Griset, A. P.; Carnahan, M. A.; Wathier, M.; Oberlies, N. H; Manikumar, G.; Wani, M. C. and Grinstaff, M. W.; (2006); "Dendrimer-Encapsulated Camptothecins: Increased Solubility, Cellular Uptake, and Cellular Retention Affords Enhanced Anticancer Activity In vitro"; *Cancer Res.;* 66, 11913-11921.

Mucalo, M. R. and Rathbone, M. J.; (2012); "Melt-extruded polyethylene oxide (PEO) rods as drug delivery vehicles: Formulation, performance as controlled release devices and the influence of co-extruded excipients on drug release profiles"; *Chemistry in New Zealand;* 76; 85-95.

Mullen, D. G., Desai, A., van Dongen, M. A., Barash, M., Baker J. R. Jr. and Banaszak Holl M. M. (2012) "Best Practices for Purification and Characterization of PAMAM Dendrimer" *Macromolecules* 45, 5316-5320.

Negm, N. A., Hafiz, A. A. and El Awady, M. Y. (2004) "Influence of structure on the cationic polytriethanolammonium bromide derivatives. I. Synthesis, surface and thermodynamic properties" *Egyptian Journal of Chemistry,* 47(4), 369-381.

Negm, N. A., Hafiz, A. A. and El Awady, M. Y. (2005) "Influence of structure of the cationic poly-triethanolammonium bromide derivatives. II. corrosion inhibition" *Egyptian Journal of Chemistry,* 48(2), 201-210.

Pifferi, G.; Restani, P.; (2003); "The safety of pharmaceutical excipients"; *Il Farmaco;* 58; 541-550.

Röglin, L., Lempens, E. H. M. and Meijer, E. W. (2011) "A Synthetic "Tour de Force": Well-Defined Multivalent and Multimodal Dendritic Structures for Biomedical Applications." *Angew. Chem. Int. Ed.* 50, 102-112.

Risch, S. J.; (1995);"Encapsulation: Overview of Uses and Techniques"; Encapsulation and Controlled Release of Food Ingredients; Chapter 1; p 2-7; ACS Symposium Series; American Chemical Society: Washington, D.C.

Rowe, R. C.; Sheskey, P. J.; Cook, W. G.; Fenton, M. E.; (2012); "Handbook of Pharmaceutical Excipients"; 7th edition; Pharmaceutical Press.

Stahl, H. P. and Wermuth, C. G. (2002) Handbook of Pharmaceutical Salts: Properties, Selection, and Use. Wiley-VCH, Zurich.

Tomalia, D. A. and Fre'chet, J. M. J. (2002) "Discovery of dendrimers and dendritic polymers: a brief historical perspective." J. Polym. Sci. Part A: Polym. Chem., 40, 2719-2728.

Uggeri, F.; Silvio, A.; Anelli, P. L.; Botta, M.; Brocchetta, M.; de Haën, C.; Ermondi, G.; Grandi, M. and Paoli, P. (1995) "Novel contrast agents for magnetic resonance imaging. Synthesis and characterization of the ligand BOPTA and its Ln(III) complexes (Ln=Gd, La, Lu). X-ray structure of disodium (TPS-9-145337286-C-S)-[4-caboxymethyl)-1-phenyl-2-oxa-5,8,11-triazatridecan-13-oato(5-)]gadolinite(2-) in a mixture with its enantiomer." Inorg. Chem. 34, 633-642.

United States Pharmacopeia 2013; United States Pharmacopeial Convention (USP).

Zanini D. and Roy R. (1996) "Novel Dendritic α-Sialosides: Synthesis of Glycodendrimers Based on a 3,3'-Iminobis (propylamine) Core." J. Org. Chem., 61, 7348-7354

US 2009/0036353 A1 Insulin Derivatives Conjugated with Structurally Well Defined Branched Polymers.

What we claim is:

1. A compound of formula (I):

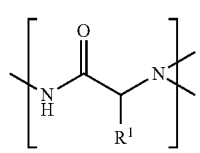

or salts thereof, wherein:
$Y^1, Y^2, Y^3, Y^4$ or $Y^5$ are

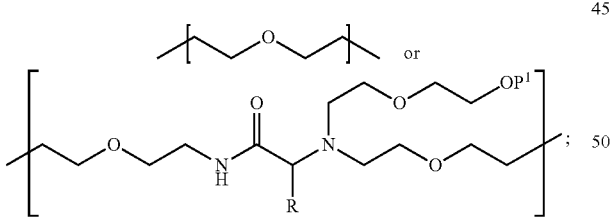

$m=n=p=q=2$; or $m=0$ and $n=p=q=2$; or $m=n=0$ and $p=q=2$; or $m=n=p=0$ and $q=2$; or $m=n=p=q=0$,
wherein:
when $q=2$, $C^1$ is

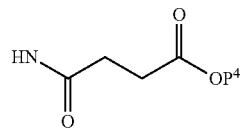

when $q=0$, $C^1$ is $NHP^2$ or $N(CH_2CO_2P^4)_2$ or $NHCOCH_3$ or

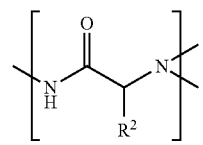

when $p=2$, $C^2$ is

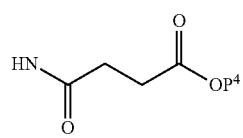

when $p=0$, $C^2$ is $NHP^2$ or $N(CH_2CO_2P^4)_2$ or $NHCOCH_3$ or

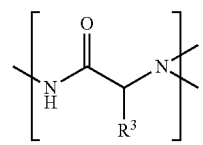

when $n=2$, $C^3$ is

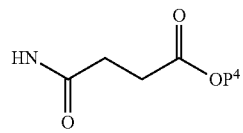

when $n=0$, $C^3$ is $NHP^2$ or $N(CH_2CO_2P^4)_2$ or $NHCOCH_3$ or

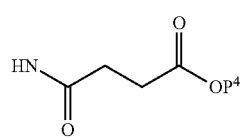

when $m=2$, $C^5$ is $NHP^2$ or $N(CH_2CO_2P^4)_2$ or $NHCOCH_3$ or and $C^4$ is

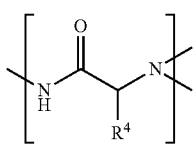

when m=0, $C^4$ is $NHP^2$ or $N(CH_2CO_2P^4)_2$ or $NHCOCH_3$ or

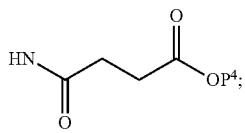

R, $R^0$, $R^1$, $R^2$, $R^3$ and $R^4$ are H or the side chain of a natural amino acid (except proline);
$P^1$ is H or a hydroxy protecting group;
$P^2$ is H or an amino protecting group;
$P^4$ is H or a carboxylic acid protecting group;
X is a leaving group or $OP^3$ or

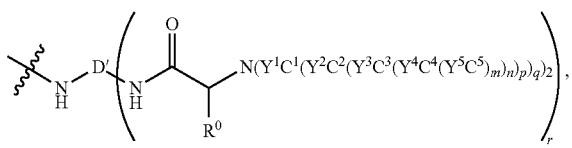

wherein $P^3$ is H or a carboxylic acid protecting group;
wherein:
  each of $Y^1$, $Y^2$, $Y^3$, $Y^4$, $Y^5$, $C^1$, $C^2$, $C^3$, $C^4$, $C^5$ are as previously defined and can be the same or different;
  m, n, p and q are as previously defined and can be the same or different;
  R, $R^0$, $R^1$, $R^2$, $R^3$ and $R^4$ are as previously defined and can be the same or different;
  r is 1, 2, or 3; and
  D' is an aryl; or a straight-, branched- or cyclo-alkyl moiety, or

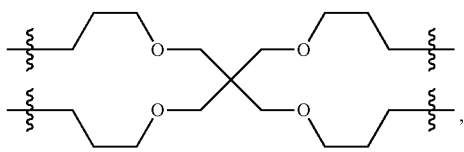 [SMILES: *CCCOCC(COCCC*)(COCCC*)COCCC*]

wherein when D' is

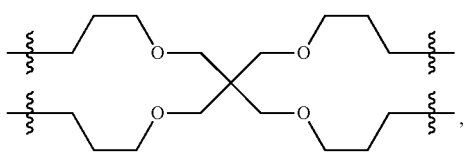 [SMILES: *CCCOCC(COCCC*)(COCCC*)COCCC*]

r is 3.

2. A compound as claimed in claim 1, wherein $P^1$ is selected from H, acetate, substituted acetate, benzoate, trialkylsilyl or allyl or benzyl.

3. A compound as claimed in claim 1, wherein $P^2$ is Boc, Fmoc or Cbz.

4. A compound as claimed in claim 1, wherein $P^4$ is H, tert-butyl or benzyl.

5. A compound as claimed in claim 1, wherein R, $R^0$, $R^1$, $R^2$, $R^3$ or $R^4$ are H, $—(CH_2)_4NH_2$ or $—(CH_2)_3NHC{=}NHNH_2$ or $—CH(CH_3)CH_2CH_3$ or $—CH_2Ph$ or $—CH_2CH(CH_3)_2$ or $—CH_3$, or $—(CH_2)_2SCH_3$, or $—CH_2CO_2H$ or $—(CH_2)_2CO_2H$ or $—CH(OH)CH_3$ or $—(CH_2)_2CONH_2$ or $—CH_2OH$ or $—CH_2SH$ or $—CH_2CONH_2$ or $—CH(CH_3)_2$ or

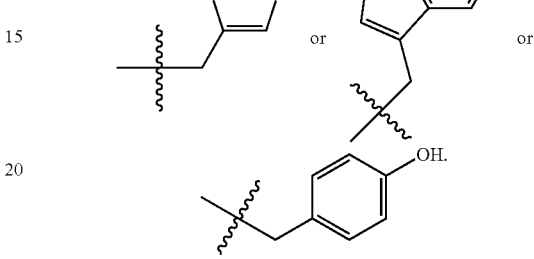

6. A compound as claimed in claim 1, wherein X is a leaving group or $OP^3$, and wherein $P^3$ is as defined in claim 1.

7. A compound as claimed in claim 6, wherein $P^3$ is alkyl or aralkyl.

8. A compound as claimed in claim 6, wherein X is OH.

9. A compound as claimed in claim 1, wherein $C^1$, $C^2$, $C^3$, $C^4$ or $C^5$ is a terminal group and is $N(CH_2CO_2P^4)_2$, wherein $P^4$ is as defined in claim 1.

10. A compound as claimed in claim 1, wherein $Y^1C^1$, $Y^2C^2$, $Y^3C^3$, $Y^4C^4$ or $Y^5C^5$ is a terminal group and is

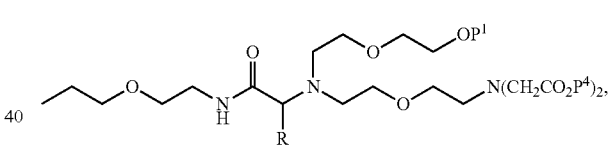

wherein $P^1$ and $P^4$ are as defined in claim 1.

11. A compound as claimed in claim 1, wherein $Y^1C^1$, $Y^2C^2$, $Y^3C^3$, $Y^4C^4$ or $Y^5C^5$ is a terminal group and is

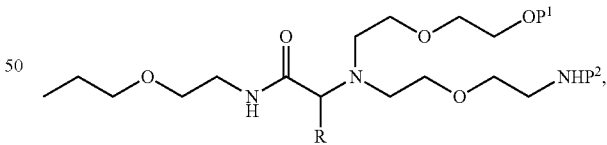

wherein $P^1$ and $P^2$ are as defined in claim 1.

12. A compound as claimed in claim 1, wherein $Y^1$, $Y^2$, $Y^3$, $Y^4$ or $Y^5$ are

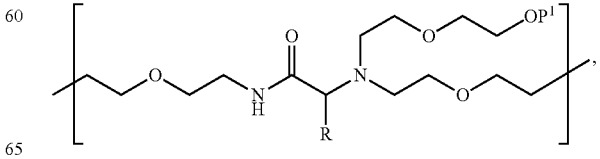

and wherein $P^1$ is as defined in claim 1.

13. A compound as claimed in claim 12, wherein the compound of formula (I) is:
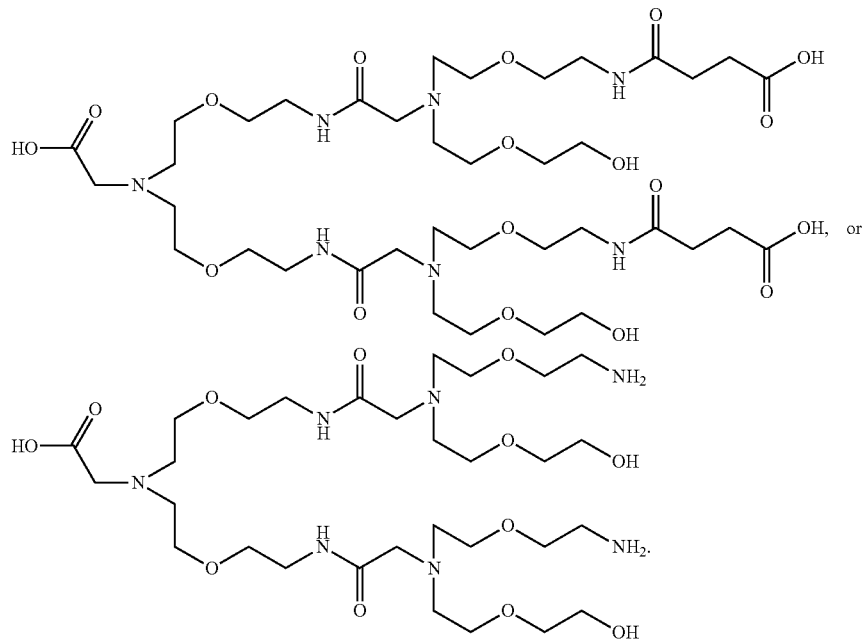
14. A compound as claimed in claim 1, wherein the compound of formula (I) is selected from the following:
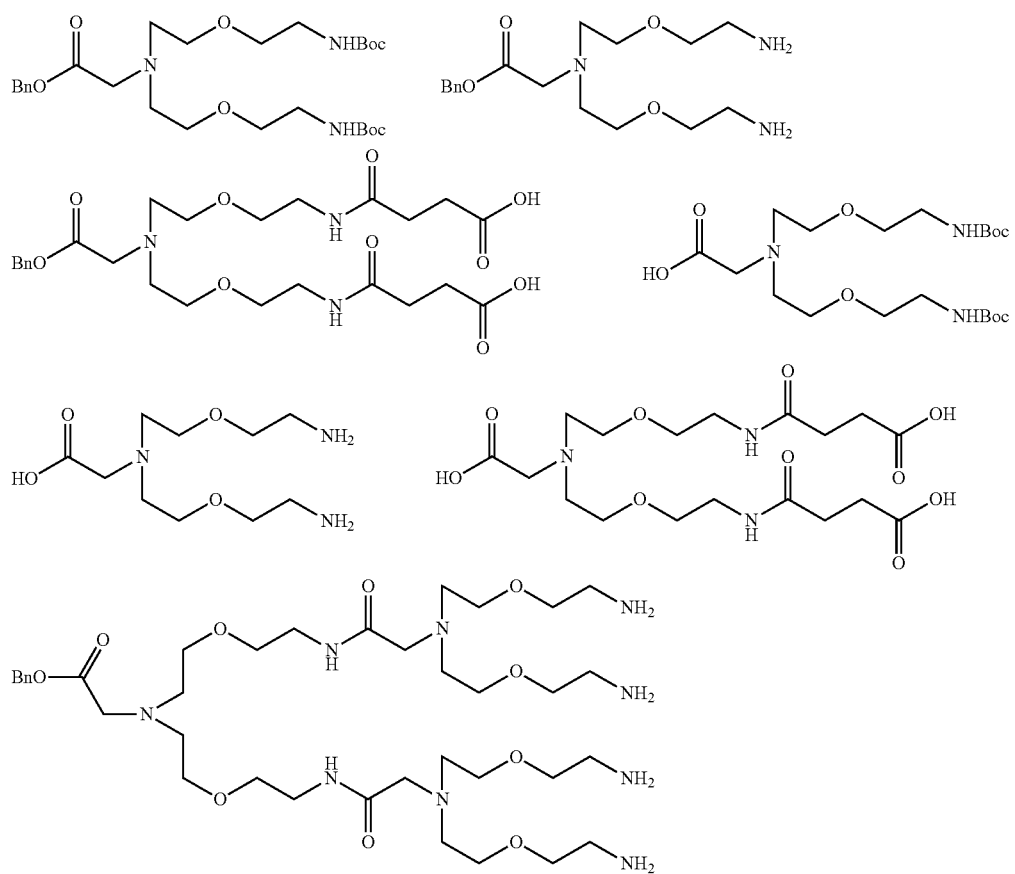

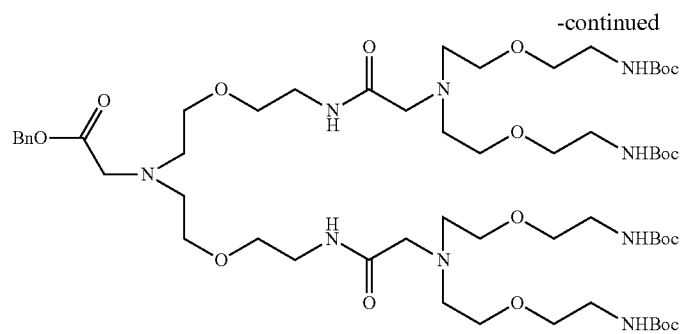
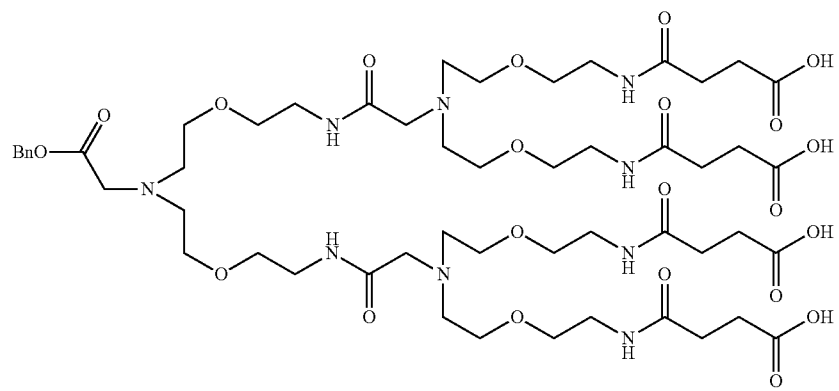
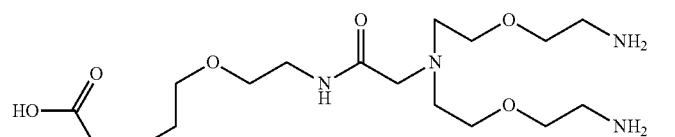
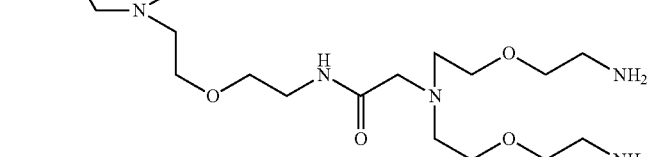
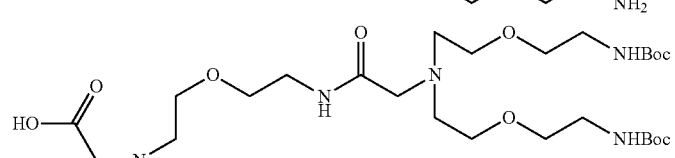
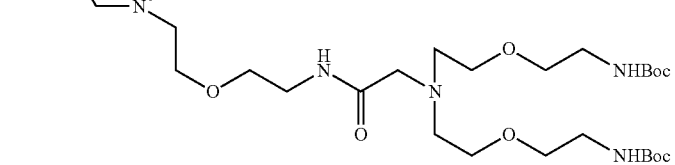
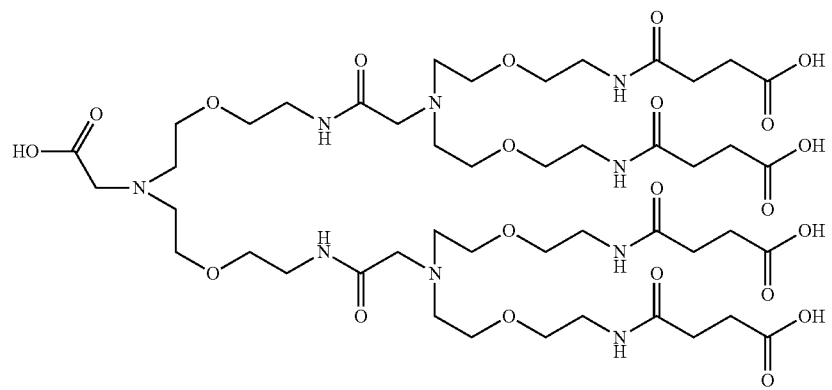

137
-continued
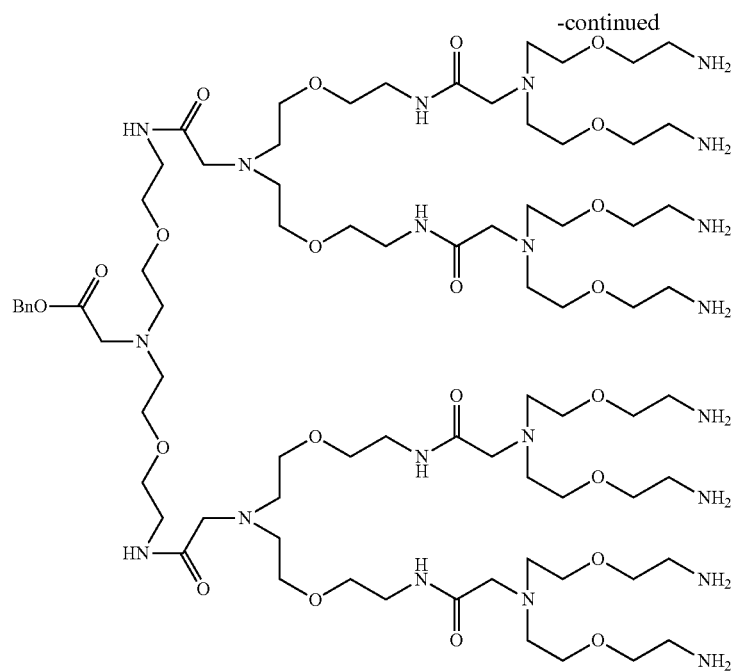
138
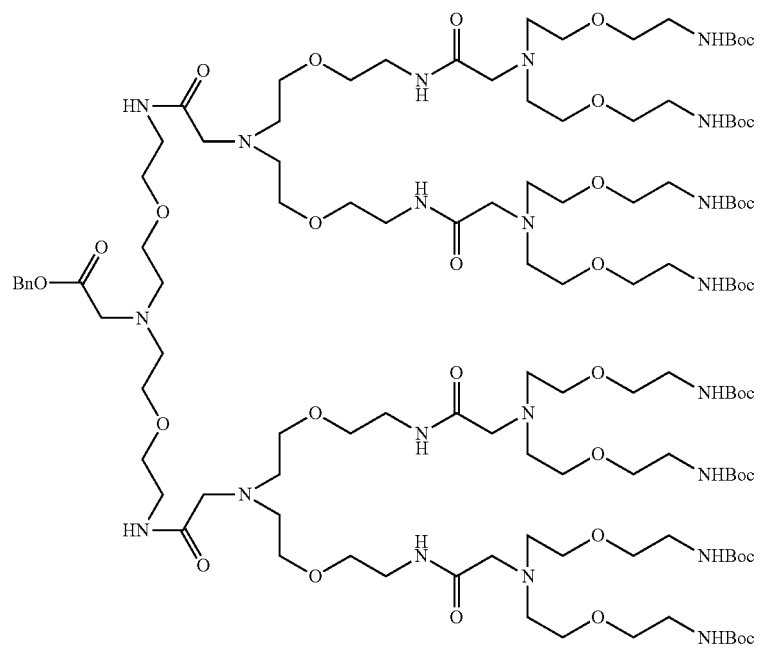

-continued
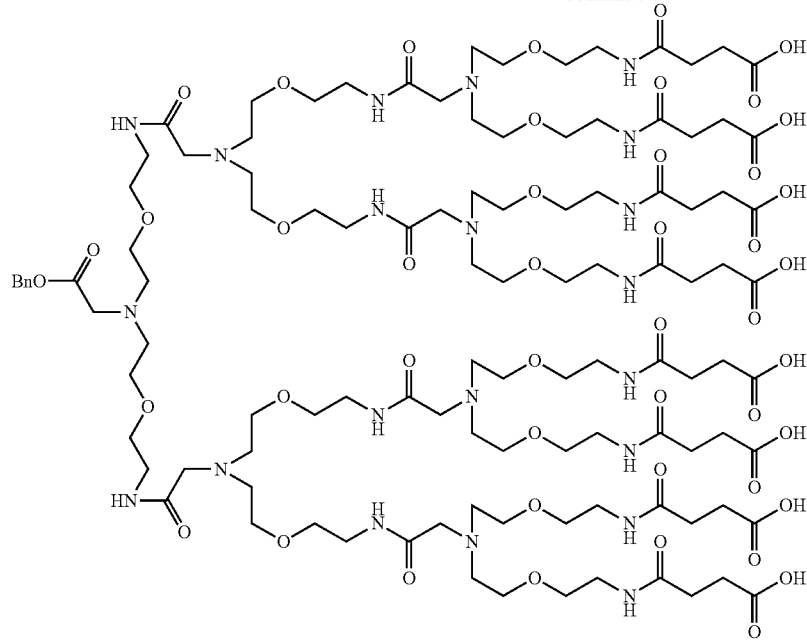
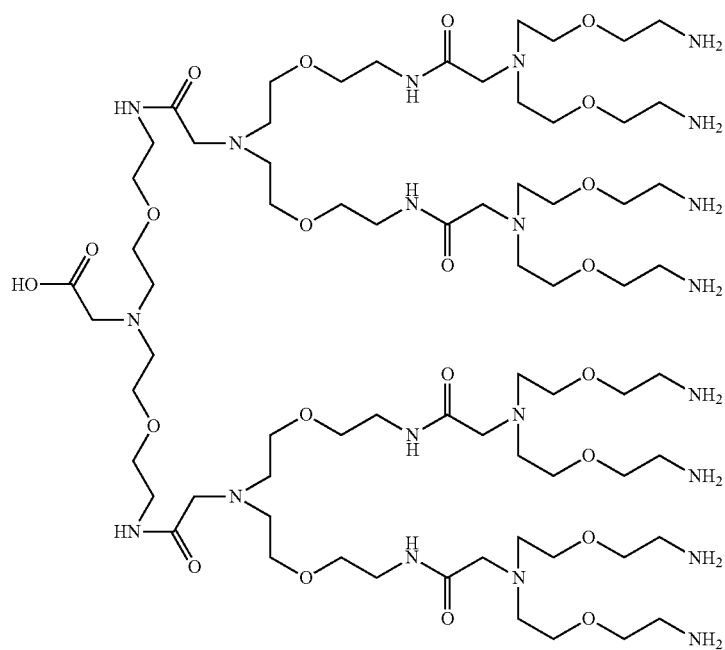

-continued
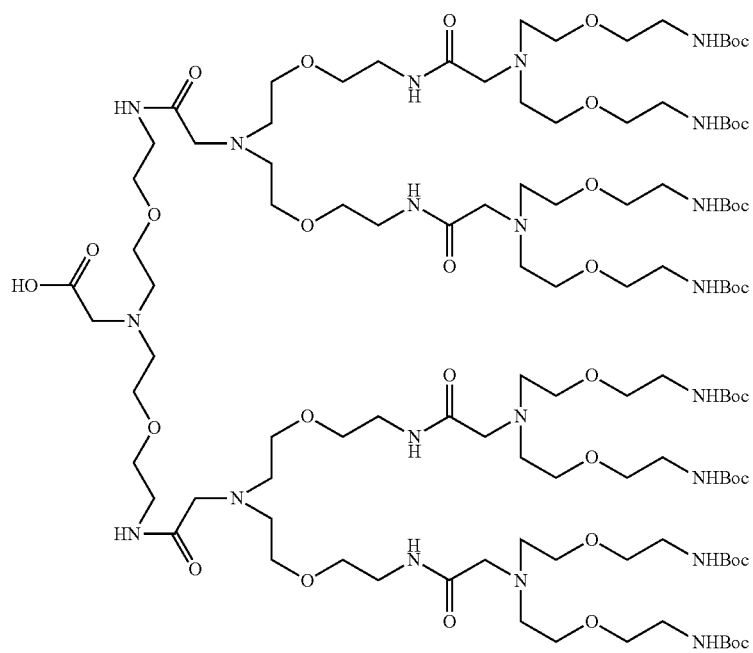
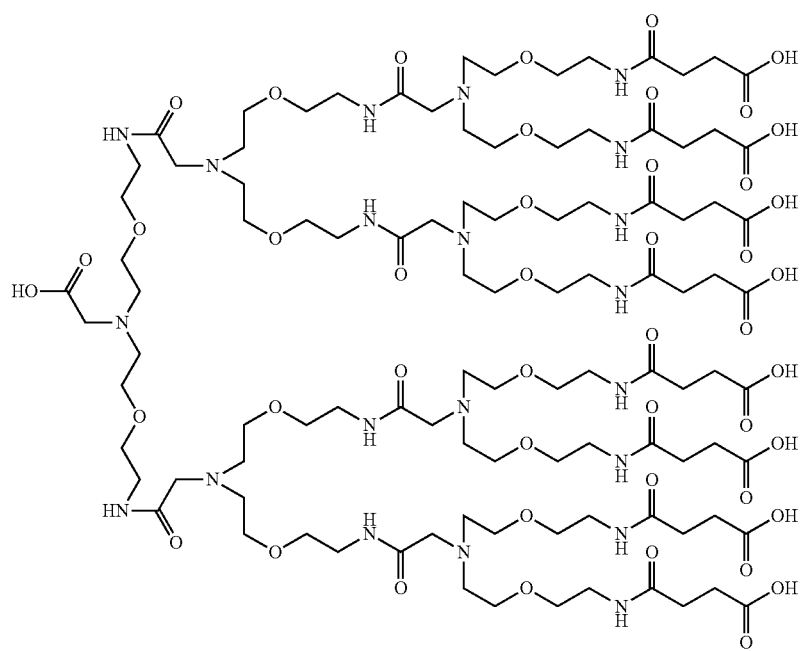

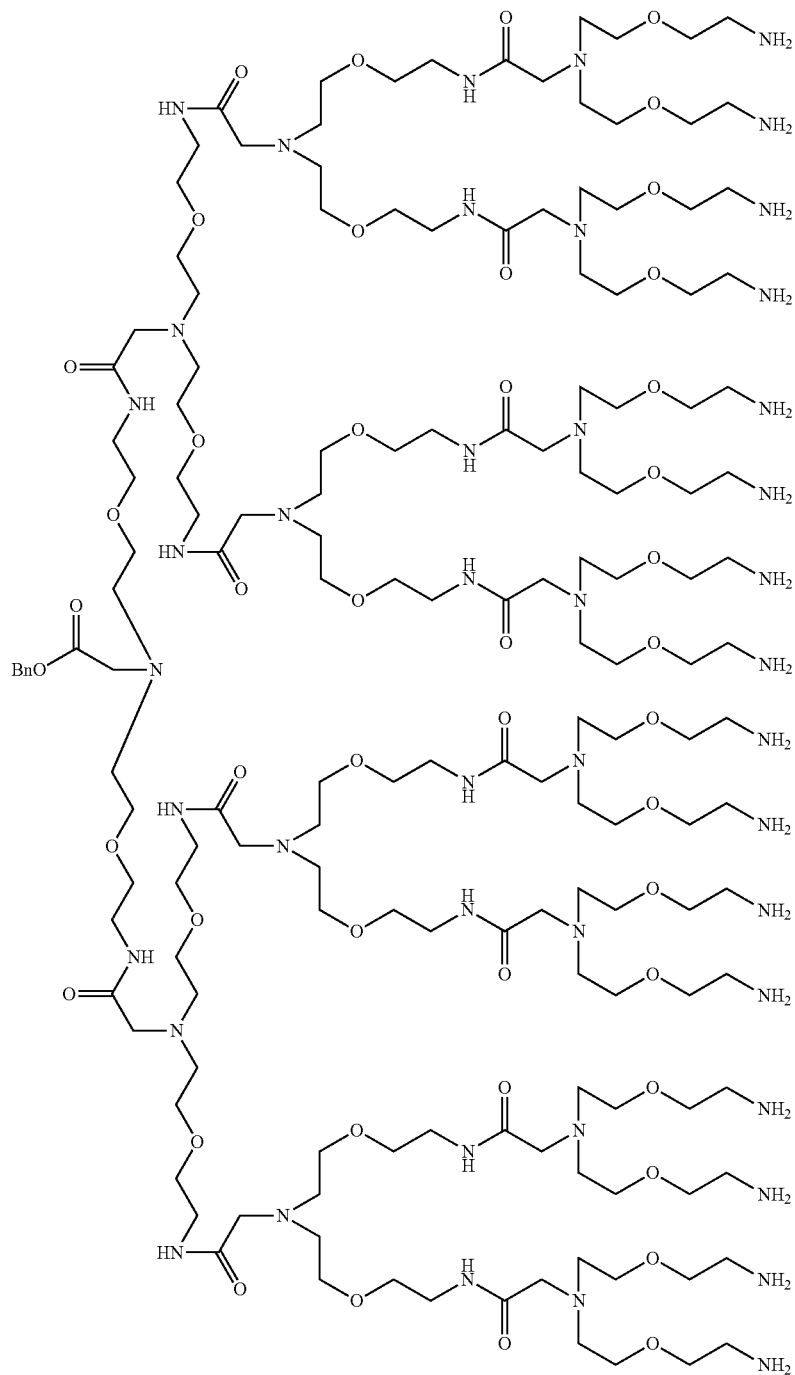 [SMILES: NCCOCCN(CCOCCN)CC(=O)NCCOCCN(CCOCCNC(=O)CN(CCOCCN)CCOCCN)CC(=O)NCCOCCN(CCOCCNC(=O)CN(CCOCCNC(=O)CN(CCOCCN)CCOCCN)CCOCCNC(=O)CN(CCOCCN)CCOCCN)CC(=O)NCCOCCN(CCOCCNC(=O)CN(CCOCCNC(=O)CN(CCOCCNC(=O)CN(CCOCCN)CCOCCN)CCOCCNC(=O)CN(CCOCCN)CCOCCN)CCOCCNC(=O)CN(CCOCCNC(=O)CN(CCOCCN)CCOCCN)CCOCCNC(=O)CN(CCOCCN)CCOCCN)CC(=O)OCc1ccccc1]

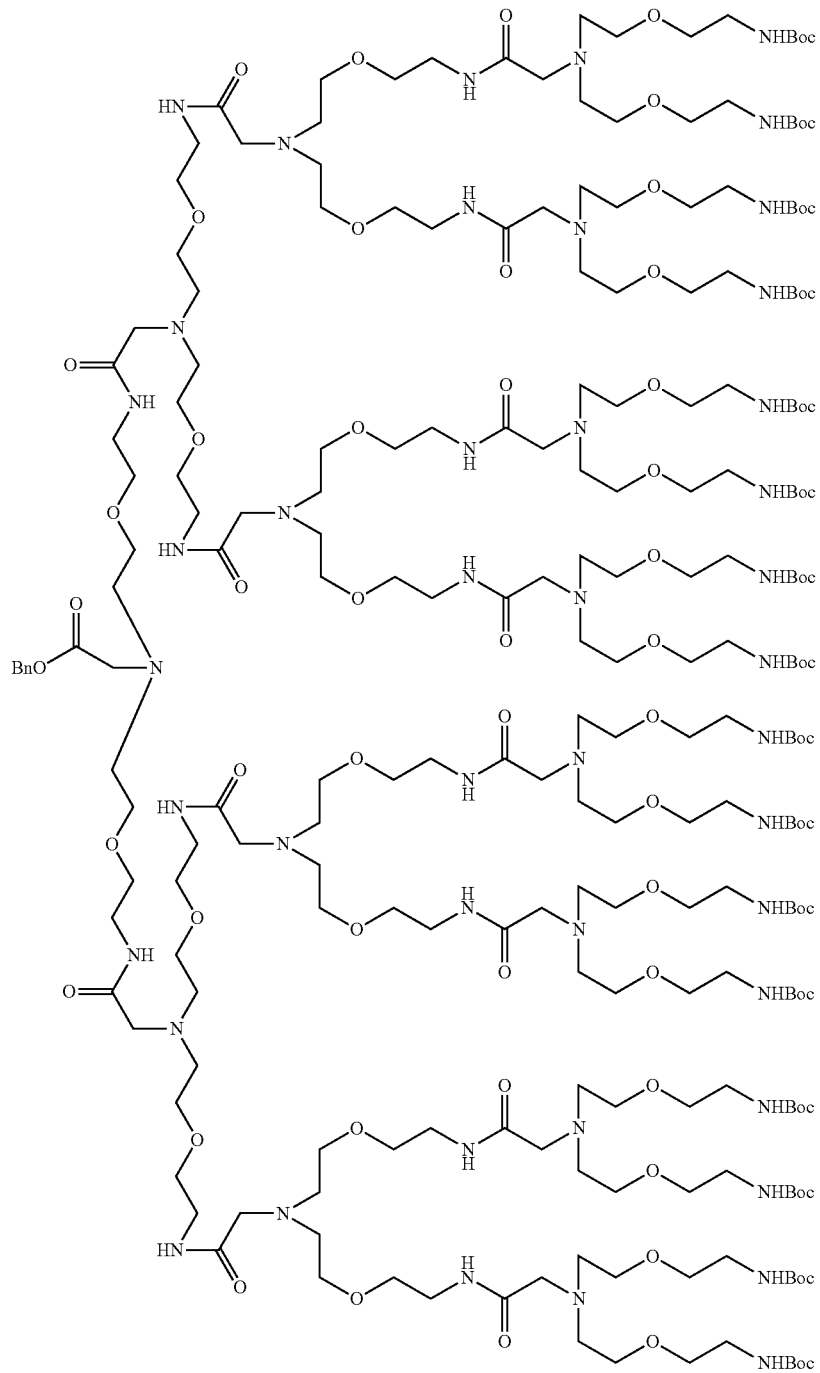

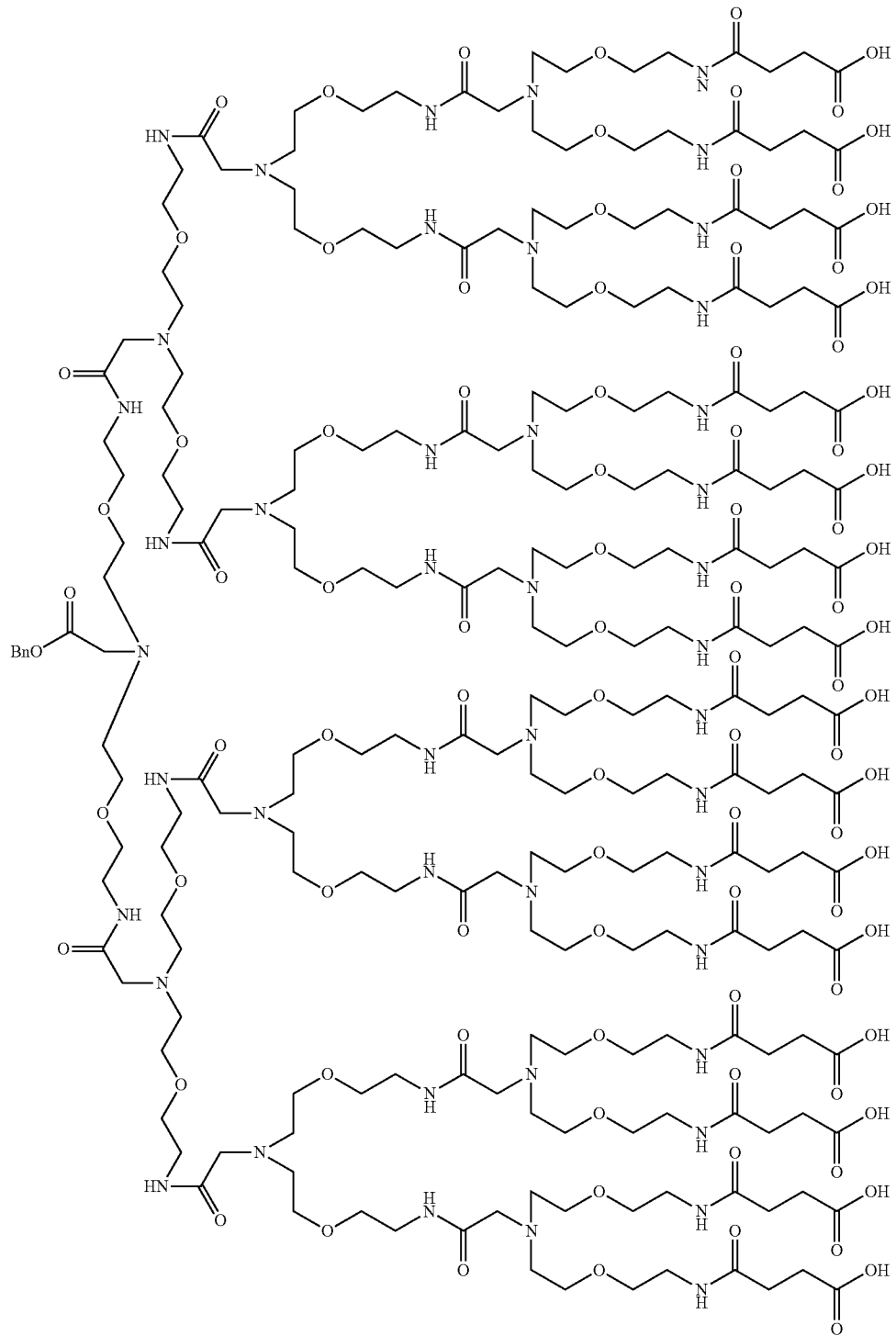

-continued
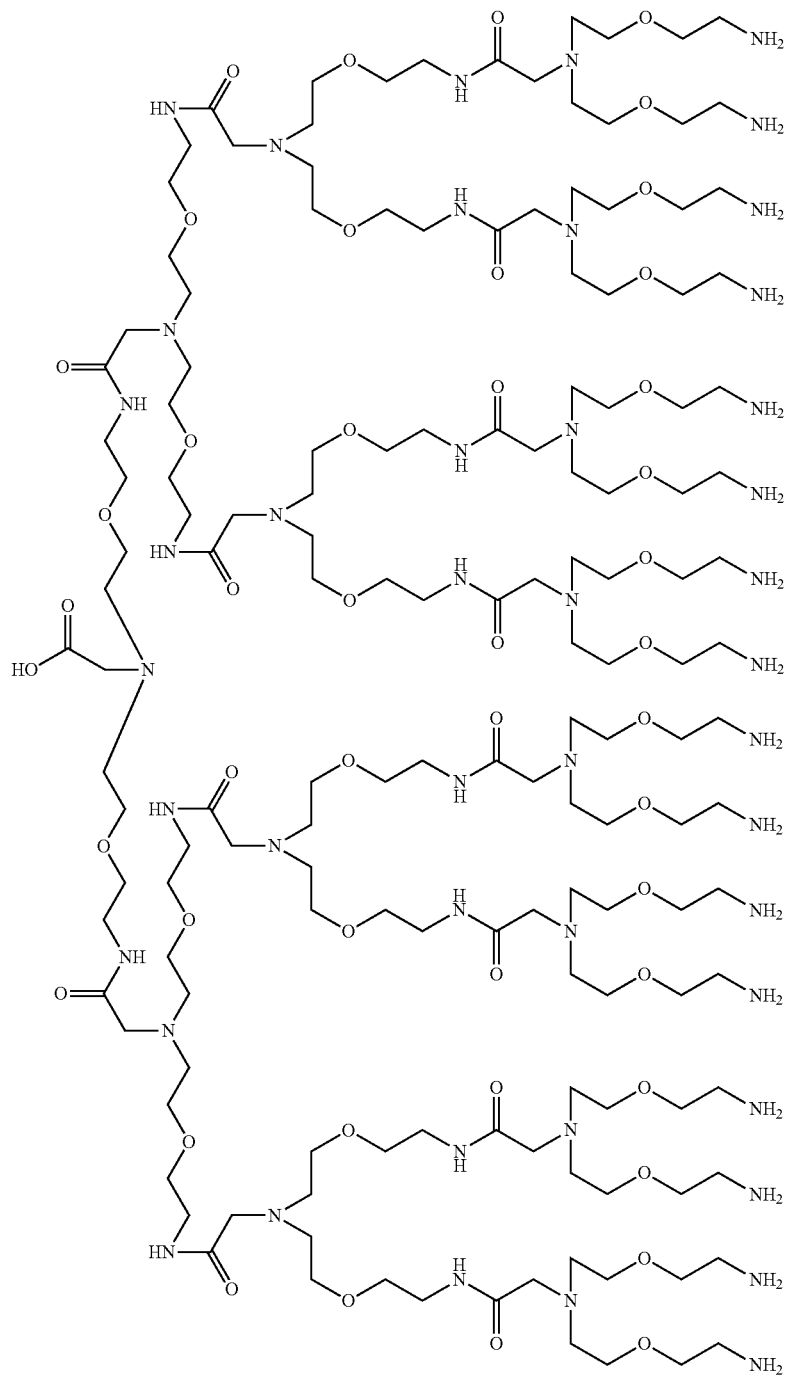 [SMILES: NCCOCCN(CCOCCN)CC(=O)NCCOCCN(CCOCCNC(=O)CN(CCOCCN)CCOCCN)CC(=O)NCCOCCN(CCOCCNC(=O)CN(CCOCCNC(=O)CN(CCOCCN)CCOCCN)CCOCCNC(=O)CN(CCOCCN)CCOCCN)CC(=O)NCCOCCN(CCOCCNC(=O)CN(CCOCCNC(=O)CN(CCOCCNC(=O)CN(CCOCCN)CCOCCN)CCOCCNC(=O)CN(CCOCCN)CCOCCN)CCOCCNC(=O)CN(CCOCCNC(=O)CN(CCOCCN)CCOCCN)CCOCCNC(=O)CN(CCOCCN)CCOCCN)CC(=O)O]

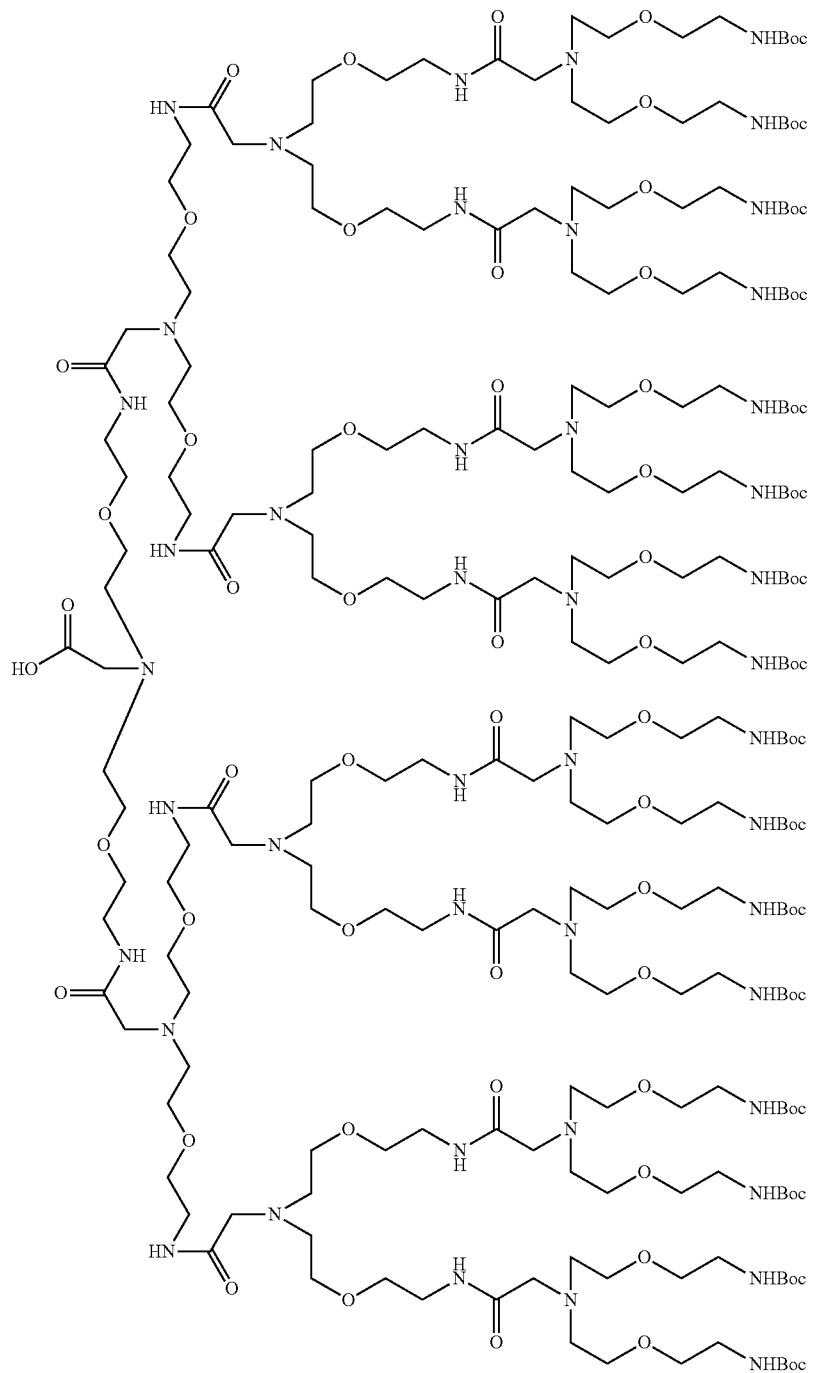

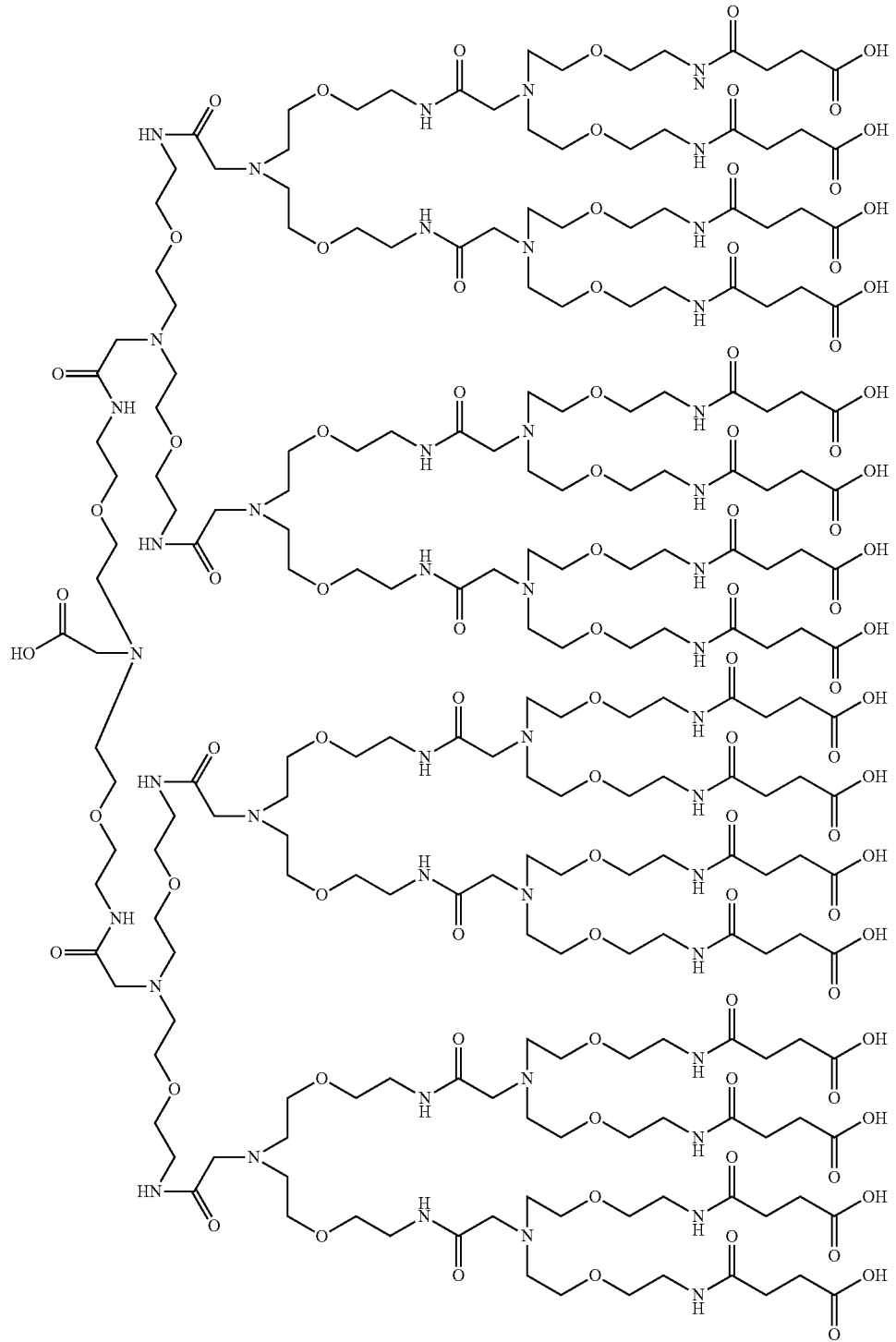

-continued
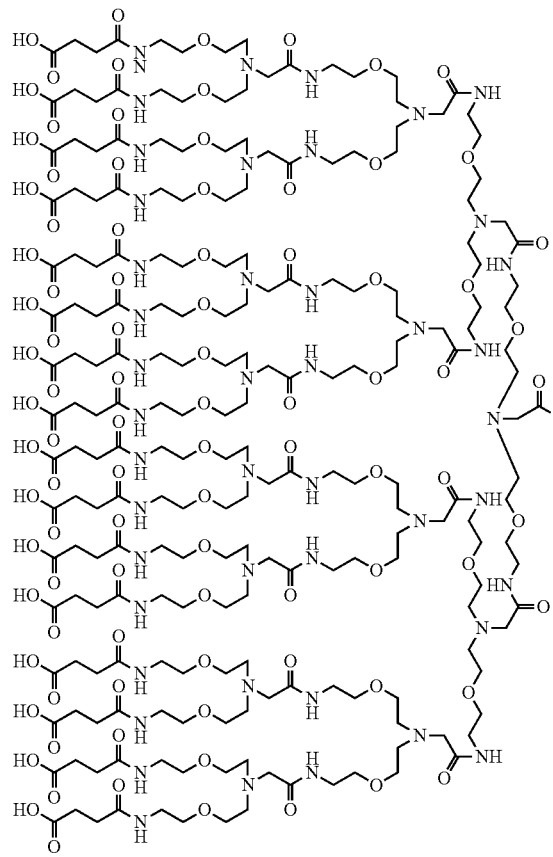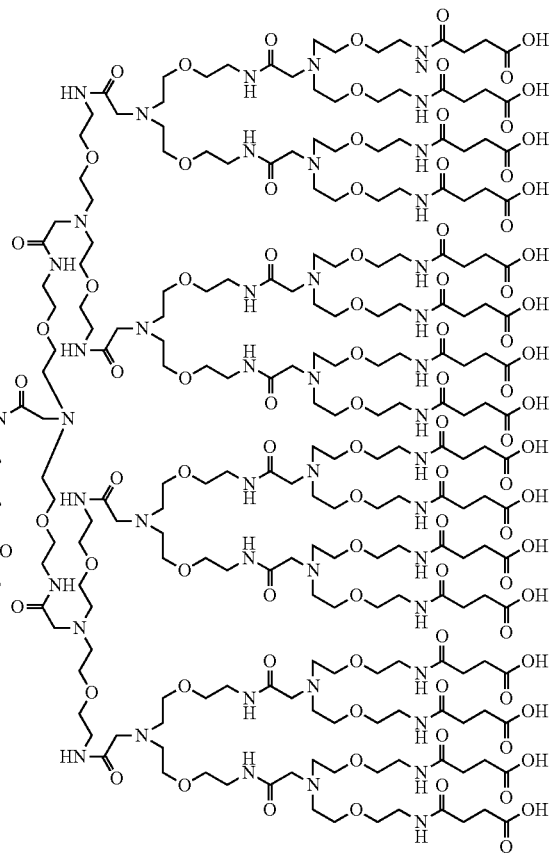
P = H or Bn

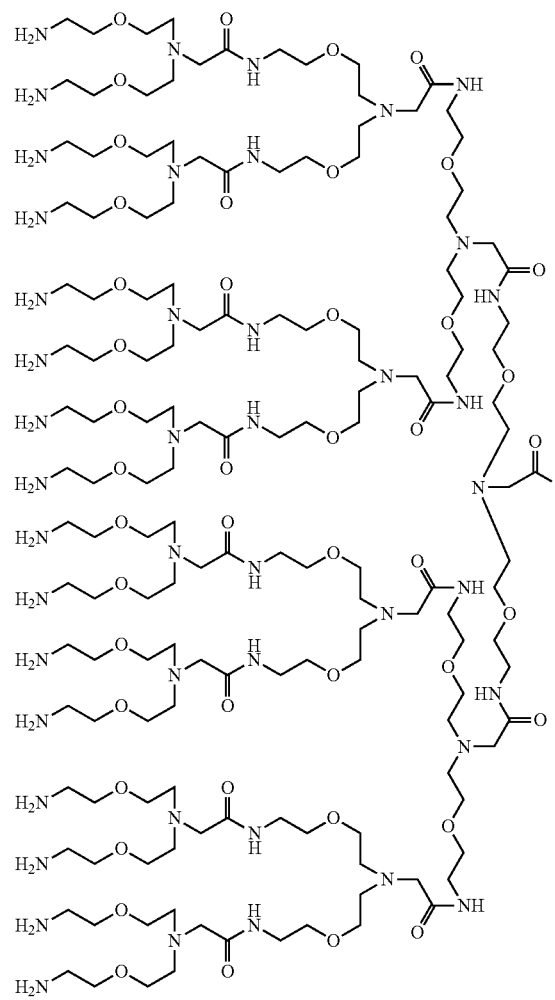
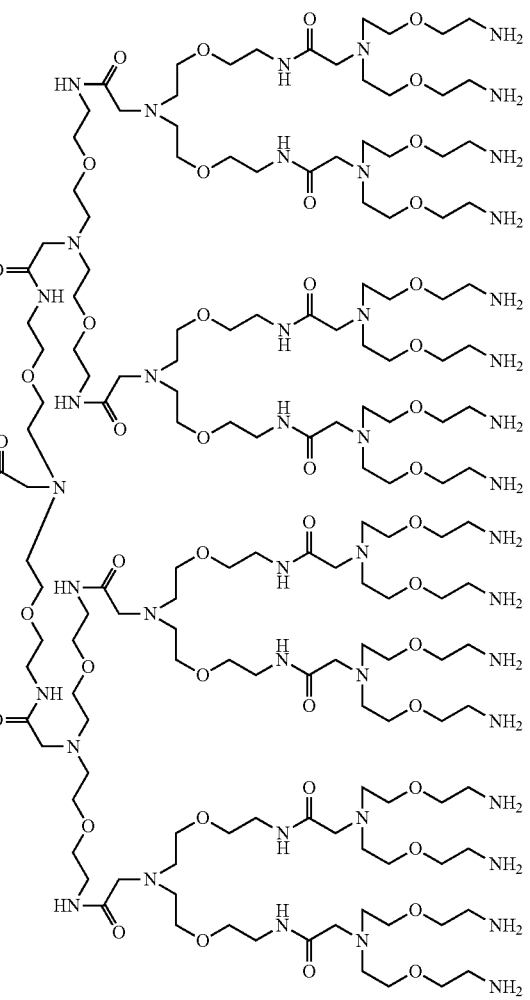
P = H or Bn

-continued

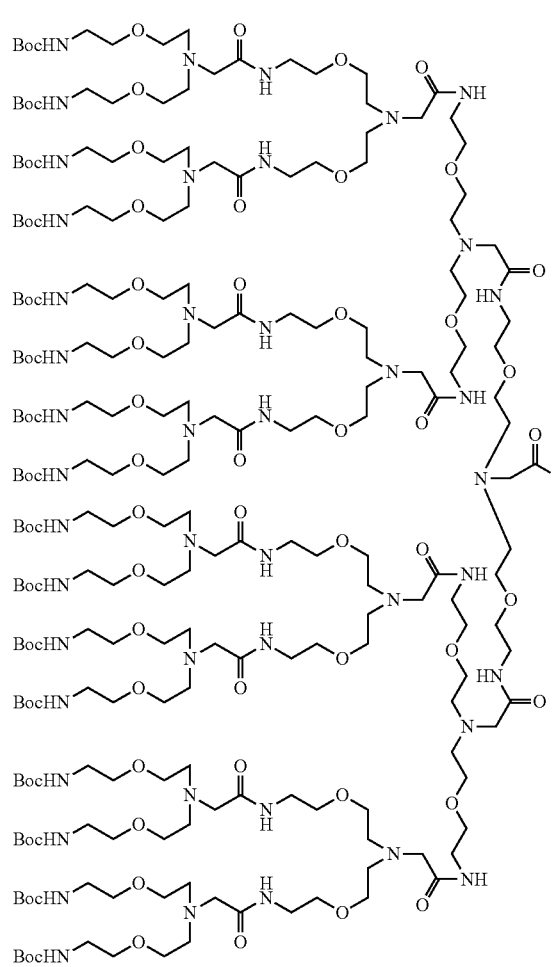
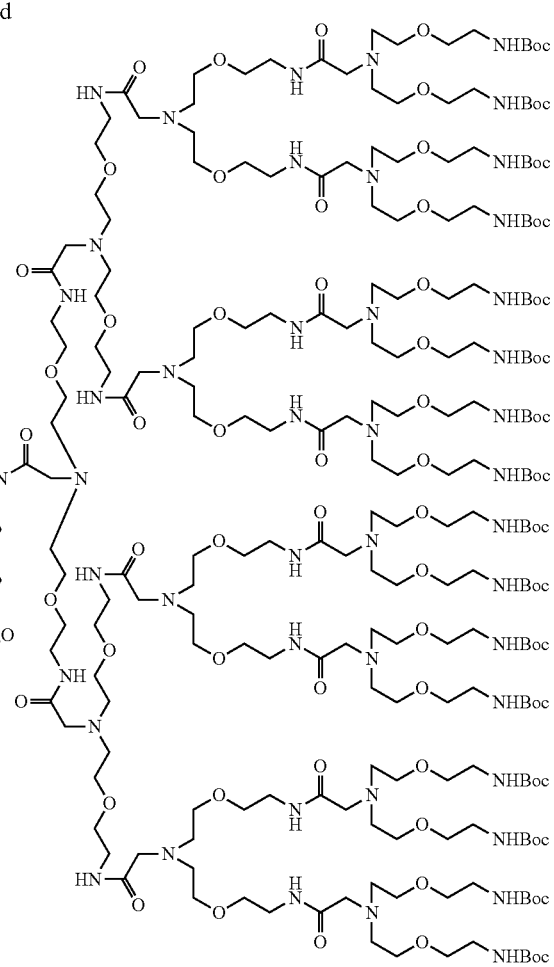

P = H or Bn

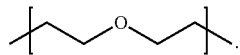

wherein:
any one or more of the NH$_2$ groups may be replaced with NHP$^2$ (as defined in claim 1); and
any one or more of the hydrogen atoms of the terminal carboxylic acid groups may be replaced with P$^3$ (as defined in claim 1).

15. A compound as claimed in claim 1, wherein any one or more of Y$^1$, Y$^2$, Y$^3$, Y$^4$ and Y$^5$ is

16. A compound as claimed in claim 1, wherein the compounds of formula (I) are neutral salts or salts of chloride, bromide, trifluoroacetate, p-toluenesulfonate, acetate, sulfate, hydrogen sulfate, carbonate, hydrogen carbonate, phosphate, hydrogen phosphate, triethylammonium, ammonium, or pyridinium.

17. A compound as claimed in claim 1, wherein the compound of formula (I) may be modified into therapeutic agents by the attachment of inactive agents.

18. A compound as claimed in claim 17, wherein the inactive agents include targeting agents and agents suitable for multivalent presentation.

19. A compound of formula (I) together with an active agent attached to, or encapsulated within, the compound of formula (I) as defined in claim 1.

20. A pharmaceutical composition comprising a compound of formula (I) together with an active agent attached to, or encapsulated within, the compound of formula (I) as defined in claim 1 together with suitable carriers and/or excipients.

\* \* \* \* \*